US008293517B2

(12) United States Patent
Cunningham

(10) Patent No.: US 8,293,517 B2
(45) Date of Patent: Oct. 23, 2012

(54) **METHODS AND COMPOSITIONS FOR THE IDENTIFICATION OF ANTIBIOTICS THAT ARE NOT SUSCEPTIBLE TO ANTIBIOTIC RESISTANCE IN *PSEUDOMONAS AERUGINOSA***

(75) Inventor: Philip R. Cunningham, Troy, MI (US)

(73) Assignee: Wayne State University, Detroit, MI (US)

( * ) Notice: Subject to any disclaimer, the term of this patent is extended or adjusted under 35 U.S.C. 154(b) by 998 days.

(21) Appl. No.: 11/914,062

(22) PCT Filed: May 11, 2006

(86) PCT No.: PCT/US2006/018187
§ 371 (c)(1),
(2), (4) Date: Jun. 30, 2008

(87) PCT Pub. No.: WO2006/122224
PCT Pub. Date: Nov. 16, 2006

(65) Prior Publication Data
US 2009/0130664 A1 May 21, 2009

Related U.S. Application Data

(60) Provisional application No. 60/680,134, filed on May 11, 2005.

(51) Int. Cl.
*C12N 1/21* (2006.01)
*C12N 15/00* (2006.01)
(52) U.S. Cl. .................................. 435/252.33; 435/320.1
(58) Field of Classification Search .......................... None
See application file for complete search history.

(56) References Cited

U.S. PATENT DOCUMENTS

| 4,772,555 A | 9/1988 | De Boer |
| 4,873,316 A | 10/1989 | Meade et al. |
| 5,821,058 A | 10/1998 | Smith et al. |
| 5,981,280 A | 11/1999 | Fang et al. |
| 7,045,337 B2 * | 5/2006 | Schultz et al. ............. 435/252.3 |
| 7,081,341 B2 | 7/2006 | Cunningham |

FOREIGN PATENT DOCUMENTS

| WO | WO 96/06106 A1 | 2/1996 |
| WO | WO-00/32619 A1 | 6/2000 |
| WO | WO-01/42445 A2 | 6/2001 |
| WO | WO-02/29019 | 4/2002 |
| WO | WO-03/029459 | 4/2003 |
| WO | WO 2004/003511 A2 | 1/2004 |
| WO | WO-2006/115570 | 11/2006 |

OTHER PUBLICATIONS

Cornelis et al., Mol. Micro. 3, 3, 421-428, 1989.*
Ochi et al., Intl. J. Syst. Bact. 45, 2, 268-273, 1995.*
Kozak, M. (2005) Regulation of translation via mRNA structure in prokaryotes and eukaryotes: Gene; 361:13-37.
Asai, T., (1999) "Construction and initial characterization of *Escherichia coli* strains with few or no intact chromosomal rRNA operons"; *J. Bacteriol.* 181: 3803-3809.
Baldari et al. (1987) "A novel leader peptide which allows efficient secretion of a fragment of human interleukin 1β In *Saccharomyces cerevisiae*"; *EMBO J.* 6:229-234.
Banerji et al. (1983) "A lymphocyte-specific cellular enhancer is located downstream of the joining region in immunoglobulin heavy chain genes," *Cell* 33:729-740.
Brosius, J., et al. (1981); "Construction and fine mapping of recombinant plasmids containing the *rrnB* ribosomal RNA operon of *Escherichia coli*"; *Plasmid* 6:112-118.
Brow, D. A. & Noller, H. F. (1983) "Protection of ribosomal RNA from Kethoxal in polyribosomes"; *J. Mol. Biol.* 163:112-118.
Byrne and Ruddle (1989) "Multiplex gene regulation: a two-tiered approach to transgene regulation in transgenic mice"; *Proc. Natl. Acad. Sci. USA* 86:5473-5477.
Calame and Eaton (1988) "Transcriptional controlling elements in the immunoglobulin and T cell receptor loci," *Adv. Immunol.* 43:235-275.
Calos, M.P. (1978) "DNA sequence for a low-level promoter of the *lac* repressor gene and an 'up' promoter mutation"; *Nature* 274:762-765.
Capaldi, D. & Reese, C. (1994) "Use of the 1-(2-fluorophenyl)-4-methoxypiperidin-4-yl (Fpmp) and related protecting groups in oligoribonucleotide synthesis: stability of internucleotide linkages to aqueous acid"; *Nucl. Acids Res.* 22:2209-2216.
Carter-Muenchau, P. & Wolf, R. E. (1989) "Growth-rate dependent regualtion of 6- phosphogluconate dehydrogenase level mediated by an anti-Shine-Dalgarno sequence located within the *Escherichia coli* gnd structural gene"; Proc. Natl. Acad. Sci. USA 86:1138-1142.
Chen, H., et al. (1994) "Determination of the optimal aligned spacing between the Shine-Dalgarno sequence and the translation initiation codon of *Escherichia coli* mRNAs"; *Nucl. Acids Res.* 22: 4953-4957.
Cunningham, P., et al. (1993) "Functional effects of base changes which further define the decoding center of *Escherichia coli* 16S ribosomal RNA: mutation of C1404, G1405, C1496, G1497, and U1498," *Biochemistry* 32: 7172-7180.
de Boer, H. A., et al. (1983) "The tac promoter: a functional hybrid derived from the *trp* and *lac* promoters"; *Proc. Natl Acad. Sci. USA* 80:21-25.

(Continued)

*Primary Examiner* — Nancy T Vogel
(74) *Attorney, Agent, or Firm* — Senniger Powers LLP

(57) ABSTRACT

The "instant evolution" system was initially developed in *E. coli*, primarily because of the ease with which this organism can be genetically manipulated. Because many of the functionally important regions of rRNA are conserved among bacteria, drug leads developed against conserved targets in the *E. coli* system may produce broad-spectrum anti-infectives. However, in order the develop a system to product narrow-spectrum anti-infectives, herein we disclose method and compositions for screening *Pseudomonas aeruginosa* 16S rRNA in *E. coli* cells. In certain embodiments, a plasmid comprising the 16S rRNA gene from *Pseudomonas aeruginosa* t mutated to replace the natural helix 9 region with the corresponding region of the *E. coli* rRNA, is shown to form functional ribosomes in *E. coli* host cells. Li other embodiments, a plasmid, comprising the unmutated 16S rRNA from *Pseudomonas aeruginosa*, along with a plasmid containing the *Pseudomonas aeruginosa* S20 protein, can yield functional ribosomes in *E. coli* cells.

18 Claims, 53 Drawing Sheets

OTHER PUBLICATIONS

Denman, R. et al. (1989) "In vitro assembly of 30S and 70S bacterial ribosomes from 16S RNA containing single base substitutions, insertions, and deletions around the decoding site (C1400)," *Biochemistry* 28:1002-1011.

Dower, W. J., et al. (1988) "High efficiency transformation of *Escherichia coli* by high voltage electroporation"; *Nucl. Acids Res.* 16: 6127.

Edlund et al. (1985) "Cell-specific expression of the rat insulin gene: evidence for role f two distinct 5' flanking elements"; *Science* 230:912-916.

Goeddel (1990) "Systems for heterologous gene expression"; *Methods Enzymol.* 185:3-7.

Gottesman, S. (1990) "Minimizing proteolysis in *Escherichia coli*: genetic solutions"; *Methods Enzymol.* 185:119-128.

Govantes, F. et al. (1998) "Mechanism of translational coupling in the nifLA operon of *Klebsiella pneumoniae*"; *EMBO J.* 17(8):2368-2377.

Gutell, R. R. (1994) "Collection of small subunit (16S- and 16S-like) ribosomal RNA structures"; *Nucl. Acids Res.* 22: 3502-3507.

Hanahan, D. (1983) "Studies on transformation of *Escherichia coli* with plasmids"; *J. Mol. Biol.* 166:557-580.

Herr, W., et al. (1979) "Mechanism of ribosomal subunit association: discrimination of specific sites in 16S RNA essential for association activity"; *J. Mol. Biol.* 130: 433-449.

Higuchi, R. (1989) "Using PCR to engineer DNA"; PCR Technology (Erlich, H.A., ed.), pp. 61-70, Stockton Press, New York.

Hui, A., et al. (1987) "Specialized ribosome system: preferential translation of a single mRNA species by a subpopulation of a mutated ribosome in *Escherichia coli*"; Proc. Natl. Acad. Sci. U.S.A. 84: 4762-4766.

Hui, A., et al. (1987) "Directing ribosomes to a single mRNA species: a method to study ribosomal RNA mutations and their effects on translation of a single messenger in *Escherichia coli*"; Methods Enzymol. 153: 432-452.

Kaufman, et al. (1987) "Translation efficiency of polycistronic mRNAs and their utilization to express heterologous genes in Mammalian Cells"; EMBO J. 6:187-195.

Kessel and Gruss (1990) "Murine developmental control genes"; Science 249:374-379.

Koosha, H., et al. (2000) "Alterations in the peptidyltransferase and decoding domains of ribosomal RNA suppress mutations in the elongation factor G gene"; *RNA.* 6: 1166-1173.

Kurjan and Herskowitz (1982) "Structure of a yeast pheromone gene (MF alpha): a putative alpha-factor precursor contains four tandem copies of mature alpha-factor," *Cell* 30:933-943.

Lee, K., et al. (2001) "Genetic Approaches to Studying Protein Synthesis: Effects of Mutations at Pseudouridine 516 and A535 in *Escherichia coli* 16S rRNA"; *Symposium: Translational Control: A Mechanistic Perspective* at the Experimental Biology 2001 Meeting.

Lee, K., et al. (1997) "In vivo determination of RNA structure-function relationships: analysis of the 790 loop in ribosomal RNA"; J. Mol. Biol. 269:732-743.

Lee, K., et al. (1996) "Genetic analysis of the Shine-Dalgarno interaction: selection of alternative functional mRNA-rRNA combinations"; RNA 2: 1270-1285.

Luria, S.E. & Burrous, J.W. (1957); "Hybridization between *Escherichia coli* and shigella"; J. Bacteriol. 74:461-476.

Maden, B. E. (1990); "The numerous modified nucleotides in eukaryotic ribosomal RNA"; Prog. Nucleic Acid Res. Mol. Biol. 39: 241-303.

Maidak, B. L. et al. (1996); "The ribosomal database project (RDP)"; Nucl. Acids Res. 24: 82-85.

Makosky, P. C. et al. (1987) "Spectinomycin resistance at site 1192 in 16S ribosomal RNA of *E. coli*: an analysis of three mutants," Biochimie 69: 885-889.

Miller, J.H. (1992) "A Short Course in Bacterial Genetics", (Miller, J. H., ed.), pp. 71-80, Cold Spring Harbor Laboratory Press, Cold Spring Harbor, NY.

Moazed, D. & Noller, H.F. (1986) "Interconversion of active and inactive 30S ribosomal subunits is accompanied by a conformation change in the decoding region of 16S rRNA"; J. Mol. Biol. 191:483-493.

Morosyuk S. V., et al. (2001) "Structure and function of the conserved 690 hairpin in *Escherichia coli* 16S ribosomal RNA. II. NMR solution structure"; J. Mol. Biol. 307 (1):197-210.

Morosyuk S. V., et al. (2001) "Structure and function of the conserved 690 hairpin in *Escherichia coli* 16S ribosomal RNA. III. Functional analysis of the 690 loop"; J. Mol. Biol. 307 (1):213-228.

Morosyuk S. V., et al. (2000) "Structure and function of the conserved 690 hairpin in *Escherichia coli* 16S ribosomal RNA"; J. Mol. Biol. 300 (1):113-126.

Nielsen, D. A. et al. (1989) "A highly sensitive, mixed-phase assay for chloramphenicol acetyltransferase activity in transfected cells," Anal. Biochem. 179: 19-23.

O'Connor, M., et al. (2001) "Enhancement of translation by the epsilon element is independent of the sequence of the 460 region of 16S rRNA"; Nucl. Acids Res. 29: 1420-1425.

O'Connor, M., et al. (2001) "Mutagenesis of the peptidyltransferase center of 23S rRNA: the invariant U2449 is dispensable"; Nucl. Acids Res. 29: 710-715.

Pinkert, et al. (1987) "An albumin enhancer located 10 kb upstream functions along with its promoter to direct efficient, liver-specific expression in transgenic mice"; Genes Dev. 1:268-277.

Powers, T. et al. (1991) "A functional pseudoknot in 16S ribosomal RNA"; *EMBO J.* 10: 2203-2214.

Queen, C. & Baltimore, D. (1983) "Immunoglobulin gene transcription is activated by downstream sequence elements." *Cell* 33:741-748.

Schottel, J. L., et al. (1984) "Effects of alterations in the translational control region on bacterial gene expression: use of *cat* gene constructs transcribed from the *lac* promoter as a model system"; *Gene* 28: 177-193.

Schultz et al. (1987) "Expression and secretion in yeast of a 400-kDa envelope glycoprotein derived from Epstein-Barr virus"; *Gene* 54:113-123.

Seed, B. (1987) "An LFA-3 cDNA encodes a phospholipid-linked membrane protein homologous to its receptor CD2"; *Nature* 329:840.

Sergiev, P. V., et al. (2000) "Mutations at position A960 of *Escherichia coli* 23S ribosomal RNA influence the structure of 5S ribosomal RNA and the peptidyltransferase region of 23 S ribosomal RNA"; J. Mol. Biol. 299:379-389.

Sigmund, C. D., et al. (1988) "Antibiotic resistance mutations in ribosomal RNA genes of *Escherichia coli*"; Methods Enzymol. 164: 673-690.

Sigmund, C. D., et al. (1984) "Antibiotic resistance in 16S and 23S ribosomal RNA genes of *Escherichia coli*"; Nucl. Acids Res. 12:4653-4663.

Sigmund, C. D. et al. (1982) "Erythromycin resistance due to a mutation in a ribosomal RNA operon of *Escherichia coli*"; Proc. Natl. Acad. Sci. U.S.A. 79: 5602-5606.

Smith, D.B. and Johnson, K.S. (1988); "Single-step purification of polypeptides expressed in *Escherichia coli* as fusions with glutathione S-transferase"; Gene 67:31-40.

Stormo, G. D., et al. (1982) "Characterization of translational initiation sites in *Escherichia coli*"; Nucleic Acids Res. 10:2971-2996.

Tapprich, W., et al. (1989) "Mutation at position 791 *Escherichia coli* 16S ribosomal RNA affects processes involved in the initiation of protein synthesis"; Proc. Natl Acad. Sci. USA 86: 4927-4931.

Tapprich, W. & Hill, W. (1986); "Involvement of bases 787-795 of *Escherichia coli* 16S ribosomal RNA in ribosomal subunit association"; Proc. Natl Acad. Sci. USA 83: 556.

Triman, K., et al. (1989) "Isolation of temperature-sensitive mutants of 16S rRNA in *Escherichia coli*"; J. Mol. Biol. 209:645-653.

Vila-Sanjurjo, A. et al. (2001) "Mutational analysis of the conserved bases C1402 and A1500 in the center of the decoding domain of *Escherichia coli* 16S rRNA reveals an important tertiary interaction"; J. Mol. Biol. 308: 457-463.

Voulgaris, J., et al. (1999) "Increased rrn gene dosage causes intermittent transcription of rRNA in *Escherichia coli*"; J. Bacteriol. 181: 4170-4175.

Wada et al. (1992) "Codon usage tabulated from the Genbank genetic sequence data"; Nucl. Acids Res. 20:2111-2118.

Winoto and Baltimore (1989) "A novel, inducible and T cell-specific enhancer located at the 3' end of the T cell receptor α locus"; EMBO J. 8:729-733.
Yanisch-Perron, C., et al. (1985) "Improved M13 phage cloning vectors and host strains: nucleotide sequences of the M13mp18 and pUC19 vectors"; Gene 33:103-119.
Bottger, E., et al. (1994) Resistance to drugs targeting protein synthesis in mycobacteria: Trends in Microbiology; 2(10):416-421.
Laios, E., et al. (2004) "Combinatorial genetic technology for the development of new anti-infectives"; Arch Pathol Lab Med.; Dec; 128 (12); pp. 1351-1359.
Lee, K., et al. (2001) "Genetic approaches to studying protein synthesis: effects of mutations at Psi516 and A535 in *Escherichia coli* 16S rRNA"; J Nutr 131:2994S-3004S.
Supplemental European Search Report for EP 03 76 2329 dated Nov. 10, 2005.
International Search Report for PCT/US06/18320 dated Nov. 28, 2007.
Supplemental European Search Report for EP 06 75 9609 dated Jan. 13, 2009.
Adachi, J. A., et al. (2002) "Natural history of enteroaggregative and enterotoxigenic *Escherichia coli* infection among US travelers to Guadalajara, Mexico"; J Infect Dis 185:1681-3.
Adang, A. E. P., et al. (1994) "Case Histories of Peptidomimetics: Progression from Peptides to Drugs"; Recl. Tray. Chim. Pays-Bas 113:63-78.
Agalarov, S. C., et al. (2000) "Structure of the S15,S6,S18-rRNA complex: assembly of the 30S ribosome central domain"; Science 288:107-112.
Ahn, J. M., et al. (2002) "Peptidomimetics and Peptide Backbone Modifications"; Mini Rev. Med. Chem. 2:463-473.
Andersson, D. I., et al. (1998) "Antibiotic resistance here to stay? Compensatory mutations restore virulence of resistant bacteria"; Lakartidningen 95:3940, 3943-4.
Ang, J. Y., et al. (2004) "Antibacterial resistance"; Indian J Pediatr 71:229-39.
Aoki, H., et al. (2002) "Oxazolidinone antibiotics target the P site on *Escherichia coli* ribosomes"; Antimicrob Agents Chemother 46:1080-5.
Barrick, J. E., et al. (2001) "Selection of RNA-Binding Peptides Using mRNA-Peptide Fusions"; Methods 3:287-293.
Barrick, J. E. & Roberts, R. W. (2002) "Sequence Analysis of an Artifical Family of RNA-Binding Peptides"; Protein Sci. 11:2688-2696.
Batey, R. T., et al. (1992) "Preparation of isotopically labeled ribonucleotides for multidimensional NMR spectroscopy of RNA"; Nucleic Acids Res. 20:4515-4523.
Batey, R. T. & Williamson, J. R. (1996) "Interaction of the *Bacillus stearothermophilus* ribosomal protein S15 with 16 S rRNA: II. Specificity determinants of RNA-protein recognition"; J Mol Biol 261:550-67.
Bhattacharya, S. K., et al. (2003) "Multidrug-resistant *Shigella dysenteriae* type 1 in south Asia"; Lancet Infect Dis 3:755.
Bjorkman, J., et al. (2000) "Effects of environment on compensatory mutations to ameliorate costs of antibiotic resistance"; Science 287:1479-82.
Bodhidatta, L., et al. (2002) "Bacterial enteric pathogens in children with acute dysentery in Thailand: increasing importance of quinolone-resistant Campylobacter"; Southeast Asian J Trop Med Public Health 33:752-7.
Brodersen, D. E., et al. (2002) "Crystal structure of the 30 S ribosomal subunit from *Thermus thermophilus*: structure of the proteins and their interactions with 16 S RNA"; J Mol Biol 316:725-68.
Bursavich, M. G. & Rich, D. H. (2002) "Designing Non-Peptide Peptidomimetics in the 21st Century: Inhibitors Targeting Conformational Ensembles"; J. Med. Chem. 45(3):541-558.
Cannone, J. J., et al. (2002) "The Comparative RNA Web (CRW) Site: an online database of comparative sequence and structure information for ribosomal, intron, and other RNAs: Correction"; BMC Bioinformatics 3:15.
Carter, A. P., et al. (2001) "Crystal structure of an initiation factor bound to the 30S ribosomal subunit"; Science 291:498-501.
Carter, A. P., et al. (2000) "Functional insights from the structure of the 30S ribosomal subunit and its interactions with antibiotics"; Nature 407:340-8.
Castagnoli, L., et al. (2001) "Alternative bacteriophage display systems"; Comb Chem High Throughput Screen 4:121-33.
Cha, J., et al. (1993) "New vectors for direct cloning of PCR products"; Gene 136:369-70.
Chopra, I., et al. (2003) "The role of mutators in the emergence of antibiotic-resistant bacteria"; Drug Resist Updat 6:137-45.
Chow, C. S. & Bogdan, F. M. (1997) "A Structural Basis for RNA-Ligand Interactions"; Chem. Rev. 97:1489-1513.
Clarke, S. C., et al. (2003) "Virulence of enteropathogenic *Escherichia coli*, a global pathogen"; Clin Microbiol Rev 16(3):365-78.
Clarke, S. C., et al. (2002) "Enteropathogenic *Escherichia coli* infection: history and clinical aspects"; Br J Biomed Sci 59:123-7.
Collins, M. & Tami, T. A. (2003) "Methicillin-resistant *Staphylococcus aureus* (MRSA) in the practice of otolaryngology—an emerging community acquired organism?"; Curr Opin Otolaryngol Head Neck Surg 11:179-83.
Cunningham, P. R., et al. (1988) "The role of 16S RNA in ribosome function: single base alterations and their effect on in vitro protein synthesis"; Arch Biol Med Exp (Santiago) 21:393-401.
Danner, S. & Belasco, J. G. (2001) "T7 phage display: a novel genetic selection system for cloning RNA-binding proteins from cDNA libraries"; Proc Natl Acad Sci U S A 98:12954-9.
De Stasio, E. A., et al. (1989) "Mutations in 16S ribosomal RNA disrupt antibiotic—RNA interactions"; Embo J 8:1213-6.
Depardieu, F., et al. (2003) "VanD-type vancomycin-resistant *Enterococcus faecium* 10/96A"; Antimicrob Agents Chemother 47:7-18.
Dessen, A., et al. (2001) "Molecular mechanisms of antibiotic resistance in gram-positive pathogens"; Curr Drug Targets Infect Disord 1:63-77.
Enright, M. C. (2003) "The evolution of a resistant pathogen—the case of MRSA"; Curr Opin Pharmacol 3:474-9.
Evans, G. A. (2002) "The Oxazolidinones"; Curr Infect Dis Rep 4:17-27.
Fauci, A. S., et al.; (2005) "Emerging infectious diseases: a 10-year perspective from the national institute of allergy and infectious diseases." Emerg Infect Dis; 11: 519-25.
Fourmy, D., et al. (1996) "Structure of the A site of *Escherichia coli* 16S Ribosomal RNA Complexed with an Aminoglycoside Antibiotic"; Science 274:1367-1371.
Gabashvili, I. S., et al. (1999) "Major rearrangements in the 70S ribosomal 3D structure caused by a conformational switch in 16S ribosomal RNA"; Embo J 18:6501-7.
Gomi, H., et al. (2001) "In vitro antimicrobial susceptibility testing of bacterial enteropathogens causing traveler's diarrhea in four geographic regions"; Antimicrob Agents Chemother 45:212-6.
Gonzales, R. D., et al. (2001) "Infections due to vancomycin-resistant *Enterococcus faecium* resistant to linezolid"; Lancet 357:1179.
Guerrant, R. L., et al. (2002) "Magnitude and impact of diarrheal diseases"; Arch Med Res 33:351-5.
Gutell, R. R., et al. (1992) "Identifying constraints on the higher-order structure of RNA: continued development and application of comparative sequence analysis methods"; Nucleic Acids Res 20(21):5785-95.
Haddad, J., et al. (2002) "Design of Novel Antibiotics that Bind to the Ribosomal Acyltransfer Site"; J. Am. Chem. Soc. 124:3229-3237.
Hancock, R. E. & Chapple, D. S. (1999) "Peptide Antibiotics"; Antimicrob. Agents Chemother. 43(6):1317-1323.
Harms, J., et al. (2001) "High Resolution Structure of the Large Ribosomal Subunit from a Mesophilic Eubacterium"; Cell 107:679-688.
Hartman, A. B., et al. (2003) "Epidemiology of tetracycline resistance determinants in *Shigella* spp. and enteroinvasive *Escherichia coli*: characterization and dissemination of tet(A)-1"; J Clin Microbiol 41:1023-32.
Herrero, I. A., et al. (2002) "Nosocomial spread of linezolid-resistant, vancomycin-resistant *Enterococcus faecium*"; N Engl J Med 346:867-9.

Hwang, S., et al. (1999) "Inhibition of Gene Expression in Human Cells Through Small-Molecule-RNA Interactions"; Proc. Natl. Acad. Sci. USA 96:12997-13002.

John, T. J. (1996) "Emerging & re-emerging bacterial pathogens in India"; Indian J Med Res 103:4-18.

Jones, R. N., et al. (2002) "Linezolid-resistant *Enterococcus faecium* isolated from a patient without prior exposure to an oxazolidinone: report from the SENTRY Antimicrobial Surveillance Program"; Diagn Microbiol Infect Dis 42:137-9.

Keren-Zur, M., et al. (1979) "Localization of the decoding region on the 30S *Escherichia coli* ribosomal subunit by affinity immunoelectron microscopy"; Proc Natl Acad Sci U S A 76:1054-8.

Khan, W. A., et al. (1996) "Randomised controlled comparison of single-dose ciprofloxacin and doxycycline for cholera caused by *Vibrio cholerae* 01 or 0139"; Lancet 348:296-300.

Kieber-Emmons, T., et al. (1997) "Therapeutic Peptides and Peptidomimetics"; Curr Opin. Biotech. 8:435-441.

Kloss, P., et al. (1999) "Resistance mutations in 23 S rRNA identify the site of action of the protein synthesis inhibitor linezolid in the ribosomal peptidyl transferase center"; J Mol Biol 294:93-101.

Klostermeier, D., et al. (2004) "A three-fluorophore FRET assay for high-throughput screening of small-molecule inhibitors of ribosome assembly"; Nucleic Acids Res.; May 17; 32(9); pp. 2707-2715.

Krzyzosiak, W., et al. (1987) "In vitro synthesis of 16S ribosomal RNA containing single base changes and assembly into a functional 30S ribosome"; Biochemistry 26:2353-64.

Lam, K. S., et al. (1995) "Application of a Dual Color Detection Scheme in the Screening of a Random Combinatorial Peptide Library"; J. Immunol. Methods 180:219-223.

Lesley, S. A., et al. (1991) "Use of in vitro protein synthesis from polymerase chain reaction-generated templates to study interaction of *Escherichia coli* transcription factors with core RNA polymerase and for epitope mapping of monoclonal antibodies"; J Biol Chem 266(4): 2632-8.

Levy, S. B., et al. (2004) "Antibacterial resistance worldwide: causes, challenges and responses." Nat Med.; 10:S122-9.

Levy, S. B. (2001) "Antibiotic resistance: consequences of inaction"; Clin Infect Dis 33 Suppl 3:S124-9.

Lin-Goerke, J. L., et al. (1997) "PCR-based random mutagenesis using manganese and reduced dNTP concentration"; Biotechniques 23:409-12.

Lind, K. E., et al. (2002) "Structure-Based Computational Database Screening, In Vitro Assay, and NMR Assessment of Compunds that Target TAR RNA"; Chem. Biol. 9:185-193.

Lindenbaum, J., et al. (1967) "Antibiotic therapy of cholera in children"; Bull World Health Organ 37:529-38.

Llano-Sotelo, B., et al. (2002) "Aminoglycosides Modified by Resistance Enzymes Display Diminished Binding to the Bacterial Ribosomal Acyl-Transfer Site"; Chemistry & Biology 9:455-463.

Lodmell, J. S. & Dahlberg, A. E. (1997) "A conformational switch in *Escherichia coli* 16S ribosomal RNA during decoding of messenger RNA"; Science 277:1262-7.

Lynch, S. R., et al. (2003) "Comparison of X-Ray Crystal Structure of the 30S Subunit-Antibiotic Complex with NMR Structure of Decoding Site Oligonucleotide-Paromomycin Complex"; Structure 11:43-53.

Magnet, S. & Blanchard, J.S. (2005) "Molecular insights into aminoglycoside action and resistance"; Chem Rev; 105:477-98.

McManus, M. C. (1997) "Mechanisms of bacterial resistance to antimicrobial agents"; Am J Health Syst Pharm 54:1420-33; quiz pp. 1444-1446.

Miller, B. T., et al. (1997) "Peptide Biotinylation with Amine-Reactive Esters: Differential Side Chain Reactivity"; Peptides 18:1585-1595.

Mirza, S. H., et al. (1996) "Multi-drug resistant typhoid: a global problem"; J Med Microbiol 44:317-9.

Mucha, P., et al. (2002) "Interaction of RNA with Phage-Display Selected Peptides Analyzed by Capillary Electrophoresis Mobility Shift Assay"; RNA 8:698-704.

Mucha, P., et al. (2001) "Anticodon Domain Methylated Nucleosides of Yeast tRNA Phe are Significant Recognition Determinants in the Building of a Phage Display Selected Peptide"; Biochemistry 40:14191-14199.

Nandi, S., et al. (2004) "Gram-positive bacteria are a major reservoir of Class 1 antibiotic resistance integrons in poultry litter"; Proc Natl Acad Sci U S A 101:7118-22.

Nataro, J. P. & Kaper, J. B. (1998) "Diarrheagenic *Escherichia coli*"; Clin Microbiol Rev 11(1):142-201.

Nikonowicz, E. P., et al. (1992) "Preparation of 13C and 15N labelled RNAs for heteronuclear multi-dimensional NMR studies"; Nucleic Acids Res. 20(17):4507-4513.

Ogle, J. M., et al. (2001) "Recognition of cognate transfer RNA by the 30S ribosomal subunit"; Science 292:897-902.

Oldfield, E. C., 3rd & Wallace, M. R. (2001) "The role of antibiotics in the treatment of infectious diarrhea"; Gastroenterol Clin North Am 30:817-36.

Orr, J. W., et al. (1998) "Protein and Mg(2+)-induced conformational changes in the S15 binding site of 16 S ribosomal RNA"; J. Mol. Biol. 275:453-464.

Papich, M. G. (2003) "Antimicrobial therapy for gastrointestinal diseases"; Vet Clin North Am Equine Pract 19:645-63.

Pelham, H. R. & Jackson, R. J. (1976) "An efficient mRNA-dependent translation system from reticulocyte lysates"; Eur J Biochem 67:247-56.

Peske, F., et al. (2004) "Conformational changes of the small ribosomal subunit during elongation factor G-dependent tRNA-mRNA translocation"; J Mol Biol 343:1183-94.

Pioletti, M., et al. (2001) "Crystal structures of complexes of the small ribosomal subunit with tetracycline, edeine and IF3"; Embo J 20:1829-39.

Prince, J. B., et al. (1982) "Covalent crosslinking of tRNA1Val to 16S RNA at the ribosomal P site: identification of crosslinked residues"; Proc Natl Acad Sci U S A 79:5450-4.

Recht, M. I., et al. (1999) "Effect of mutations in the A site of 16 S rRNA on aminoglycoside antibiotic-ribosome interaction"; J Mol Biol; 286:33-43.

Rodriguez-Correa, D. & Dahlberg, A. E. (2004) "Genetic evidence against the 16S ribosomal RNA helix 27 conformational switch model"; RNA 10:28-33.

Rothman, J. H. & Still, W. C. (1997) "Peptide-Binding Antibiotics: A Solid-Phase Assay for Screening Libraries of Vancomycin Mimics for Selective d-Ala-d-Ala Binding"; Bioorg. Med. Chem. Lett. 7:3159-3164.

Sander, P., et al. (2002) "Ribosomal and non-ribosomal resistance to oxazolidinones: species-specific idiosyncrasy of ribosomal alterations"; Mol Microbiol 46:1295-304.

Serganov, A. A., et al. (1996) "The 16S rRNA binding site of *Thermus thermophilus* ribosomal protein S15: comparison with *Escherichia coli* S15, minimum site and structure"; RNA 2:1124-1138.

Shine, J. & Dalgarno, L. (1974) "The 3'-terminal sequence of *Escherichia coli* 16S ribosomal RNA: complementarity to nonsense triplets and ribosome binding sites"; Proc Natl Acad Sci USA; 71:1342-6.

Sirinavin, S. & Garner, P. (2000) "Antibiotics for treating salmonella gut infections"; Cochrane Database Syst Rev, CD001167.

Tsiodras, S., et al. (2001) "Linezolid resistance in a clinical isolate of *Staphylococcus aureus*"; Lancet 358:207-8.

Vicens, Q. & Westhof, E. (2003) "Crystal structure of geneticin bound to a bacterial 16S ribosomal RNA A site oligonucleotide"; J Mol Biol 326:1175-88.

Vicens, Q. & Westhof, E. (2001) "Crystal Structure of Paromomycin Docked into the Eubacterial Ribosomal Decoding A Site"; Structure 9:647-658.

Vila-Sanjurjo, A., et al. (1999) "Isolation of kasugamycin resistant mutants in the 16 S ribosomal RNA of *Escherichia coli*"; J Mol Biol 293:1-8.

Wallace, C. K., et al. (1968) "Optimal antibiotic therapy in cholera"; Bull World Health Organ 39:239-45.

Wang, Y., et al. (1997) "Specificity of Aminoglycoside Binding to RNA Constructs Derived from the 16S rRNA Decoding Region and the HIV-RRE Activator Region"; Biochemistry 36:768-779.

Wanke, C. A. (2001) "To know *Escherichia coli* is to know bacterial diarrheal disease"; Clin Infect Dis 32:1710-2.

Wilson, K. S. & Noller, H. F. (1998) "Mapping the position of translational elongation factor EF-G in the ribosome by directed hydroxyl radical probing"; Cell 92:131-9.

Wimberly, B. T., et al. (2000) "Structure of the 30S ribosomal subunit"; Nature 407:327-39.

Winkler, F. K., et al. (2001) "Structure-Based Approaches in Modern Drug Discovery Research"; Ernst Schering Res. Found. Workshop 34:123-142.

Xiong, L., et al. (2000) "Oxazolidinone resistance mutations in 23S rRNA of *Escherichia coli* reveal the central region of domain V as the primary site of drug action"; J Bacteriol 182(19):5325-31.

Yoshizawa, S., et al. (1998) "Structural Origins of Gentamicin Antibiotic Action"; EMBO J. 17:6437-6448.

Yusupov, M. M., et al. (2001) "Crystal Structure of the Ribosome at 5.5 Å Resolution"; Science 292:883-896.

Yusupova, G. Z., et al. (2001) "The path of messenger RNA through the ribosome"; Cell 106:233-41.

Zhang, K. & Zhao, H. (2000) "Assessing reliability of gene clusters from gene expression date"; Funct Integr Genomics 1:156-73.

Zhang, X., et al. (2000) "Quinolone antibiotics induce Shiga toxin-encoding bacteriophages, toxin production, and death in mice"; J Infect Dis 181:664-70.

* cited by examiner

| Nucleotide | Description |
|---|---|
| 1-14 & 1499-1536 | 16S rRNA of *Escherichia coli* rrnB operon |
| 15-1498 | 16S rRNA of *Pseudomonas aeruginosa* rrnC operon |
| 1530-1534 | 16S MBS (message binding sequence) GGGAU |
| 1537-1976 | 16S-23S spacer region |
| 1977-4880 | 23S rRNA of *Escherichia coli* rrnB operon |
| 4881-4972 | 23S-5S spacer region |
| 4973-5092 | 5S rRNA of *Escherichia coli* rrnB operon |
| 5096-5139 | terminator T1 of *Escherichia coli* rrnB operon |
| 5271-5299 | terminator T2 of *Escherichia coli* rrnB operon |
| 5436-5474 | cassette |
| 6462-7319 | *bla* (b-lactamase; ampicillin resistance) |
| 7482-8096 | replication origin |
| 8509-8700 | *rop* (Rop protein) |
| 9113-10088 | GFP (Green Fluorescent Protein) |
| 10096-10100 | GFP RBS (ribosome binding sequence) AUCCC |
| 10117-10157 | *trpc* promoter |
| 10632-10672 | *trpc* promoter |
| 10689-10693 | CAT RBS (ribosome binding sequence) AUCCC |
| 10701-11630 | *cam* (chloramphenicol acetyltransferase; CAT) |
| 11670-11747 | *lacIq* promoter |
| 11748-12830 | *lacIq* (lac repressor) |
| 12873-12914 | *lacUV5* promoter |

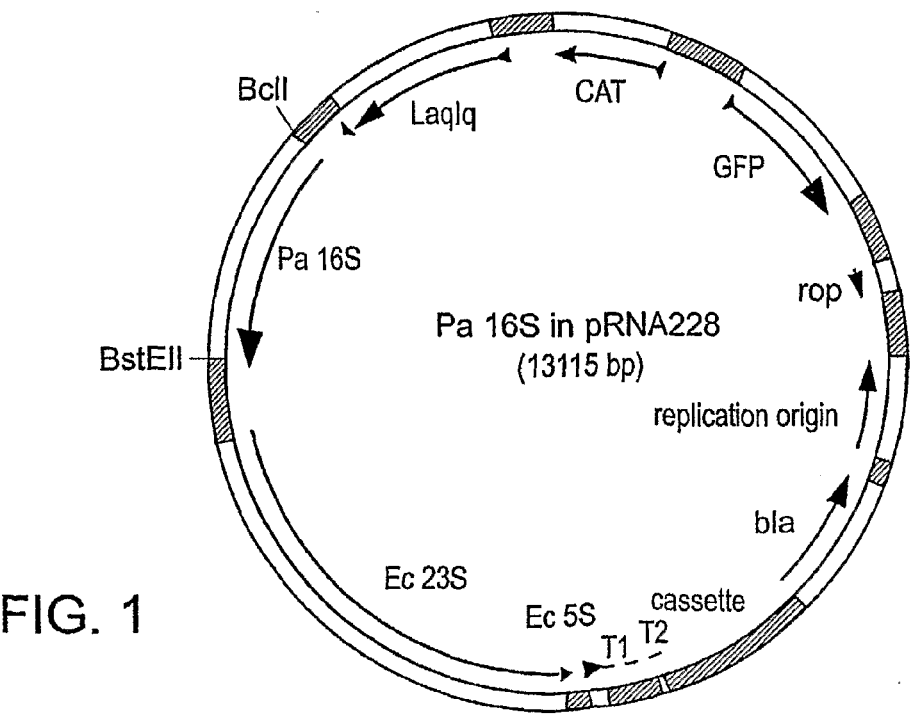

FIG. 1

| Nucleotide | Description |
|---|---|
| 1-14, 176-188 & 1499-1536 | 16S rRNA of *Escherichia coli* rrnB operon |
| 15-175 & 189-1498 | 16S rRNA of *Pseudomonas aeruginosa* rrmC operon |
| 1530-1534 | 16S MBS (message binding sequence) GGGAU |
| 1537-1976 | 16S-23S spacer region |
| 1977-4880 | 23S rRNA of *Escherichia coli* rrnB operon |
| 4881-4972 | 23S-5S spacer region |
| 4973-5092 | 5S rRNA of *Escherichia coli* rrnB operon |
| 5096-5139 | terminator T1 of *Escherichia coli* rrnB operon |
| 5271-5299 | terminator T2 of *Escherichia coli* rrnB operon |
| 5436-5474 | cassette |
| 6462-7319 | *bla* (b-lactamase; ampicillin resistance) |
| 7482-8096 | replication origin |
| 8509-8700 | *rop* (Rop protein) |
| 9113-10088 | GFP (Green Fluorescent Protein) |
| 10096-10100 | GFP RBS (ribosome binding sequence) AUCCC |
| 10117-10157 | *trpc* promoter |
| 10632-10672 | *trpc* promoter |
| 10689-10693 | CAT RBS (ribosome binding sequence) AUCCC |
| 10701-11630 | *cam* (chloramphenicol acetyltransferase; CAT) |
| 11670-11747 | *lacIq* promoter |
| 11748-12830 | *lacIq* (lac repressor) |
| 12873-12914 | *lacUV5* promoter |

FIG. 2A

| FIG. 2A |
|---|
| FIG. 2B |

FIG. 2

| Nucleotide | Description |
|---|---|
| 723-1268 | replication origin |
| 1862-2677 | *aph (3")-la* (kanamycin resistance) |
| 2950-3828 | *araC* |
| 3979-4005 | Pc (araC promoter) |
| 4104-4131 | pBAD promoter |
| 4163-4206 | terminator T1 of *Escherichia coli* rrnB operon |
| 4338-4366 | terminator T2 of *Escherichia coli* rrnB operon |

| Nucleotide | Description |
|---|---|
| 723-1268 | replication origin |
| 1862-2677 | aph (3')-la (kanamycin resistance) |
| 2950-3828 | araC |
| 3979-4005 | Pc (araC promoter) |
| 4104-4131 | pBAD promoter |
| 4168-4172 | Shine-Dalgarnosequence (GAGGA) |
| 4181-4453 | Pseudomonas aeruginosa S20 |
| 4463-4506 | terminator T1 of Escherichia coli rrnB operon |
| 4638-4666 | terminator T2 of Escherichia coli rrnB operon |

Figure 5

| Samples | GFP % |
|---|---|
| LB+Amp+Kan+pRNA228 and pKanPa-S20 | 5.9 |
| LB+Amp+Kan+Pa 16S in pRNA228 and pKanPa-S20 | 2.38 |
| LB+Amp+Kan+pRNA228 and pKan5-T1T2 | 5.82 |
| LB+Amp+Kan+Pa 16S in pRNA228 and pKan5-T1T2 | 1.97 |
| | |
| LB+Amp+Kan+IPTG+pRNA228 and pKanPa-S20 | 83.94 |
| LB+Amp+Kan+IPTG+Pa 16S in pRNA228 and pKanPa-S20 | 41.57 |
| LB+Amp+Kan+IPTG+pRNA228 and pKan5-T1T2 | 115.67 |
| LB+Amp+Kan+IPTG+Pa 16S in pRNA228 and pKan5-T1T2 | 43.05 |
| | |
| LB+Amp+Kan+Arabinose+pRNA228 and pKanPa-S20 | 4.68 |
| LB+Amp+Kan+Arabinose+Pa 16S in pRNA228 and pKanPa-S20 | 4.07 |
| LB+Amp+Kan+Arabinose+pRNA228 and pKan5-T1T2 | 4.89 |
| LB+Amp+Kan+Arabinose+Pa 16S in pRNA228 and pKan5-T1T2 | 1.62 |
| | |
| LB+Amp+Kan+IPTG+Arabinose+pRNA228 and pKanPa-S20 | 100.41 |
| LB+Amp+Kan+IPTG+Arabinose+Pa 16Sin pRNA228 and pKanPa-S20 | 96.85 |
| LB+Amp+Kan+IPTG+Arabinose+pRNA228 and pKan5-T1T2 | 115.8 |
| LB+Amp+Kan+IPTG+Arabinose+Pa 16S in pRNA228 and pKan5-T1T2 | 25.04 |
| | |
| LB+Amp+IPTG+pRNA228 | 111.31 |
| LB+Amp+IPTG+Pa 16S in pRNA228 | 43.55 |
| | |
| LB+Amp+IPTG+Arabinose+pRNA228 | 100 |
| LB+Amp+IPTG+Arabinose+Pa 16S in pRNA228 | 25.02 |

Figure 6a

```
TTACGCCCCGCCCTGCCACTCATCGCAGTACTGTTGTAATTCATTAAGCATTCTGC
CGACATGGAAGCCATCACAGACGGCATGATGAACCTGAATCGCCAGCGGCATCA
GCACCTTGTCGCCTTGCGTATAATATTTGCCCATGGTGAAAACGGGGGCGAAGAA
GTTGTCCATATTGGCCACGTTTAAATCAAAACTGGTGAAACTCACCCAGGGATTG
GCTGAGACGAAAAACATATTCTCAATAAACCCTTTAGGGAAATAGGCCAGGTTTT
CACCGTAACACGCCACATCTTGCGAATATATGTGTAGAAACTGCCGGAAATCGTC
GTGGTATTCACTCCAGAGCGATGAAAACGTTTCAGTTTGCTCATGGAAAACGGTG
TAACAAGGGTGAACACTATCCCATATCACCAGCTCACCGTCTTTCATTGCCATAC
GGAATTCCGGATGAGCATTCATCAGGCGGGCAAGAATGTGAATAAAGGCCGGAT
AAAACTTGTGCTTATTTTCTTTACGGTCTTTAAAAAGGCCGTAATATCCAGCTGA
ACGGTCTGGTTATAGGTACATTGAGCAACTGACTGAAATGCCTCAAAATGTTCTT
TACGATGCCATTGGGATATATCAACGGTGGTATATCCAGTGATTTTTTCTCCATT
TGCGGAGGGATATGAAAGCGGCCGCTTCCACACATTAAACTAGTTCGATGATTA
ATTGTCAACAGCTCGCCGGCGGCACCTCGCTAACGGATTCACCACTCCAAGAATT
GGAGCCAATCGATTCTTGCGGAGAACTGTGAATGCGCAAACCAACCCTTGGCAG
AACATATCCATCGCGTCCGCCATCTCCAGCAGCCGCACGCGGCGCATCTCGGGCA
GCGTTGGGTCCTGGCCACGGGTGCGCATGATCGTGCTCCTGTCGTTGAGGACCCG
GCTAGGCTGGCGGGGTTGCCTTACTGGTTAGCAGAATGAATCACCGATACGCGA
GCGAACGTGAAGCGACTGCTGCTGCAAAACGTCTGCGACCTGAGCAACAACATG
AATGGTCTTCGGTTTCCGTGTTTCGTAAAGTCTGGAAACGCGGAAGTCAGCGCCC
TGCACCATTATGTTCCGGATCTGGGTACCCGCATTCACAGTTCTCCGCAAGAATC
GATTGGCTCCAATTCTTGGAGTGGTGAATCCGTTAGCGAGGTGCCGCCGGCGAGC
TGTTGACAATTAATCATCGAACTAGTTTAATGTGTGGAAGCGGCCGCTTTCATAT
CCCTCCGCAAATGGAGAAAAAATCACTGCTAGCAAAGGAGAAGAACTTTTCAC
TGGAGTTGTCCCAATTCTTGTTGAATTAGATGGTGATGTTAATGGGCACAAATTT
TCTGTCAGTGGAGAGGGTGAAGGTGATGCTACATACGGAAAGCTTACCCTTAAA
TTTATTTGCACTACTGGAAAACTACCTGTTCCATGGCCAACACTTGTCACTACTTT
CTCTTATGGTGTTCAATGCTTTTCCCGTTATCCGGATCATATGAAACGGCATGACT
TTTTCAAGAGTGCCATGCCCGAAGGTTATGTACAGGAACGCACTATATCTTTCAA
AGATGACGGGAACTACAAGACGCGTGCTGAAGTCAAGTTTGAAGGTGATACCCT
TGTTAATCGTATCGAGTTAAAAGGTATTGATTTTAAAGAAGATGGAAACATTCTC
GGACACAAACTCGAGTACAACTATAACTCACACAATGTATACATCACGGCAGAC
AAACAAAAGAATGGAATCAAAGCTAACTTCAAAATTCGCCACAACATTGAAGAT
GGATCCGTTCAACTAGCAGACCATTATCAACAAAATACTCCAATTGGCGATGGCC
CTGTCCTTTTACCAGACAACCATTACCTGTCGACACAATCTGCCCTTTCGAAAGA
TCCCAACGAAAGCGTGACCACATGGTCCTTCTTGAGTTTGTAACTGCTGCTGGG
ATTACACATGGCATGGATGAGCTCTACAAATAATCTAGTCGTAGCGCCGATGGTA
GTGTGGGGTCTCCCCATGCGAGAGTAGGGAACTGCCAGGCATCAAATAAAACGA
AAGGCTCAGTCGAAAGACTGGGCCTTTCGTTTTATCTGTTGTTTGTCGGTGAACG
CTCTCCTGAGTAGGACAAATCCGCCGGGAGCGGATTTGAACGTTGCGAAGCAAC
GGCCCGGAGGGTGGCGGGCAGGACGCCCGCCATAAACTGCCAGGCATCAAATTA
AGCAGAAGGCCATCCTGACGGATGGCCTTTTGCGTTTCTACAAACTCTTCCTGT
CGTCAGTGCAGGTACCGAGCTCGAATTCACTGGCCGTCGTTTTACAACGTCGTGA
CTGGGAAAACCCTGGCGTTACCCAACTTAATCGCCTTGCAGCACATCCCCCTTTC
GCCAGGCATCGCAGGATGCTGCTGGCTACCCT
```

Figure 6b

```
GTGGAACACCTACATCTGTATTAACGAAGCGCTGGCATTGACCCTGAGTGATTTT
TCTCTGGTCCCGCCGCATCCATACCGCCAGTTGTTTACCCTCACAACGTTCCAGTA
ACCGGGCATGTTCATCATCAGTAACCCGTATCGTGAGCATCCTCTCTCGTTTCATC
GGTATCATTACCCCCATGAACAGAAATTCCCCCTTACACGGAGGCATCAAGTGAC
CAAACAGGAAAAAACCGCCCTTAACATGGCCCGCTTTATCAGAAGCCAGACATT
AACGCTTCTGGAGAAACTCAACGAGCTGGACGCGGATGAACAGGCAGACATCTG
TGAATCGCTTCACGACCACGCTGATGAGCTTTACCGCAGCTGCCTCGCGCGTTTC
GGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGT
GTTGGCGGGTGTCGGGCGCAGCCATGACCCAGTCACGTAGCGATAGCGGAGTG
TATACTGGCTTAACTATGCGGCATCAGAGCAGATTGTACTGAGAGTGCACCATAT
GCGGTGTGAAATACCGCACAGATGCGTAAGGAGAAAATACCGCATCAGGCGCTC
TTCCGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATCACAAA
AATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCT
AACTACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAGGATCT
CAAGAAGATCCTTTGATCTTTTCTACGGGGTCTGACGCTCAGTGGAACGAAAACT
CACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGA
GGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCTGCAGG
CATCGTGGTGTCACGCTCGTCGTTTGGTATGGCTTCATTCAGCTCCGGTTCCCAAC
GATCAAGGCGAGTTACATGATCCCCATGTTGTGCAAAAAAGCGGTTAGCTCCTT
CGGTCCTCCGATCGTTGTCAGAAGTAAGTTGGCCGCAGTGTTATCACTCATGGTT
ATGGCAGCACTGCATAATTCTCTTACTGTCATGCCATCCGTAAGATGCTTTTCTGT
GACTGGTGAGTACTCAACCAAGTCATTCTGAGAATAGTGTATGCGGCGACCGAG
TTGCTCTTGCCCGGCGTCAACACGGGATAATACCGCGCCACATAGCAGAACTTTA
AAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGC
ATCTTTTACTTTCACCAGCGTTTCTGGGTGAGCAAAAACAGGAAGGCAAAATGCC
GCAAAAAAGGGAATAAGGGCGACACGGAA
```

Figure 6c

```
ATGTTGAATACTCATACTCTTCCTTTTTCAATATTATTGAAGCATTTATCAGGGTT
ATTGTCTCATGAGCGGATACATATTTGAATGTATTTAGAAAAATAAACAAATAGG
GGTTCCGCGCACATTTCCCCGAAAAGTGCCACCTGACGTCTAAGAAACCATTATT
ATCATGACATTAACCTATAAAAATAGGCGTATCACGAGGCCCTTTCGTCTTCAAG
AATTCTCATGTTTGACAGCTTATCATCGATAAGCTTTAATGCGGTAGTTTATCACA
GTTAAATTGCTAACGCAGTCAGGCACCGTGTATGAAATCTAACAATGCGCTCATC
GTCATCCTCGGCACCGTCACCCTGGATGCTGTAGGCATAGGCTTGGTTATGCCGG
TACTGCCGGGCCTCTTGCGGGATATCGTCCATTCCGACAGCATCGCCAGTCACTA
TGGCGTGCTGCTAGCGCTATATGCGTTGATGCAATTTCTATGCGCACCCGTTCTCG
GAGCACTGTCCGACCGCTTTGGCCGCCGCCCAGTCCTGCTCGCTTCGCTACTTGG
AGCCACTATCGACTACGCGATCATGGCGACCACACCCGTCCTGTGGATCCCAGAC
GAGTTAAGTCACCATACGTTAGTACAGGTTGCCACTCTTTTGGCAGACGCAGACC
TACGGCTACAATAGCGAAGCGGTCCTGGTATTCATGTTTAAAAATACTGTCGCGA
TAGCCAAAACGGCACTCTTTGGCAGTTAAGCGCACTTGCTTGCCTGTCGCCAGTT
CAACAGAATCAACATAAGCGCAAACTCGCTGTAATTCTACGCCATAAGCACCAA
TATTCTGGATAGGTGATGAGCCGACACAACCAGGAATTAATGCCAGATTTTCCAG
ACCAGGCATACCTTCCTGCAAAGTGTATTTTACCAGACGATGCCAGTTTTCTCCG
GCTCCTACATGTAAATACCACGCATCAGGTTCATCATGAATTTCGATACCTTTGA
TCCGGTTGATGATCCCTGCAGGCCCTTAAGGCCATTTAAATGGCGCGCCGATCAA
TGCCAAATGTGTTCCAGGGTTTTAAGGAGTGGTTCATAGCTGCTTTCCTGATGCA
AAAACGAGGCTAGTTTACCGTATCTGTGGGGGGATGGCTTGTAGATATGACGAC
AGGAAGAGTTTGTAGAAACGCAAAAAGGCCATCCGTCAGGATGGCCTTCTGCTT
AATTTGATGCCTGGCAGTTTATGGCGGGCGTCCTGCCCGCCACCCTCCGGGCCGT
TGCTTCGCAACGTTCAAATCCGCTCCCGGCGGATTTGTCCTACTCAGGAGAGCGT
TCACCGACAAACAACAGATAAAACGAAAGGCCCAGTCTTTCGACTGAGCCTTTC
GTTTTATTTGATGCCTGGCAGTTCCCTACTCTCGCATGGGGAGACCCCACACTAC
CATCGGCGCTACGGCGTTTCACTTCTGAGTTCGGCATGGGGTCAGGTGGGACCAC
CGCGCTACTGCCGCCAGGCAAATTCTGTTTTATCAGACCGCTTCTGCGTTCTGATT
TAATCTGTATCAGGCTGAAAATCTTCTCTCATCCGCCAAAACAGCTTCGGCGTTG
TAAGGTTAAGCCTCACGGTTCATTAGTACCGGTTAGCTCAACGCATCGCTGCGCT
TACACACCCGGCCTATCAACGTCGTCGTCTTCAACGTTCCTTCAGGACCCTTAAA
GGGTCAGGGAGAACTCATCTCGGGGCAAGTTTCGTGCTTAGATGCTTTCAGCACT
TATCTCTTCCGCATTTAGCTACCGGGCAGTGCCATTGGCATGACAACCCGAACAC
CAGTGATGCGTCCACTCCGGTCCTCTCGTACTAGGAGCAGCCCCCCTCAGTTCTC
CAGCGCCCACGGCAGATAGGGACCGAACTGTCTCACGACGTTCTAAACCCAGCT
CGCGTACCACTTTAAATGGCGAACAGCCATACCCTTGGGACCTACTTCAGCCCCA
GGATGTGATGAGCCGACATCGAGGTGCCAAACACCGCCGTCGATATGAACTCTT
GGGCGGTATCAGCCTGTTATCCCCGGAGTACCTTTATCCGTTGAGCGATGGCCC
TTCCATTCAGAACCACCGGATCACTATGACCTGCTTTCGCACCTGCTCGCGCCGT
CACGCTCGCAGTCAAGCTGGCTTATGCCATTGCACTAACCTCCTGATGTCCGACC
AGGATTAGCCAACCTTCGTGCTCCTCCGTTACTCTTTAGGAGGAGACCGCCCAG
TCAAACTACCCACCAGACACTGTCCGCAACCCGGATTACGGGTCAACGTTAGAA
CATCAAACATTAAAGGGTGGTATTTCAAGGTCGGCTCCATGCAGACTGGCGTCCA
CACTTCAAAGCCTCCCACCTATCCTACACATCAAGGCTAATGTTCAGTGTCAAG
CTATAGTAAAGGTTCACGGGGTCTTTCCGTCTTGCCG
```

Figure 6d

```
CGGGTACACTGCATCTTCACAGCGAGTTCAATTTCACTGAGTCTCGGGTGGAGAC
AGCCTGGCCATCATTACGCCATTCGTGCAGGTCGGAACTTACCCGACAAGGAATT
TCGCTACCTTAGGACCGTTATAGTTACGGCCGCCGTTTACCGGGGCTTCGATCAA
GAGCTTCGCTTGCGCTAACCCCATCAATTAACCTTCCGGCACCGGGCAGGCGTCA
CACCGTATACGTCCACTTTCGTGTTTGCACAGTGCTGTGTTTTAATAAACAGTTG
CAGCCAGCTGGTATCTTCGACTGATTTCAGCTCCATCCGCGAGGGACCTCACCTA
CATATCAGCGTGCCTTCTCCCGAAGTTACGGCACCATTTTGCCTAGTTCCTTCACC
CGAGTTCTCTCAAGCGCCTTGGTATTCTCTACCTGACCACCTGTGTCGGTTTGGGG
TACGATTTGATGTTACCTGATGCTTAGAGGCTTTTCCTGGAAGCAGGGCATTTGTT
GCTTCAGCACCGTAGTGCCTCGTCATCACGCCTCAGCCTTGATTTTCCGGATTTGC
CTGGAAAACCAGCCTACACGCTTAAACCGGGACAACCGTCGCCCGGCCAACATA
GCCTTCTCCGTCCCCCTTCGCAGTAACACCAAGTACAGGAATATTAACCTGTTT
CCCATCGACTACGCCTTTCGGCCTCGCCTTAGGGGTCGACTCACCCTGCCCCGAT
TAACGTTGGACAGGAACCCTTGGTCTTCCGGCGAGCGGGCTTTTCACCCGCTTTA
TCGTTACTTATGTCAGCATTCGCACTTCTGATACCTCCAGCATGCCTCACAGCACA
CCTTCGCAGGCTTACAGAACGCTCCCCTACCCAACAACGCATAAGCGTCGCTGCC
GCAGCTTCGGTGCATGGTTTAGCCCCGTTACATCTTCCGCGCAGGCCGACTCGAC
CAGTGAGCTATTACGCTTTCTTTAAATGATGGCTGCTTCTAAGCCAACATCCTGG
CTGTCTGGGCCTTCCCACATCGTTTCCCACTTAACCATGACTTGGGACCTTAGCT
GGCGGTCTGGGTTGTTTCCCTCTTCACGACGGACGTTAGCACCCGCCGTGTGTCT
CCCGTGATAACATTCTCCGGTATTCGCAGTTTGCATCGGGTTGGTAAGTCGGGAT
GACCCCCTTGCCGAAACAGTGCTCTACCCCGGAGATGAATTCACGAGGCGCTAC
CTAAATAGCTTTCGGGGAGAACCAGCTATCTCCCGGTTTGATTGGCCTTTCACCC
CCAGCCACAAGTCATCCGCTAATTTTTCAACATTAGTCGGTTCGGTCCTCCAGTTA
GTGTTACCCAACCTTCAACCTGCCCATGGCTAGATCACCGGGTTTCGGGTCTATA
CCCTGCAACTTAACGCCCAGTTAAGACTCGGTTTCCCTTCGGCTCCCCTATTCGGT
TAACCTTGCTACAGAATATAAGTCGCTGACCCATTATACAAAAGGTACGCAGTCA
CACGCCTAAGCGTGCTCCCACTGCTTGTACGTACACGGTTTCAGGTTCTTTTTCAC
TCCCCTCGCCGGGGTTCTTTTCGCCTTTCCCTCACGGTACTGGTTCACTATCGGTC
AGTCAGGAGTATTTAGCCTTGGAGGATGGTCCCCCCATATTCAGACAGGATACCA
CGTGTCCCGCCCTACTCATCGAGCTCACAGCATGTGCATTTTGTGTACGGGCT
GTCACCCTGTATCGCGCGCCTTTCCAGACGCTTCCACTAACACACACTGATTC
AGGCTCTGGGCTGCTCCCCGTTCGCTCGCCGCTACTGGGGAATCTCGGTTGATT
TCTTTTCCTCGGGGTACTTAGATGTTTCAGTTCCCCCGGTTCGCCTCATTAACCTA
TGGATTCAGTTAATGATAGTGTGTCGAAACACACTGGGTTTCCCCATTCGGAAAT
CGCCGGTTATAACGGTTCATATCACCTTACCGACGCTTATCGCAGATTAGCACGT
CCTTCATCGCCTCTGACTGCCAGGGCATCCACCGTGTACGCTTAGTCGCTTAACCT
CACAACCCGAAGATGTTTCTTTCGATTCATCATCGTGTTGCGAAAATTTGAGAGA
CTCACGAACAACTCTCGTTGTTCAGTGTTTCAATTTTCAGCTTGATCCAGATTTTT
AAAGAGCAAATATCTCAAACATCACCCGAAGATGAGTTTTGAGATATTAAGGTC
GGCGACTTTCACTCACAAACCAGCAAGTGGCGTCCCCTAGGGGATTCGAACCCCT
GTTACCGCCGTGAAAGGGCGGTGTCCTGGGCCTCTAGACGAAGGGGACACGAAA
ATTGCTTATCACGCGTTGCGTGATATTTCGTGTAGGGTGAGCTTTCATTAATAGA
AAGCGAACGGCCTTATTCTCTTCAGCCTCACTCCCAACGCGTAAACGCCTTGCTT
TTCACTTTCTATCAGACAATCTGTGTGAGCACTAC
```

Figure 6e

AAAGTACGCTTCTTTAAGGTAATCCCATGATCCAACCGCAGGTTCCCCTACGGTT
ACcTTGTTACGACTTCACCCCAGTCATGAATCACTCCGTGGTAACCGTCCCCCTTG
CGGTTAGACTAGCTACTTCTGGAGCAACCCACTCCCATGGTGTGACGGGCGGTGT
GTACAAGGCCCGGGAACGTATTCACCGTGACATTCTGATTCACGATTACTAGCGA
TTCCGACTTCACGCAGTCGAGTTGCAGACTGCGATCCGGACTACGATCGGTTTTA
TGGGATTAGCTCCACCTCGCGGCTTGGCAACCCTTTGTACCGACCATTGTAGCAC
GTGTGTAGCCCTGGCCGTAAGGGCCATGATGACTTGACGTCATCCCCACCTTCCT
CCGGTTTGTCACCGGCAGTCTCCTTAGAGTGCCCACCCGAGGTGCTGGTAACTAA
GGACAAGGGTTGCGCTCGTTACGGGACTTAACCCAACATCTCACGACACGAGCT
GACGACAGCCATGCAGCACCTGTGTCTGAGTTCCCGAAGGCACCAATCCATCTCT
GGAAAGTTCTCAGCATGTCAAGGCCAGGTAAGGTTCTTCGCGTTGCTTCGAATTA
AACCACATGCTCCACCGCTTGTGCGGGCCCCCGTCAATTCATTTGAGTTTTAACCT
TGCGGCCGTACTCCCCAGGCGGTCGACTTATCGCGTTAGCTGCGCCACTAAGATC
TCAAGGATCCCAACGGCTAGTCGACATCGTTTACGGCGTGGACTACCAGGGTATC
TAATCCTGTTTGCTCCCCACGCTTTCGCACCTCAGTGTCAGTATCAGTCCAGGTGG
TCGCCTTCGCCACTGGTGTTCCTTCCTATATCTACGCATTTCACCGCTACACGGA
AATTCCACCACCCTCTACCGTACTCTAGCTCAGTAGTTTTGGATGCAGTTCCCAG
GTTGAGCCCGGGGATTTCACATCCAACTTGCTGAACCACCTACGCGCGCTTTACG
CCCAGTAATTCCGATTAACGCTTGCACCCTTCGTATTACCGCGGCTGCTGGCACG
AAGTTAGCCGGTGCTTATTCTGTTGGTAACGTCAAAACAGCAAGGTATTAACTTA
CTGCCCTTCCTCCCAACTTAAAGTGCTTTACAATCCGAAGACCTTCTTCACACACG
CGGCATGGCTGGATCAGGCTTTCGCCCATTGTCCAATATTCCCCACTGCTGCCTCC
CGTAGGAGTCTGGACCGTGTCTCAGTTCCAGTGTGACTGATCATCCTCTCAGACC
AGTTACGGATCGTCGCCTTGGTAGGCCTTTACCCCACCAACTAGCTAATCCGACC
TAGGCTCATCTGATAGCGTGAGGTCCGAAGATCCCCCACTTTCTCCCTCAGGACG
TATGCGGTATTAGCGCCCGTTTCCGGACGTTATCCCCCACTACCAGGCAGATTCC
TAGGCATTACTCACCCGTCCGCCGCTGAATCCAGGAGCAAGCTCCCTTCATCCGC
TCGACTTGCATGTGTTAGGCCTGCCGCCAGCGTTCAATCTGAGCCATGATCAAAC
TCTTCAATTTAAAAGTTTGACGCTCAAAGAATTAAACTTCGTAATGAATTACGTG
TTCACTCTTGAGACTTGGTATTCATTTTTCGTCTTGCGACGTTAAGAATCCGTATC
TTCGAGTGCCCACACAGATTGTCTGATAAATTGTTAAAGAGCAGTGCCGCTTCGC
TTTTTCTCAGCGGCCGCTGTGTGAAATTGTTATCCGCTCACAATTCCACACATTAT
ACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGC
CAGCTGCATTAATGAATCGGCCAACGCGCGGGGAGAGGCGGTTTGCGTATTGGG
CGCCAGGGTGGTTTTTCTTTTCACCAGTGAGACGGGCAACAGCTGATTGCCCTTC
ACCGCCTGGCCCTGAGAGAGTTGCAGCAAGCGGTCCACGCTGGTTTGCCCCAGC
AGGCGAAAATCCTGTTTGATGGTGGTTGACGGCGGGATATAACATGAGCTGTCTT
CGGTATCGTCGTATCCCACTACCGAGATATCCGCACCAACGCGCAGCCCGGACTC
GGTAATGGCGCGCATTGCGCCCAGCGCCATCTGATCGTTGGCAACCAGCATCGCA
GTGGGAACGATGCCCTCATTCAGCATTTGCATGGTTTGTTGAAAACCGGACATGG
CACTCCAGTCGCCTTCCCGTTCCGCTATCGGCTGAATTTGATTGCGAGTGAGATA
TTTATGCCAGCCAGCCAGACGCAGACGCGCCGAGACAGAACTTAATGGGCCCGC
TAACAGCGCGATTTGCTGGTGBCCCAATGCGACCAGATGCTCCACGCCCAGTCGC
GTACCGTCTTCATGGGAGAAAATAATACT

Figure 6f

```
GTTGATGGGTGTCTGGTCAGAGACATCAAGAAATAACGCCGGAACATTAGTGCA
GGCAGCTTCCACAGCAATGGCATCCTGGTCATCCAGCGGATAGTTAATAATCAGC
CCACTGACCCGTTGCGCGAGAAGATTGTGCACCGCCGCTTTACAGGCTTCGACGC
CGCTTCGTTCTACCATCGACACCACCACGCTGGCACCCAGTTGATCGGCGCGAGA
TTTAATCGCCGCGACAATTTGCGACGGCGCGTGCAGGGCCAGACTGGAGGTGGC
AACGCCAATCAGCAACGACTGTTTGCCCGCCAGTTGTTGTGCCACGCGGTTGGGA
ATGTAATTCAGCTCCGCCATCGCCGCTTCCACTTTTTCCCGCGTTTTCGCAGAAAC
GTGGCTGGCCTGGTTCACCACGCGGGAAACGGTCTGATAAGAGACACCGGCATA
CTCTGCGACATCGTATAACGTTACTGGTTTCACATTCACCACCCTGAATTGACTCT
CTTCCGGGCGCTATCATGCCATACCGCGAAAGGTTTTGCACCATTCGATGGTGTC
GGATCCTCTAGCCGGACCCACTTGCGGCCACGATCCGTCCGCCGTAAGGCTCATA
CCGTTAATTATTCCCCCCACGGGAGACCTGAGCAAACTGCCCTCAGGCATTTGA
GAAGCACAGGGTCACACTGCTTCGGGTAGTCAATAAACCGGTAAACCAGCAATA
GACATAAGCGGCTATTTAACGACCCTGCCCTGAACCGACGACCGGGTCGAATTTG
CTTTCGAATTTCTGCCATTCATCCGCTTATTATCACTTATTCAGGCGTAGCACCAG
GCGTTTAAGGGCACCAATAACTGCCTTAAAAAAA
```

Figure 7a

TTACGCCCCGCCCTGCCACTCATCGCAGTACTGTTGTAATTCATTAAGCATTCTGC
CGACATGGAAGCCATCACAGACGGCATGATGAACCTGAATCGCCAGCGGCATCA
GCACCTTGTCGCCTTGCGTATAATATTTGCCCATGGTGAAAACGGGGGCGAAGAA
GTTGTCCATATTGGCCACGTTTAAATCAAAACTGGTGAAACTCACCCAGGGATTG
GCTGAGACGAAAAACATATTCTCAATAAACCCTTTAGGGAAATAGGCCAGGTTTT
CACCGTAACACGCCACATCTTGCGAATATATGTGTAGAAACTGCCGGAAATCGTC
GTGGTATTCACTCCAGAGCGATGAAAACGTTTCAGTTTGCTCATGGAAAACGGTG
TAACAAGGGTGAACACTATCCCATATCACCAGCTCACCGTCTTTCATTGCCATAC
GGAATTCCGGATGAGCATTCATCAGGCGGGCAAGAATGTGAATAAAGGCCGGAT
AAAACTTGTGCTTATTTTTCTTTACGGTCTTTAAAAAGGCCGTAATATCCAGCTGA
ACGGTCTGGTTATAGGTACATTGAGCAACTGACTGAAATGCCTCAAAATGTTCTT
TACGATGCCATTGGGATATATCAACGGTGGTATATCCAGTGATTTTTTTCTCCATT
TGCGGAGGGATATGAAAGCGGCCGCTTCCACACATTAAACTAGTTCGATGATTA
ATTGTCAACAGCTCGCCGGCGGCACCTCGCTAACGGATTCACCACTCCAAGAATT
GGAGCCAATCGATTCTTGCGGAGAACTGTGAATGCGCAAACCAACCCTTGGCAG
AACATATCCATCGCGTCCGCCATCTCCAGCAGCCGCACGCGGCGCATCTCGGGCA
GCGTTGGGTCCTGGCCACGGGTGCGCATGATCGTGCTCCTGTCGTTGAGGACCCG
GCTAGGCTGGCGGGGTTGCCTTACTGGTTAGCAGAATGAATCACCGATACGCGA
GCGAACGTGAAGCGACTGCTGCTGCAAACGTCTGCGACCTGAGCAACAACATG
AATGGTCTTCGGTTTCCGTGTTTCGTAAAGTCTGGAAACGCGGAAGTCAGCGCCC
TGCACCATTATGTTCCGGATCTGGGTACCCGCATTCACAGTTCTCCGCAAGAATC
GATTGGCTCCAATTCTTGGAGTGGTGAATCCGTTAGCGAGGTGCCGCCGGCGAGC
TGTTGACAATTAATCATCGAACTAGTTTAATGTGTGGAAGCGGCCGCTTTCATAT
CCCTCCGCAAATGGAGAAAAAAATCACTGCTAGCAAAGGAGAAGAACTTTTCAC
TGGAGTTGTCCCAATTCTTGTTGAATTAGATGGTGATGTTAATGGGCACAAATTT
TCTGTCAGTGGAGAGGGTGAAGGTGATGCTACATACGGAAAGCTTACCCTTAAA
TTTATTTGCACTACTGGAAAACTACCTGTTCCATGGCCAACACTTGTCACTACTTT
CTCTTATGGTGTTCAATGCTTTTCCCGTTATCCGGATCATATGAAACGGCATGACT
TTTTCAAGAGTGCCATGCCCGAAGGTTATGTACAGGAACGCACTATATCTTTCAA
AGATGACGGGAACTACAAGACGCGTGCTGAAGTCAAGTTTGAAGGTGATACCCT
TGTTAATCGTATCGAGTTAAAAGGTATTGATTTTAAAGAAGATGGAAACATTCTC
GGACACAAACTCGAGTACAACTATAACTCACACAATGTATACATCACGGCAGAC
AAACAAAAGAATGGAATCAAAGCTAACTTCAAAATTCGCCACAACATTGAAGAT
GGATCCGTTCAACTAGCAGACCATTATCAACAAAATACTCCAATTGGCGATGGCC
CTGTCCTTTTACCAGACAACCATTACCTGTCGACACAATCTGCCCTTTCGAAAGA
TCCCAACGAAAAGCGTGACCACATGGTCCTTCTTGAGTTTGTAACTGCTGCTGGG
ATTACACATGGCATGGATGAGCTCTACAAATAATCTAGTCGTAGCGCCGATGGTA
GTGTGGGGTCTCCCCATGCGAGAGTAGGGAACTGCCAGGCATCAAATAAAACGA
AAGGCTCAGTCGAAAGACTGGGCCTTTCGTTTTATCTGTTGTTTGTCGGTGAACG
CTCTCCTGAGTAGGACAAATCCGCCGGGAGCGGATTTGAACGTTGCGAAGCAAC
GGCCCGGAGGGTGGCGGGCAGGACGCCCGCCATAAACTGCCAGGCATCAAATTA
AGCAGAAGGCCATCCTGACGGATGGCCTTTTTGCGTTTCTACAAACTCTTCCTGT
CGTCAGTGCAGGTACCGAGCTCGAATTCACTGGCCGTCGTTTTACAACGTCGTGA
CTGGGAAAACCCTGGCGTTACCCAACTTAATCGCCTTGCAGCACATCCCCCTTTC
GCCAGGCATCGCAGGATGCTGCTGGCTACCCT

Figure 7b

```
GTGGAACACCTACATCTGTATTAACGAAGCGCTGGCATTGACCCTGAGTGATTTT
TCTCTGGTCCCGCCGCATCCATACCGCCAGTTGTTTACCCTCACAACGTTCCAGTA
ACCGGGCATGTTCATCATCAGTAACCCGTATCGTGAGCATCCTCTCTCGTTTCATC
GGTATCATTACCCCCATGAACAGAAATTCCCCCTTACACGGAGGCATCAAGTGAC
CAAACAGGAAAAAACCGCCCTTAACATGGCCCGCTTTATCAGAAGCCAGACATT
AACGCTTCTGGAGAAACTCAACGAGCTGGACGCGGATGAACAGGCAGACATCTG
TGAATCGCTTCACGACCACGCTGATGAGCTTTACCGCAGCTGCCTCGCGCGTTTC
GGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGT
GTTGGCGGGTGTCGGGGCGCAGCCATGACCCAGTCACGTAGCGATAGCGGAGTG
TATACTGGCTTAACTATGCGGCATCAGAGCAGATTGTACTGAGAGTGCACCATAT
GCGGTGTGAAATACCGCACAGATGCGTAAGGAGAAAATACCGCATCAGGCGCTC
TTCCGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAA
GGCCGCGTTGCTGGCGTTTTTCCATAGGCTCCGCCCCCTGACGAGCATCACAAA
AATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCT
AACTACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCGCTGG
TAGCGGTGGTTTTTTGTTTGCAAGCAGCAGATTACGCGCAGAAAAAAAGGATCT
CAAGAAGATCCTTTGATCTTTTCTACGGGGTCTGACGCTCAGTGGAACGAAAACT
CACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGA
GGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCTGCAGG
CATCGTGGTGTCACGCTCGTCGTTTGGTATGGCTTCATTCAGCTCCGGTTCCCAAC
GATCAAGGCGAGTTACATGATCCCCATGTTGTGCAAAAAAGCGGTTAGCTCCTT
CGGTCCTCCGATCGTTGTCAGAAGTAAGTTGGCCGCAGTGTTATCACTCATGGTT
ATGGCAGCACTGCATAATTCTCTTACTGTCATGCCATCCGTAAGATGCTTTTCTGT
GACTGGTGAGTACTCAACCAAGTCATTCTGAGAATAGTGTATGCGGCGACCGAG
TTGCTCTTGCCCGGCGTCAACACGGGATAATACCGCGCCACATAGCAGAACTTTA
AAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGC
ATCTTTTACTTTCACCAGCGTTTCTGGGTGAGCAAAAACAGGAAGGCAAAATGCC
GCAAAAAAGGGAATAAGGGCGACACGGAA
```

Figure 7c

ATGTTGAATACTCATACTCTTCCTTTTTCAATATTATTGAAGCATTTATCAGGGTT
ATTGTCTCATGAGCGGATACATATTTGAATGTATTTAGAAAAATAAACAAATAGG
GGTTCCGCGCACATTTCCCCGAAAAGTGCCACCTGACGTCTAAGAAACCATTATT
ATCATGACATTAACCTATAAAAATAGGCGTATCACGAGGCCCTTTCGTCTTCAAG
AATTCTCATGTTTGACAGCTTATCATCGATAAGCTTAATGCGGTAGTTTATCACA
GTTAAATTGCTAACGCAGTCAGGCACCGTGTATGAAATCTAACAATGCGCTCATC
GTCATCCTCGGCACCGTCACCCTGGATGCTGTAGGCATAGGCTTGGTTATGCCGG
TACTGCCGGGCCTCTTGCGGGATATCGTCCATTCCGACAGCATCGCCAGTCACTA
TGGCGTGCTGCTAGCGCTATATGCGTTGATGCAATTTCTATGCGCACCCGTTCTCG
GAGCACTGTCCGACCGCTTGGCCGCCGCCCAGTCCTGCTCGCTTCGCTACTTGG
AGCCACTATCGACTACGCGATCATGGCGACCACACCCGTCCTGTGGATCCCAGAC
GAGTTAAGTCACCATACGTTAGTACAGGTTGCCACTCTTTTGGCAGACGCAGACC
TACGGCTACAATAGCGAAGCGGTCCTGGTATTCATGTTTAAAAATACTGTCGCGA
TAGCCAAAACGGCACTCTTTGGCAGTTAAGCGCACTTGCTTGCCTGTCGCCAGTT
CAACAGAATCAACATAAGCGCAAACTCGCTGTAATTCTACGCCATAAGCACCAA
TATTCTGGATAGGTGATGAGCCGACACAACCAGGAATTAATGCCAGATTTTCCAG
ACCAGGCATACCTTCCTGCAAAGTGTATTTTACCAGACGATGCCAGTTTTCTCCG
GCTCCTACATGTAAATACCACGCATCAGGTTCATCATGAATTTCGATACCTTTGA
TCCGGTTGATGATCCCTGCAGGCCCTTAAGGCCATTTAAATGGCGCGCCGATCAA
TGCCAAATGTGTTCCAGGGTTTTAAGGAGTGGTTCATAGCTGCTTTCCTGATGCA
AAAACGAGGCTAGTTTACCGTATCTGTGGGGGATGGCTTGTAGATATGACGAC
AGGAAGAGTTTGTAGAAACGCAAAAAGGCCATCCGTCAGGATGGCCTTCTGCTT
AATTTGATGCCTGGCAGTTTATGGCGGGCGTCCTGCCCGCCACCCTCCGGGCCGT
TGCTTCGCAACGTTCAAATCCGCTCCCGGCGGATTTGTCCTACTCAGGAGAGCGT
TCACCGACAAACAACAGATAAAACGAAAGGCCCAGTCTTTCGACTGAGCCTTTC
GTTTTATTTGATGCCTGGCAGTTCCCTACTCTCGCATGGGGAGACCCCACACTAC
CATCGGCGCTACGGCGTTTCACTTCTGAGTTCGGCATGGGGTCAGGTGGGACCAC
CGCGCTACTGCCGCCAGGCAAATTCTGTTTTATCAGACCGCTTCTGCGTTCTGATT
TAATCTGTATCAGGCTGAAAATCTTCTCTCATCCGCCAAAACAGCTTCGGCGTTG
TAAGGTTAAGCCTCACGGTTCATTAGTACCGGTTAGCTCAACGCATCGCTGCGCT
TACACACCCGGCCTATCAACGTCGTCGTCTTCAACGTTCCTTCAGGACCCTTAAA
GGGTCAGGGAGAACTCATCTCGGGGCAAGTTTCGTGCTTAGATGCTTTCAGCACT
TATCTCTTCCGCATTTAGCTACCGGGCAGTGCCATTGGCATGACAACCCGAACAC
CAGTGATGCGTCCACTCCGGTCCTCTCGTACTAGGAGCAGCCCCCCTCAGTTCTC
CAGCGCCCACGGCAGATAGGGACCGAACTGTCTCACGACGTTCTAAACCCAGCT
CGCGTACCACTTTAAATGGCGAACAGCCATACCCTTGGGACCTACTTCAGCCCCA
GGATGTGATGAGCCGACATCGAGGTGCCAAACACCGCCGTCGATATGAACTCTT
GGGCGGTATCAGCCTGTTATCCCCGGAGTACCTTTTATCCGTTGAGCGATGGCCC
TTCCATTCAGAACCACCGGATCACTATGACCTGCTTTCGCACCTGCTCGCGCCGT
CACGCTCGCAGTCAAGCTGGCTTATGCCATTGCACTAACCTCCTGATGTCCGACC
AGGATTAGCCAACCTTCGTGCTCCTCCGTTACTCTTTAGGAGGAGACCGCCCCAG
TCAAACTACCCACCAGACACTGTCCGCAACCCGGATTACGGGTCAACGTTAGAA
CATCAAACATTAAAGGGTGGTATTTCAAGGTCGGCTCCATGCAGACTGGCGTCCA
CACTTCAAAGCCTCCCACCTATCCTACACATCAAGGCTCAATGTTCAGTGTCAAG
CTATAGTAAAGGTTCACGGGGTCTTTCCGTCTTGCCG

Figure 7d

CGGGTACACTGCATCTTCACAGCGAGTTCAATTTCACTGAGTCTCGGGTGGAGAC
AGCCTGGCCATCATTACGCCATTCGTGCAGGTCGGAACTTACCCGACAAGGAATT
TCGCTACCTTAGGACCGTTATAGTTACGGCCGCCGTTTACCGGGGCTTCGATCAA
GAGCTTCGCTTGCGCTAACCCCATCAATTAACCTTCCGGCACCGGGCAGGCGTCA
CACCGTATACGTCCACTTTCGTGTTTGCACAGTGCTGTGTTTTAATAAACAGTTG
CAGCCAGCTGGTATCTTCGACTGATTTCAGCTCCATCCGCGAGGGACCTCACCTA
CATATCAGCGTGCCTTCTCCCGAAGTTACGGCACCATTTTGCCTAGTTCCTTCACC
CGAGTTCTCTCAAGCGCCTTGGTATTCTCTACCTGACCACCTGTGTCGGTTGGGG
TACGATTTGATGTTACCTGATGCTTAGAGGCTTTTCCTGGAAGCAGGGCATTTGTT
GCTTCAGCACCGTAGTGCCTCGTCATCACGCCTCAGCCTTGATTTTCCGGATTTGC
CTGGAAAACCAGCCTACACGCTTAAACCGGGACAACCGTCGCCCGGCCAACATA
GCCTTCTCCGTCCCCCCTTCGCAGTAACACCAAGTACAGGAATATTAACCTGTTT
CCCATCGACTACGCCTTTCGGCCTCGCCTTAGGGGTCGACTCACCCTGCCCCGAT
TAACGTTGGACAGGAACCCTTGGTCTTCCGGCGAGCGGGCTTTTCACCCGCTTTA
TCGTTACTTATGTCAGCATTCGCACTTCTGATACCTCCAGCATGCCTCACAGCACA
CCTTCGCAGGCTTACAGAACGCTCCCCTACCCAACAACGCATAAGCGTCGCTGCC
GCAGCTTCGGTGCATGGTTTAGCCCCGTTACATCTTCCGCGCAGGCCGACTCGAC
CAGTGAGCTATTACGCTTTCTTTAAATGATGGCTGCTTCTAAGCCAACATCCTGG
CTGTCTGGGCCTTCCCACATCGTTTCCCACTTAACCATGACTTTGGGACCTTAGCT
GGCGGTCTGGGTTGTTTCCCTCTTCACGACGGACGTTAGCACCCGCCGTGTGTCT
CCCGTGATAACATTCTCCGGTATTCGCAGTTTGCATCGGGTTGGTAAGTCGGGAT
GACCCCCTTGCCGAAACAGTGCTCTACCCCCGGAGATGAATTCACGAGGCGCTAC
CTAAATAGCTTTCGGGGAGAACCAGCTATCTCCCGGTTTGATTGGCCTTTCACCC
CCAGCCACAAGTCATCCGCTAATTTTTCAACATTAGTCGGTTCGGTCCTCCAGTTA
GTGTTACCCAACCTTCAACCTGCCCATGGCTAGATCACCGGGTTTCGGGTCTATA
CCCTGCAACTTAACGCCCAGTTAAGACTCGGTTTCCCTTCGGCTCCCCTATTCGGT
TAACCTTGCTACAGAATATAAGTCGCTGACCCATTATACAAAAGGTACGCAGTCA
CACGCCTAAGCGTGCTCCCACTGCTTGTACGTACACGGTTTCAGGTTCTTTTTCAC
TCCCCTCGCCGGGGTTCTTTTCGCCTTTCCCTCACGGTACTGGTTCACTATCGGTC
AGTCAGGAGTATTTAGCCTTGGAGGATGGTCCCCCCATATTCAGACAGGATACCA
CGTGTCCCGCCCTACTCATCGAGCTCACAGCATGTGCATTTTTGTGTACGGGGCT
GTCACCCTGTATCGCGCGCCTTTCCAGACGCTTCCACTAACACACACACTGATTC
AGGCTCTGGGCTGCTCCCCGTTCGCTCGCCGCTACTGGGGGAATCTCGGTTGATT
TCTTTTCCTCGGGGTACTTAGATGTTTCAGTTCCCCCGGTTCGCCTCATTAACCTA
TGGATTCAGTTAATGATAGTGTGTCGAAACACACTGGGTTTCCCCATTCGGAAAT
CGCCGGTTATAACGGTTCATATCACCTTACCGACGCTTATCGCAGATTAGCACGT
CCTTCATCGCCTCTGACTGCCAGGGCATCCACCGTGTACGCTTAGTCGCTTAACCT
CACAACCCGAAGATGTTTCTTTCGATTCATCATCGTGTTGCGAAAATTTGAGAGA
CTCACGAACAACTCTCGTTGTTCAGTGTTTCAATTTTCAGCTTGATCCAGATTTTT
AAAGAGCAAATATCTCAAACATCACCCGAAGATGAGTTTTGAGATATTAAGGTC
GGCGACTTTCACTCACAAACCAGCAAGTGGCGTCCCTAGGGGATTCGAACCCCT
GTTACCGCCGTGAAAGGGCGGTGTCCTGGGCCTCTAGACGAAGGGGACACGAAA
ATTGCTTATCACGCGTTGCGTGATATTTTCGTGTAGGGTGAGCTTTCATTAATAGA
AAGCGAACGGCCTTATTCTCTTCAGCCTCACTCCCAACGCGTAAACGCCTTGCTT
TTCACTTTCTATCAGACAATCTGTGTGAGCACTAC

Figure 7e

AAAGTACGCTTCTTTAAGGTAATCCCATGATCCAACCGCAGGTTCCCCTACGGTT
ACCTTGTTACGACTTCACCCCAGTCATGAATCACTCCGTGGTAACCGTCCCCCTTG
CGGTTAGACTAGCTACTTCTGGAGCAACCCACTCCCATGGTGTGACGGGCGGTGT
GTACAAGGCCCGGGAACGTATTCACCGTGACATTCTGATTCACGATTACTAGCGA
TTCCGACTTCACGCAGTCGAGTTGCAGACTGCGATCCGGACTACGATCGGTTTTA
TGGGATTAGCTCCACCTCGCGGCTTGGCAACCCTTTGTACCGACCATTGTAGCAC
GTGTGTAGCCCTGGCCGTAAGGGCCATGATGACTTGACGTCATCCCCACCTTCCT
CCGGTTTGTCACCGGCAGTCTCCTTAGAGTGCCCACCCGAGGTGCTGGTAACTAA
GGACAAGGGTTGCGCTCGTTACGGGACTTAACCCAACATCTCACGACACGAGCT
GACGACAGCCATGCAGCACCTGTGTCTGAGTTCCCGAAGGCACCAATCCATCTCT
GGAAAGTTCTCAGCATGTCAAGGCCAGGTAAGGTTCTTCGCGTTGCTTCGAATTA
AACCACATGCTCCACCGCTTGTGCGGGCCCCGTCAATTCATTTGAGTTTTAACCT
TGCGGCCGTACTCCCCAGGCGGTCGACTTATCGCGTTAGCTGCGCCACTAAGATC
TCAAGGATCCCAACGGCTAGTCGACATCGTTTACGGCGTGGACTACCAGGGTATC
TAATCCTGTTTGCTCCCCACGCTTTCGCACCTCAGTGTCAGTATCAGTCCAGGTGG
TCGCCTTCGCCACTGGTGTTCCTTCCTATATCTACGCATTTCACCGCTACACGGA
AATTCCACCACCCTCTACCGTACTCTAGCTCAGTAGTTTTGGATGCAGTTCCCAG
GTTGAGCCCGGGGATTTCACATCCAACTTGCTGAACCACCTACGCGCGCTTTACG
CCCAGTAATTCCGATTAACGCTTGCACCCTTCGTATTACCGCGGCTGCTGGCACG
AAGTTAGCCGGTGCTTATTCTGTTGGTAACGTCAAAACAGCAAGGTATTAACTTA
CTGCCCTTCCTCCCAACTTAAAGTGCTTTACAATCCGAAGACCTTCTTCACACACG
CGGCATGGCTGGATCAGGCTTTCGCCCATTGTCCAATATTCCCCACTGCTGCCTCC
CGTAGGAGTCTGGACCGTGTCTCAGTTCCAGTGTGACTGATCATCCTCTCAGACC
AGTTACGGATCGTCGCCTTGGTAGGCCTTTACCCCACCAACTAGCTAATCCGACC
TAGGCTCATCTGATAGCGTGAGGTCCGAAGATCCCCACTTTGGTCTTGCGACGT
TATGCGGTATTAGCGCCCGTTTCCGGACGTTATCCCCACTACCAGGCAGATTCC
TAGGCATTACTCACCCGTCCGCCGCTGAATCCAGGAGCAAGCTCCCTTCATCCGC
TCGACTTGCATGTGTTAGGCCTGCCGCCAGCGTTCAATCTGAGCCATGATCAAAC
TCTTCAATTTAAAAGTTTGACGCTCAAAGAATTAAACTTCGTAATGAATTACGTG
TTCACTCTTGAGACTTGGTATTCATTTTTCGTCTTGCGACGTTAAGAATCCGTATC
TTCGAGTGCCCACACAGATTGTCTGATAAATTGTTAAAGAGCAGTGCCGCTTCGC
TTTTTCTCAGCGGCCGCTGTGTGAAATTGTTATCCGCTCACAATTCCACACATTAT
ACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGC
CAGCTGCATTAATGAATCGGCCAACGCGCGGGGAGAGGCGGTTTGCGTATTGGG
CGCCAGGGTGGTTTTTCTTTTCACCAGTGAGACGGGCAACAGCTGATTGCCCTTC
ACCGCCTGGCCCTGAGAGAGTTGCAGCAAGCGGTCCACGCTGGTTTGCCCCAGC
AGGCGAAAATCCTGTTTGATGGTGGTTGACGGCGGGATATAACATGAGCTGTCTT
CGGTATCGTCGTATCCCACTACCGAGATATCCGCACCAACGCGCAGCCCGGACTC
GGTAATGGCGCGCATTGCGCCCAGCGCCATCTGATCGTTGGCAACCAGCATCGCA
GTGGGAACGATGCCCTCATTCAGCATTTGCATGGTTTGTTGAAAACCGGACATGG
CACTCCAGTCGCCTTCCCGTTCCGCTATCGGCTGAATTTGATTGCGAGTGAGATA
TTTATGCCAGCCAGCCAGACGCAGACGCGCCGAGACAGAACTTAATGGGCCCGC
TAACAGCGCGATTTGCTGGTGBCCCAATGCGACCAGATGCTCCACGCCCAGTCGC
GTACCGTCTTCATGGGAGAAAATAATA

Figure 7f

```
CTGTTGATGGGTGTCTGGTCAGAGACATCAAGAAATAACGCCGGAACATTAGTG
CAGGCAGCTTCCACAGCAATGGCATCCTGGTCATCCAGCGGATAGTTAATAATCA
GCCCACTGACCCGTTGCGCGAGAAGATTGTGCACCGCCGCTTTACAGGCTTCGAC
GCCGCTTCGTTCTACCATCGACACCACCACGCTGGCACCCAGTTGATCGGCGCGA
GATTTAATCGCCGCGACAATTTGCGACGGCGCGTGCAGGGCCAGACTGGAGGTG
GCAACGCCAATCAGCAACGACTGTTTGCCCGCCAGTTGTTGTGCCACGCGGTTGG
GAATGTAATTCAGCTCCGCCATCGCCGCTTCCACTTTTTCCCGCGTTTTCGCAGAA
ACGTGGCTGGCCTGGTTCACCACGCGGGAAACGGTCTGATAAGAGACACCGGCA
TACTCTGCGACATCGTATAACGTTACTGGTTTCACATTCACCACCCTGAATTGACT
CTCTTCCGGGCGCTATCATGCCATACCGCGAAAGGTTTTGCACCATTCGATGGTG
TCGGATCCTCTAGCCGGACCCACTTGCGGCCACGATCCGTCCGCCGTAAGGCTCA
TACCGTTAATTATTCCCCCCACGGGAGACCTGAGCAAACTGCCCTCAGGCATTT
GAGAAGCACAGGGTCACACTGCTTCGGGTAGTCAATAAACCGGTAAACCAGCAA
TAGACATAAGCGGCTATTTAACGACCCTGCCCTGAACCGACGACCGGGTCGAATT
TGCTTTCGAATTTCTGCCATTCATCCGCTTATTATCACTTATTCAGGCGTAGCACC
AGGCGTTTAAGGGCACCAATAACTGCCTTAAAAAAA
```

Figure 8a

ACTCACCAGTCACAGAAAAGCATCTTACGGATGGCATGACAGTAAGAGAATTAT
GCAGTGCTGCCATAACCATGAGTGATAACACTGCGGCCAACTTACTTCTGACAAC
GATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGA
GCGTGACACCACGATGCCTGCAGCAATGGCAACAACGTTGCGCAAACTATTAAC
TGGCGAACTACTTACTCTAGCTTCCCGGCAACAATTAATAGACTGGATGGAGGCG
GATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAA
GCATTGGTAACTGTCAGACCAAGTTTACTCATATATACTTTAGATTGATTTAAAA
CTTCATTTTTAATTTAAAAGGATCTAGGTGAAGATCCTTTTTGATAATCTCATGAC
CAAAATCCCTTAACGTGAGTTTTCGTTCCACTGAGCGTCAGACCCCTTAATAAGA
TGATCTTCTTGAGATCGTTTTGGTCTGCGCGTAATCTCTTGCTCTGAAAACGAAAA
AACCGCCTTGCAGGGCGGTTTTTCGAAGGTTCTCTGAGCTACCAACTCTTTGAAC
CGAGGTAACTGGCTTGGAGGAGCGCAGTCACCAAAACTTGTCCTTTCAGTTTAGC
CTTAACCGGCGCATGACTTCAAGACTAACTCCTCTAAATCAATTACCAGTGGCTG
CTGCCAGTGGTGCTTTTGCATGTCTTTCCGGGTTGGACTCAAGACGATAGTTACC
GGATAAGGCGCAGCGGTCGGACTGAACGGGGGGTTCGTGCATACAGTCCAGCTT
GGAGCGAACTGCCTACCCGGAACTGAGTGTCAGGCGTGGAATGAGACAAACGCG
GCCATAACAGCGGAATGACACCGGTAAACCGAAAGGCAGGAACAGGAGAGCGC
ACGAGGGAGCCGCCAGGGGGAAACGCCTGGTATCTTTATAGTCCTGTCGGGTTTC
GCCACCACTGATTTGAGCGTCAGATTTCGTGATGCTTGTCAGGGGGGCGGAGCCT
ATGGAAAAACGGCTTTGCCGCGGCCCTCTCACTTCCCTGTTAAGTATCTTCCTGG
CATCTTCCAGGAAATCTCCGCCCCGTTCGTAAGCCATTTCCGCTCGCCGCAGTCG
AACGACCGAGCGTAGCGAGTCAGTGAGCGAGGAAGCGGAATATATCCTGTATCA
CATATTCTGCTGACGCACCGGTGCAGCCTTTTTTCTCCTGCCACATGAAGCACTTC
ACTGACACCCTCATCAGTGCCAACATAGTAAGCCAGTATACACTCCGCTAGCGCT
GAGGTCTGCCTCGTGAAGAAGGTGTTGCTGACTCATACCAGGCCTGAATCGCCCC
ATCATCCAGCCAGAAAGTGAGGGAGCCACGGTTGATGAGAGCTTTGTTGTAGGT
GGACCAGTTGGTGATTTTGAACTTTTGCTTTGCCACGGAACGGTCTGCGTTGTCG
GAAGATGCGTGATCTGATCCTTCAACTCAGCAAAAGTTCGATTTATTCAACAAA
GCCACGTTGTGTCTCAAAATCTCTGATGTTACATTGCACAAGATAAAAATATATC
ATCATGAACAATAAAACTGTCTGCTTACATAAACAGTAATACAAGGGGTGTTATG
AGCCATATTCAACGGGAAACGTCTTGCTCGAGGCCGCGATTAAATTCCAACATGG
ATGCTGATTTATATGGGTATAAATGGGCTCGCGATAATGTCGGGCAATCAGGTGC
GACAATCTATCGATTGTATGGGAAGCCCGATGCGCCAGAGTTGTTTCTGAAACAT
GGCAAAGGTAGCGTTGCCAATGATGTTACAGATGAGATGGTCAGACTAAACTGG
CTGACGGAATTTATGCCTCTTCCGACCATCAAGCATTTTATCCGTACTCCTGATGA
TGCATGGTTACTCACCACTGCGATCCCCGGGAAAACAGCATTCCAGGTATTAGAA
GAATATCCTGATTCAGGTGAAAATATTGCTGATGCGCTGGCAGTGTTCCTGCGCC
GGTTGCATTCGATTCCTGTTTGTAATTGTCCTTTTAACAGCGATCGCGTATTTCGT
CTCGCTCAGGCGCAATCACGAATGAATAACGGTTTGGTTGATGCGAGTGATTTTG
ATGACGAGCGTAATGGCTGGCCTGTTGAACAAGTCTGGAAAGAAATGCATAAAC
TTTTGCCATTCTCACCGGATTCAGTCGTCACTC

Figure 8b

ATGGTGATTTCTCACTTGATAACCTTATTTTTGACGAGGGGAAATTAATAGGTTG
TATTGATGTTGGACGAGTCGGAATCGCAGACCGATACCAGGATCTTGCCATCCTA
TGGAACTGCCTCGGTGAGTTTTCTCCTTCATTACAGAAACGGCTTTTTCAAAAAT
ATGGTATTGATAATCCTGATÁTGAATAAATTGCAGTTTCATTTGATGCTCGATGA
GTTTTTCTAATCAGAATTGGTTAATTGGTTGTAACACTGGCAGAGCATTACGCTG
ACTTGACGGGACGGCGGCTTTGTTGAATAAATCGAACTTTTGCTGAGTTGAAGGA
TCAGATCACGCATCTTCCCGACAACGCAGACCGTTCCGTGGCAAAGCAAAAGTTC
AAAATCACTAGTCGACCATGGTACCATCGATGCATAATGTGCCTGTCAAATGGAC
GAAGCAGGGATTCTGCAAACCCTATGCTACTCCGTCAAGCCGTCAATTGTCTGAT
TCGTTACCAATTATGACAACTTGACGGCTACATCATTCACTTTTTCTTCACAACCG
GCACGGAACTCGCTCGGGCTGGCCCCGGTGCATTTTTTAAATACCCGCGAGAAAT
AGAGTTGATCGTCAAAACCAACATTGCGACCGACGGTGGCGATAGGCATCCGGG
TGGTGCTCAAAAGCAGCTTCGCCTGGCTGATACGTTGGTCCTCGCGCCAGCTTAA
GACGCTAATCCCTAACTGCTGGCGGAAAAGATGTGACAGACGCGACGGCGACAA
GCAAACATGCTGTGCGACGCTGGCGATATCAAAATTGCTGTCTGCCAGGTGATCG
CTGATGTACTGACAAGCCTCGCGTACCCGATTATCCATCGGTGGATGGAGCGACT
CGTTAATCGCTTCCATGCGCCGCAGTAACAATTGCTCAAGCAGATTTATCGCCAG
CAGCTCCGAATAGCGCCCTTCCCCTTGCCCGGCGTTAATGATTTGCCCAAACAGG
TCGCTGAAATGCGGCTGGTGCGCTTCATCCGGGCGAAAGAACCCCGTATTGGCA
AATATTGACGGCCAGTTAAGCCATTCATGCCAGTAGGCGCGCGGACGAAAGTAA
ACCCACTGGTGATACCATTCGCGAGCCTCCGGATGACGACCGTAGTGATGAATCT
CTCCTGGCGGGAACAGCAAAATATCACCCGGTCGGCAAACAAATTCTCGTCCCTG
ATTTTTCACCACCCCCTGACCGCGAATGGTGAGATTGAGAATATAACCTTTCATT
CCCAGCGGTCGGTCGATAAAAAAATCGAGATAACCGTTGGCCCTCAATCGGCGTT
AAACCCGCCACCAGATGGGCATTAAACGAGTATCCCGGCAGCAGGGGATCATTT
TGCGCTTCAGCCATACTTTTCATACTCCCGCCATTCAGAGAAGAAACCAATTGTC
CATATTGCATCAGACATTGCCGTCACTGCGTCTTTTACTGGCTCTTCTCGCTAACC
AAACCGGTAACCCCGCTTATTAAAAGCATTCTGTAACAAAGCGGGACCAAAGCC
ATGACAAAAACGCGTAACAAAAGTGTCTATAATCACGGCAGAAAAGTCCACATT
GATTATTTGCACGGCGTCACACTTTGCTATGCCATAGCATTTTTATCCATAAGATT
AGCGGATCCTACCTGACGCTTTTTATCGCAACTCTCTACTGTTTCTCCATGCGGCC
GCATGCAAGCTTCTAGAATAAAACGAAAGGCTCAGTCGAAAGACTGGGCCTTTC
GTTTTATCTGTTGTTTGTCGGTGAACGCTCTCCTGAGTAGGACAAATCCGCCGGG
AGCGGATTTGAACGTTGCGAAGCAACGGCCCGGAGGGTGGCGGGCAGGACGCCC
GCCATAAACTGCCAGGCATCAAATTAAGCAGAAGGCCATCCTGACGGATGGCCT
TTTTGAATTCACTGGCCGTCGTTTTACAACGTCGTGACTGGGAAAACCCTGGCGT
TACCCAACTTAATCGCCTTGCAGCACATCCCCCTTTCGCCAG

Figure 9a

ACTCACCAGTCACAGAAAAGCATCTTACGGATGGCATGACAGTAAGAGAATTAT
GCAGTGCTGCCATAACCATGAGTGATAACACTGCGGCCAACTTACTTCTGACAAC
GATCGGAGGACCGAAGGAGCTAACCGCTTTTTTGCACAACATGGGGGATCATGT
AACTCGCCTTGATCGTGGGAACCGGAGCTGAATGAAGCCATACCAAACGACGA
GCGTGACACCACGATGCCTGCAGCAATGGCAACAACGTTGCGCAAACTATTAAC
TGGCGAACTACTTACTCTAGCTTCCCGGCAACAATTAATAGACTGGATGGAGGCG
GATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAA
GCATTGGTAACTGTCAGACCAAGTTTACTCATATATACTTTAGATTGATTTAAAA
CTTCATTTTTAATTTAAAAGGATCTAGGTGAAGATCCTTTTTGATAATCTCATGAC
CAAAATCCCTTAACGTGAGTTTTCGTTCCACTGAGCGTCAGACCCCTTAATAAGA
TGATCTTCTTGAGATCGTTTGGTCTGCGCGTAATCTCTTGCTCTGAAAACGAAAA
AACCGCCTTGCAGGGCGGTTTTTCGAAGGTTCTCTGAGCTACCAACTCTTTGAAC
CGAGGTAACTGGCTTGGAGGAGCGCAGTCACCAAAACTTGTCCTTTCAGTTTAGC
CTTAACCGGCGCATGACTTCAAGACTAACTCCTCTAAATCAATTACCAGTGGCTG
CTGCCAGTGGTGCTTTTGCATGTCTTTCCGGGTTGGACTCAAGACGATAGTTACC
GGATAAGGCGCAGCGGTCGGACTGAACGGGGGGTTCGTGCATACAGTCCAGCTT
GGAGCGAACTGCCTACCCGGAACTGAGTGTCAGGCGTGGAATGAGACAAACGCG
GCCATAACAGCGGAATGACACCGGTAAACCGAAAGGCAGGAACAGGAGAGCGC
ACGAGGGAGCCGCCAGGGGGAAACGCCTGGTATCTTTATAGTCCTGTCGGGTTTC
GCCACCACTGATTTGAGCGTCAGATTTCGTGATGCTTGTCAGGGGGGCGGAGCCT
ATGGAAAAACGGCTTTGCCGCGGCCCTCTCACTTCCCTGTTAAGTATCTTCCTGG
CATCTTCCAGGAAATCTCCGCCCCGTTCGTAAGCCATTTCCGCTCGCCGCAGTCG
AACGACCGAGCGTAGCGAGTCAGTGAGCGAGGAAGCGGAATATATCCTGTATCA
CATATTCTGCTGACGCACCGGTGCAGCCTTTTTTCTCCTGCCACATGAAGCACTTC
ACTGACACCCTCATCAGTGCCAACATAGTAAGCCAGTATACACTCCGCTAGCGCT
GAGGTCTGCCTCGTGAAGAAGGTGTTGCTGACTCATACCAGGCCTGAATCGCCCC
ATCATCCAGCCAGAAAGTGAGGGAGCCACGGTTGATGAGAGCTTTGTTGTAGGT
GGACCAGTTGGTGATTTTGAACTTTTGCTTTGCCACGGAACGGTCTGCGTTGTCG
GGAAGATGCGTGATCTGATCCTTCAACTCAGCAAAAGTTCGATTTATTCAACAAA
GCCACGTTGTGTCTCAAAATCTCTGATGTTACATTGCACAAGATAAAAATATATC
ATCATGAACAATAAAACTGTCTGCTTACATAAACAGTAATACAAGGGGTGTTATG
AGCCATATTCAACGGGAAACGTCTTGCTCGAGGCCGCGATTAAATTCCAACATGG
ATGCTGATTTATATGGGTATAAATGGGCTCGCGATAATGTCGGGCAATCAGGTGC
GACAATCTATCGATTGTATGGGAAGCCCGATGCGCCAGAGTTGTTTCTGAAACAT
GGCAAAGGTAGCGTTGCCAATGATGTTACAGATGAGATGGTCAGACTAAACTGG
CTGACGGAATTTATGCCTCTTCCGACCATCAAGCATTTTATCCGTACTCCTGATGA
TGCATGGTTACTCACCACTGCGATCCCCGGGAAAACAGCATTCCAGGTATTAGAA
GAATATCCTGATTCAGGTGAAAATATTGCTGATGCGCTGGCAGTGTTCCTGCGCC
GGTTGCATTCGATTCCTGTTTGTAATTGTCCTTTTAACAGCGATCGCGTATTTCGT
CTCGCTCAGGCGCAATCACGAATGAATAACGGTTTGGTTGATGCGAGTGATTTTG
ATGACGAGCGTAATGGCTGGCCTGTTAACAAGTCTGGAAAGAAATGCATAAAC
TTTTGCCATTCTCACCGGATTCAGTCGTCACTC

Figure 9b

```
ATGGTGATTTCTCACTTGATAACCTTATTTTTGACGAGGGGAAATTAATAGGTTG
TATTGATGTTGGACGAGTCGGAATCGCAGACCGATACCAGGATCTTGCCATCCTA
TGGAACTGCCTCGGTGAGTTTTCTCCTTCATTACAGAAACGGCTTTTTCAAAAAT
ATGGTATTGATAATCCTGATATGAATAAATTGCAGTTTCATTTGATGCTCGATGA
GTTTTTCTAATCAGAATTGGTTAATTGGTTGTAACACTGGCAGAGCATTACGCTG
ACTTGACGGGACGGCGGCTTTGTTGAATAAATCGAACTTTTGCTGAGTTGAAGGA
TCAGATCACGCATCTTCCCGACAACGCAGACCGTTCCGTGGCAAAGCAAAAGTTC
AAAATCACTAGTCGACCATGGTACCATCGATGCATAATGTGCCTGTCAAATGGAC
GAAGCAGGGATTCTGCAAACCCTATGCTACTCCGTCAAGCCGTCAATTGTCTGAT
TCGTTACCAATTATGACAACTTGACGGCTACATCATTCACTTTTTCTTCACAACCG
GCACGGAACTCGCTCGGGCTGGCCCCGGTGCATTTTTTAAATACCCGCGAGAAAT
AGAGTTGATCGTCAAAACCAACATTGCGACCGACGGTGGCGATAGGCATCCGGG
TGGTGCTCAAAAGCAGCTTCGCCTGGCTGATACGTTGGTCCTCGCGCCAGCTTAA
GACGCTAATCCCTAACTGCTGGCGGAAAAGATGTGACAGACGCGACGGCGACAA
GCAAACATGCTGTGCGACGCTGGCGATATCAAAATTGCTGTCTGCCAGGTGATCG
CTGATGTACTGACAAGCCTCGCGTACCCGATTATCCATCGGTGGATGGAGCGACT
CGTTAATCGCTTCCATGCGCCGCAGTAACAATTGCTCAAGCAGATTTATCGCCAG
CAGCTCCGAATAGCGCCCTTCCCCTTGCCCGGCGTTAATGATTTGCCCAAACAGG
TCGCTGAAATGCGGCTGGTGCGCTTCATCCGGGCGAAAGAACCCCGTATTGGCA
AATATTGACGGCCAGTTAAGCCATTCATGCCAGTAGGCGCGCGGACGAAAGTAA
ACCCACTGGTGATACCATTCGCGAGCCTCCGGATGACGACCGTAGTGATGAATCT
CTCCTGGCGGGAACAGCAAAATATCACCCGGTCGGCAAACAAATTCTCGTCCCTG
ATTTTTCACCACCCCCTGACCGCGAATGGTGAGATTGAGAATATAACCTTTCATT
CCCAGCGGTCGGTCGATAAAAAAATCGAGATAACCGTTGGCCTCAATCGGCGTT
AAACCCGCCACCAGATGGGCATTAAACGAGTATCCCGGCAGCAGGGGATCATTT
TGCGCTTCAGCCATACTTTTCATACTCCCGCCATTCAGAGAAGAAACCAATTGTC
CATATTGCATCAGACATTGCCGTCACTGCGTCTTTTACTGGCTCTTCTCGCTAACC
AAACCGGTAACCCCGCTTATTAAAAGCATTCTGTAACAAAGCGGGACCAAAGCC
ATGACAAAAACGCGTAACAAAAGTGTCTATAATCACGGCAGAAAAGTCCACATT
GATTATTTGCACGGCGTCACACTTTGCTATGCCATAGCATTTTTATCCATAAGATT
AGCGGATCCTACCTGACGCTTTTTATCGCAACTCTCTACTGTTTCTCCATGCGGCC
GCCTATTTACCCAGTTTTTTTCGAGGAGCTCGACGATGGCCAACACACCTTCCGC
CAAAAAACGCGCCAAACAGGCTGAGAAGCGTCGCAGCCACAACGCCAGCCTGCG
CTCCATGGTGCGCACCTACATCAAGAACGTCGTGAAAGCCATCGACGCCAAGGA
CCTGGAAAAGCCCAGGCCGCCTTCACCGCCGCTGTACCGGTGATCGACCGCAT
GGCTGACAAAGGCATCATCCACAAGAACAAGGCTGCTCGTCATAAGAGCCGTCT
GAGCGGCCACATCAAGGCCCTCAGCACCGCTGCCGCCTAATCTAGAATAAAACG
AAAGGCTCAGTCGAAAGACTGGGCCTTTCGTTTTATCTGTTGTTTGTCGGTGAAC
GCTCTCCTGAGTAGGACAAATCCGCCGGGAGCGGATTTGAACGTTGCGAAGCAA
CGGCCCGGAGGGTGGCGGGCAGGACGCCCGCCATAAACTGCCAGGCATCAAATT
AAGCAGAAGGCCATCCTGACGGATGGCCTTTTTGAATTCACTGGCCGTCGTTTTA
CAACGTCGTGACTGGGAAAACCCTGGCGTTACCCAACTTAATCGCCTTGCAGCAC
ATCCCCCTTTCGCCAG
```

| Clone | RNA sequences | | $\Delta G^0_{37}$ | MIC | | CAT | | Induction |
|---|---|---|---|---|---|---|---|---|
| | 5' CAR1 R2 R3 R4 R5 CUCG 3' CAT mRNA | | | µg of Cm/mL | | CPM | | |
| | 3' AUU M5 M4 M3 M2 M1 ACU 5' 16S rRNA | | kcal/mol | -1 | +1 | -1 | +1 | -1/+1 |
| Random | | | | | | | | |
| pRNA9 | 5' CAGGAGGCUCG 3'<br>3' AUUCCUCCACU 5' | | -9.8 | 500 | 500 | 2803 ± 68 | 2700 ± 196 | 1.0 |
| pRNA6 | 5' CAGUGUGCUCG 3'<br>3' AUUCACACACU 5' | | -7.8 | 100 | 200 | 4033 ±1040 | 12437 ±2491 | 3.1 |
| VII30 | 5' CAUAUCCCUCG 3'<br>3' AUUUAGGGACU 5' | | -8.4 | 100 | 500 | 6293 ± 706 | 72206 ± 706 | 11.5 |
| VII43 | 5' CAAACACCUCG 3'<br>3' AUUGGAGAACU 5' | | -8.1 | 125 | 500 | 5603 ±1011 | 47667 ± 891 | 8.5 |
| VII64<br>VII65 | 5' CAUACCUCUCG 3'<br>3' AUUGGAGACU 5' | | -7.3 | 100 | 500 | 6200 ± 953 | 37311 ±3978 | 6.0 |
| VIII29 | 5' CAUAAUCCUCG 3'<br>3' AUUAGGAGACU 5' | | -10.9 | 125 | 600 | 7869 ± 416 | 91153 ±4003 | 11.6 |
| VIII46 | 5' CAAAUACCUCG 3'<br>3' AUUGGAGUACU 5' | | -7.7 | 100 | 500 | 6431 ± 816 | 46840 ± 796 | 7.3 |
| VIII77 | 5' CAUAACCUCG 3'<br>3' AUUGGAGUACU 5' | | -7.7 | 150 | 600 | 6794 ± 650 | 44358 ±4841 | 6.5 |
| VIII93 | 5' CAUCCAUCCUCG 3'<br>3' AUUGGAGAACU 5' | | -8.5 | 100 | 500 | 5643 ± 897 | 24888 ±2388 | 4.4 |
| IX24 | 5' CACCGAUCCUCG 3'<br>3' AUUAGGGUACU 5' | | -7.3 | 100 | 650 | 7524 ± 263 | 91809 ±4542 | 12.7 |
| IX32 | 5' CAUACUUCCUCG 3'<br>3' AUUGGAGUACU 5' | | -7.7 | 100 | 500 | 5783 ± 971 | 32164 ±5862 | 5.6 |
| IX67 | 5' CAUAUACCUCG 3'<br>3' AUUGGAGAACU 5' | | -8.1 | 125 | 600 | 6063 ± 787 | 24581 ±3009 | 4.1 |

FIG. 10

| Clone | RNA sequences | | MIC (μg/mL) | |
|---|---|---|---|---|
| | | | −1 | +1 |
| Mutated positions | 5' C A U A U C C C U N N N A A A U G 3' CAT mRNA<br>3' A U U A G G G U A C U A G G 5' 16S rRNA | | | |
| pRNA100 | 5' C A U A U [C C C U] C G A G A A A U G 3'<br>3' A U [U A G G G] U A C U A G G 5' | | 100 | 650 |
| pRNA100<br>+ wt MBS | 5' C A U A U C C C U C G [A G A] A A A U G 3'<br>3' A U U A G G G [U C U] C A C U A G G 5' | | 50 | 50 |
| pRNA122 | 5' C A U A U [C C C U] C C G C A A A U G 3'<br>3' A U [U A G G G] U A C U A G G 5' | | 50 | 600 |
| pRNA122<br>+ wt MBS | 5' C A U A U C C C U C C G [C A A] A U G 3'<br>3' A U U A G G G [U C C] A C U A G G 5' | | 10 | 10 |
| pRNA125 | 5' C A U A U [C C C U] C C G A A A A U G 3'<br>3' A U [U A G G G] U A C U A G G 5' | | 80 | 600 |
| pRNA127 | 5' C A U A U [C C C U] C C G C A A A U G 3'<br>3' A U [U A G G G] U A C U A G G 5' | | 50 | 600 |
| pRNA128 | 5' C A U A U [C C C U] C C A C A A A U G 3'<br>3' A U [U A G G G] U A C U A G G 5' | | 50 | 600 |

FIG. 11

| FIG. 12A-1 |
|---|
| FIG. 12A-2 |
| FIG. 12A-3 |

FIG. 12a

| Clone | Alignment of CAT mRNA and 16S rRNA | MIC (μg of Cm/mL) | | $\Delta G^0_{37}$ (kcal/mol) |
|---|---|---|---|---|
| Random | 5' C A R1 R2 R3 R4 R5 C U C G 3' CAT mRNA<br>3' A U U M5 M4 M3 M2 M1 A C U 5' 16S rRNA | no IPTG | 1 mM IPTG | |
| wild-type | 5' C A G G A G G C U C G 3'<br>3' A U U C C U C C A C U 5' | 500 | 500 | -9.8 |
| 1 | 5' C A A U C C C C U C G 3'<br>3' A U U A G G G A C U 5' | 100 | 400 | -8.3 |
| 2 | 5' C A U A C C U C U C G 3'<br>3' A U U U G G G U A A C U 5' | 50 | 100 | -4 |
| 3 | 5' C A C A G U C C U C G 3'<br>3' A U U A G C A G A C U 5' | 50 | 100 | -1.9 |

| # | Sequence | | | |
|---|---|---|---|---|
| 15 | 5'C A C C C A C C U C G 3'<br>3'A U G G G U G G A G C U 5' | 50 | 200 | -7 |
| 16 | 5'C A U C C A C C U C G 3'<br>3'A U G G G U G G A C U 5' | 50 | 100 | -7.3 |
| 17 | 5'C A A C U A C U U C G 3'<br>3'A U U G A U G A A C U 5' | 50 | 100 | -0.8 |
| 18 | 5'C A A U C A C U U C G 3'<br>3'A U U A G U G A A C U 5' | 50 | 100 | -2.1 |
| 19 | 5'C A U G U A C U U C G 3'<br>3'A U A G A U G A A C U 5' | 200 | 200 | -5.6 |
| 20 | 5'C A A U G U A C U U C G 3'<br>3'A U U A G A U G A A C U 5' | 200 | 500 | -6.2 |
| 21 | 5'C A C C U G A C U U C G 3'<br>3'A U G G A U G A A C U 5' | 200 | 500 | -7.3 |
| 22 | 5'C A G U U A C G G A C U 5'<br>3'A U C A A U G C C U G A 5' | 100 | 200 | -0.3 |
| 23 | 5'C A A U C C A C U U C G 3'<br>3'A U U A G G U G A A C U 5' | 200 | 400 | -10.6 |
| 24 | 5'C A C G A U C U C G 3'<br>3'A U U G G A C U 5' | 100 | 200 | -0.2 |

FIG. 12A-3

| Clone | Alignment of CAT mRNA and 16S rRNA | MIC (μg of Cm/mL) | | $\Delta G^0_{37}$ (kcal/mol) |
|---|---|---|---|---|
| Random | 5' C A R1 R2 R3 R4 R5 C U C G 3' CAT mRNA<br>3' A U U M5 M4 M3 M2 M1 A C U 5' 16S rRNA | no IPTG | 1 mM IPTG | |
| 25 | 5' C A U A G C A C U C G 3'<br>3' A U U A U C G U A C U 5' | 200 | 400 | -6.8 |
| 26 | 5' C A A C U A C U C G 3'<br>3' A U U G U G A U A C U 5' | 100 | 200 | -3.4 |
| 27 | 5' C A A U A U C U C G 3'<br>3' A U U U A U G G A A C U 5' | 100 | 400 | -5.3 |

FIG. 12B-1

| FIG. 12B-1 |
| FIG. 12B-2 |
| FIG. 12B-3 |

FIG. 12b

| # | Sequence | | | |
|---|---|---|---|---|
| 28 | 5'C A A A A U C U C C G 3'<br>3'A A U A G A G G C U 5' | 200 | 400 | -1.6 |
| 29 | 5'C A C A U U C C G 3'<br>3'A U G A A G G C U 5' | 50 | 100 | -9.1 |
| 30 | 5'C A U A U C C C G 3'<br>3'A U A A G G G C U 5' | 100 | 400 | -5.3 |
| 31 | 5'C A U C C A C U C G 3'<br>3'A U A G G U G A G C 5' | 50 | 200 | -3.1 |
| 32 | 5'C A A C U A C C G 3'<br>3'A A G A U G G C U 5' | 100 | 400 | -4.5 |
| 33 | 5'C A A A C C G C C G 3'<br>3'A U U G G C G G C 5' | 100 | 400 | -7.2 |
| 34 | 5'C A A A C U A G A C G 3'<br>3'A A U U G A U C U G C 5' | 200 | 400 | -8 |
| 35 | 5'C A A C C G A C U C G 3'<br>3'A A U G G C U G A G C 5' | 50 | 200 | -5 |
| 36 | 5'C A A U C U U G A C C G 3'<br>3'A A U A G A A C U G G C 5' | 200 | 500 | -3.9 |
| 37 | 5'C A A C C G G A U C G 3'<br>3'A U U G G C C U A G C 5' | 100 | 500 | -8.4 |
| 38 | 5'C A U A C C G G A C G 3'<br>3'A A U A U G G C C U G C 5' | 150 | 500 | -8.1 |

FIG. 12B-2

| # | Sequence | | | |
|---|---|---|---|---|
| 39 | 5'C A A C G A A C U C G 3'<br>3'A U U G C U U G A G C U 5' | 100 | 400 | -5.7 |
| 40 | 5'C A U C A U C U C G 3'<br>3'A U A G U A G A G C U 5' | 100 | 400 | -6.2 |
| 41 | 5'C A U C A C C U C G 3'<br>3'A U A G U G G A G C U 5' | 100 | 500 | -7.3 |
| 42 | 5'C A A U A C U C G 3'<br>3'A U U A U G A G A C U 5' | 200 | 500 | -3.6 |
| 43 | 5'C A A U A C C U C G 3'<br>3'A U U A U G G A G A C U 5' | 100 | 500 | -7.7 |
| 44 | 5'C A C U A C C U C G 3'<br>3'A U G A U G G A G U C U 5' | 150 | 600 | -7.7 |
| 45 | 5'C A G U A C C U C G 3'<br>3'A U C A U G G A G U C U 5' | 100 | 500 | -8.5 |
| 46 | 5'C A C C A U C C U C G 3'<br>3'A U G G U A G G A G U C U 5' | 100 | 700 | -7.3 |
| 47 | 5'C A C U A C C U C G 3'<br>3'A U G A U G G A G A C U 5' | 100 | 500 | -7.7 |
| 48 | 5'C A U A C C U C G 3'<br>3'A U A U G G A G A C U 5' | 200 | 600 | -8 |

| E. coli | P. aeruginosa | % GFP |
|---|---|---|
| 1-14 & 922-1542 | 15-921 | 46.2 ± 0.3 |
| 1-921 & 1505-1542 | 922-1504 | 98.9 ± 0.7 |
| 1-528 & 1505-1542 | 529-1504<br>basepair positions<br>U513 & A538 | 121 ± 2.2 |
| 1-307 & 1505-1542 | 308-1504<br>A289, U307 & U311 | 108.9 ± 1.9 |
| 1-14, 176-188 &<br>1505-1542 | 15-175 & 189-1504 | 96 ± 2.2 |

Pa 16S rRNA

METHODS AND COMPOSITIONS FOR THE IDENTIFICATION OF ANTIBIOTICS THAT ARE NOT SUSCEPTIBLE TO ANTIBIOTIC RESISTANCE IN *PSEUDOMONAS AERUGINOSA*

This application is the National Stage of International Application No. PCT/US2006/018187, filed May 11, 2006, which claims priority to U.S. Appl. Ser. No. 60/680,134, filed May 11, 2005, the contents of both of which are incorporated herein by reference.

GOVERNMENT SUPPORT

This invention was made with government support under Grant Number NIH SBIR AI060275-01 awarded by the National Institutes of Health. The government has certain rights in the invention.

BACKGROUND

Ribosomes are composed of one large and one small subunit containing three or four RNA molecules and over fifty proteins. The part of the ribosome that is directly involved in protein synthesis is the ribosomal RNA (rRNA). The ribosomal proteins are responsible for folding the rRNAs into their correct three-dimensional structures. Ribosomes and the protein synthesis process are very similar in all organisms. One difference between bacteria and other organisms, however, is the way that ribosomes recognize mRNA molecules that are ready to be translated. In bacteria, this process involves a base-pairing interaction between several nucleotides near the beginning of the mRNA and an equal number of nucleotides at the end of the ribosomal RNA molecule in the small subunit. The mRNA sequence is known as the Shine-Dalgarno (SD) sequence and its counterpart on the rRNA is called the Anti-Shine-Dalgarno (ASD) sequence.

There is now extensive biochemical, genetic and phylogenetic evidence indicating that rRNA is directly involved in virtually every aspect of ribosome function (Garrett, R. A., et al. (2000) The Ribosome: Structure, Function, Antibiotics, and Cellular Interactions. ASM Press, Washington, D.C.). Genetic and functional analyses of rRNA mutations in *E. coli* and most other organisms have been complicated by the presence of multiple rRNA genes and by the occurrence of dominant lethal rRNA mutations. Because there are seven rRNA operons in *E. coli*, the phenotypic expression of rRNA mutations may be affected by the relative amounts of mutant and wild-type ribosomes in the cell. Thus, detection of mutant phenotypes can be hindered by the presence of wild-type ribosomes. A variety of approaches have been designed to circumvent these problems.

One common approach uses cloned copies of a wild-type rRNA operon (Brosius, J., et al. (1981) Plasmid 6: 112-118; Sigmund, C. D. et al. (1982) Proc. Natl. Acad. Sci. U.S.A. 79: 5602-5606). Several groups have used this system to detect phenotypic differences caused by a high level of expression of mutant ribosomes. Recently, a strain of *E. coli* was constructed in which the only supply of ribosomal RNA was plasmid encoded (Asai, T., (1999) J. Bacteriol. 181: 3803-3809). This system has been used to study transcriptional regulation of rRNA synthesis, as well as ribosomal RNA function (Voulgaris, J., et al. (1999) J. Bacteriol. 181: 4170-4175; Koosha, H., et al. (2000) RNA. 6: 1166-1173; Sergiev, P. V., et al. (2000) J. Mol. Biol. 299: 379-389; O'Connor, M. et al. (2001) Nucl. Acids Res. 29: 1420-1425; O'Connor, M., et al. (2001) Nucl. Acids Res. 29: 710-715; Vila-Sanjurjo, A. et al. (2001) J. Mol. Biol. 308: 457-463); Morosyuk S. V., et al. (2000) J. Mol. Biol. 300 (1):113-126; Morosyuk S. V., et al. (2001) J. Mol. Biol. 307 (1):197-210; and Morosyuk S. V., et al. (2001) J. Mol. Biol. 307 (1):211-228. Hui et al. showed that mRNA could be directed to a specific subset of plasmid-encoded ribosomes by altering the message binding site (MBS) of the ribosome while at the same time altering the ribosome binding site (RBS) of an mRNA (Hui, A., et al. (1987) Methods Enzymol. 153: 432-452).

Although each of the above methods has contributed significantly to the understanding of rRNA function, progress in this field has been hampered both by the complexity of translation and by difficulty in applying standard genetic selection techniques to these systems.

Resistance to antibiotics, a matter of growing concern, is caused partly by antibiotic overuse. According to a study published by the Journal of the American Medical Association in 2001, between 1989 to 1999 American adults made some 6.7 million visits a year to the doctor for sore throat. In 73% of those visits, the study found, the patient was treated with antibiotics, though only 5%-17% of sore throats are caused by bacterial infections, the only kind that respond to antibiotics. Macrolide antibiotics in particular are becoming extremely popular for treatment of upper respiratory infections, in part because of their typically short, convenient course of treatment. Research has linked such vast use to a rise in resistant bacteria and the recent development of multiple drug resistance has underscored the need for antibiotics which are highly specific and refractory to the development of drug resistance.

Microorganisms can be resistant to antibiotics by four mechanisms. First, resistance can occur by reducing the amount of antibiotic that accumulates in the cell. Cells can accomplish this by either reducing the uptake of the antibiotic into the cell or by pumping the antibiotic out of the cell. Uptake mediated resistance often occurs, because a particular organism does not have the antibiotic transport protein on the cell surface or occasionally when the constituents of the membrane are mutated in a way that interferes with transport of the antibiotic into a cell. Uptake mediated resistance is only possible in instances where the drug gains entry through a nonessential transport molecule. Efflux mechanisms of antibiotic resistance occur via transporter proteins. These can be highly specific transporters that transport a particular antibiotic, such as tetracycline, out of the cell or they can be more general transporters that transport groups of molecules with similar characteristics out of the cell. The most notorious example of a nonspecific transporter is the multi drug resistance transporter (MDR).

Inactivating the antibiotic is another mechanism by which microorganisms can become resistant to antibiotics. Antibiotic inactivation is accomplished when an enzyme in the cell chemically alters the antibiotic so that it no longer binds to its intended target. These enzymes are usually very specific and have evolved over millions of years, along with the antibiotics that they inactivate. Examples of antibiotics that are enzymatically inactivated are penicillin, chloramphenicol, and kanamycin.

Resistance can also occur by modifying or overproducing the target site. The target molecule of the antibiotic is either mutated or chemically modified so that it no long binds the antibiotic. This is possible only if modification of the target does not interfere with normal cellular functions. Target site overproduction is less common but can also produce cells that are resistant to antibiotics.

Lastly, target bypass is a mechanism by which microorganisms can become resistant to antibiotics. In bypass mechanisms, two metabolic pathways or targets exist in the cell and one is not sensitive to the antibiotic. Treatment with the antibiotic selects cells with more reliance on the second, antibiotic-resistant pathway.

Among these mechanisms, the greatest concern for new antibiotic development is target site modification. Enzymatic inactivation and specific transport mechanisms require the existence of a substrate specific enzyme to inactivate or transport the antibiotic out of the cell. Enzymes have evolved over millions of years in response to naturally occurring antibiotics. Since microorganisms cannot spontaneously generate new enzymes, these mechanisms are unlikely to pose a significant threat to the development of new synthetic antibiotics. Target bypass only occurs in cells where redundant metabolic pathways exist. As understanding of the MDR transporters increases, it is increasingly possible to develop drugs that are not transported out of the cell by them. Thus, target site modification poses the greatest risk for the development of antibiotic resistance for new classes of antibiotic and this is particularly true for those antibiotics that target ribosomes. The only new class of antibiotics in thirty-five years, the oxazolidinones, is a recent example of an antibiotic that has been compromised because of target site modification. Resistant strains containing a single mutation in rRNA developed within seven months of its use in the clinical settings.

SUMMARY

The "instant evolution" system was initially developed in E. coli primarily because of the ease with which this organism can be genetically manipulated. [WO 2004/003511.] Because many of the functionally important regions of rRNA are conserved among bacteria, drug leads developed against conserved targets in the E. coli system may produce broad-spectrum anti-infectives. However, in order to develop a system to produce narrow-spectrum anti-infectives, provided herein are methods and compositions for screening Pseudomonas aeruginosa 16S rRNA in E. coli cells. In certain embodiments, a plasmid comprising the 16S rRNA gene from Pseudomonas aeruginosa, mutated to replace the natural helix 9 region with the corresponding region of the E. coli rRNA, is provided to form functional ribosomes in E. coli host cells. In other embodiments, a plasmid, comprising the unmutated 16S rRNA from Pseudomonas aeruginosa, along with a plasmid containing the Pseudomonas aeruginosa S20 protein, is provided which can yield functional ribosomes in E. coli cells.

BRIEF DESCRIPTION OF THE FIGURES

FIG. 1 depicts the plasmid construct Pa 16S pRNA228, wherein the E. coli 16S is replaced with the P. aeruginosa between the E. coli BclI and EstEII sites. The locations of specific sites in Pa 16S pRNA228 are as follows: the 16S rRNA E. coli rrnB operon corresponds to nucleic acids 1-14 & 1499-1536; the 16S rRNA P. aeruginosa rrnC operon corresponds to nucleic acids 15-1498; the 16S MBS (message binding sequence) GGGAU corresponds to nucleic acids 1530-1534; the 16S-23S spacer region corresponds to nucleic acids 1537-1976; the 23S rRNA of E. coli rrnB operon corresponds to nucleic acids 1977-4880; the 23S-5S spacer region corresponds to nucleic acids 4881-4972; the 5S rRNA of E. coli rrnB operon corresponds to nucleic acids 4973-5092; the terminator T1 of E. coli rrnB operon corresponds to nucleic acids 5096-5139; the terminator T2 of E. coli rrnB operon corresponds to nucleic acids 5271-5299; the bla (β-lactamase; ampicillin resistance) corresponds to nucleic acids 6462-7319; the replication origin corresponds to nucleic acids 7482-8096; the rop (Rop protein) corresponds to nucleic acids 8509-8700; the GFP corresponds to nucleic acids 9113-10088; the GFP RBS (ribosome binding sequence) AUCCC corresponds to nucleic acids 10096-10100; the trp$^c$ promoter corresponds to nucleic acids 10117-10157; the trp$^c$ promoter corresponds to nucleic acids 10632-10672; the CAT RBS AUCCC corresponds to nucleic acids 10689-10693; the cam (chloramphenicol acetyltransferase: CAT) corresponds to nucleic acids 10701-11630; the lacI$^q$ promoter corresponds to nucleic acids 11670-11747; the lacI$^q$ (lac repressor) corresponds to nucleic acids 11748-12830; and the lacUV5 promoter corresponds to nucleic acids 12873-12914.

FIG. 5 depicts the results of green fluorescent protein (GFP) assays for P. aeruginosa constructs.

FIGS. 6a-f depict the sequence of the plasmid depicted in FIG. 1 (SEQ ID NO: 3).

FIGS. 7a-f depict the sequence of the plasmid depicted in FIG. 2 (SEQ ID NO: 4).

FIGS. 8a-b depict the sequence of the plasmid depicted in FIG. 3 (SEQ ID NO: 5).

FIGS. 9a-b depict the sequence of the plasmid depicted in FIG. 4 (SEQ ID NO: 6).

FIG. 10 depicts novel mutant anti-Shine-Dalgarno (ASD) sequences (SEQ ID NOs: 8, 10, 12, 14, 16, 18, 20, 22, 24, 26, 28, 30 and 32) and novel mutant Shine-Dalgarno (SD) sequences (SEQ ID NOs: 7, 9, 11, 13, 15, 17, 19, 21, 23, 25, 27, 29, and 31) of the present invention. FIG. 10 also shows a sequence analysis of chloramphenicol resistant isolates. The mutated nucleotides are underlined and potential duplex formations are boxed. CAT activity was measured twice for each culture and the unit is CPM/0.1 µL of culture/OD600. Induction was measured by dividing CAT activity in induced cells with CAT activity in uninduced cells. A −1 indicates no induction, while a +1 indicates induction with 1 mM IPTG.

FIG. 11 depicts novel mutant ASD sequences (SEQ ID NOs: 34, 36, 38, 40, 42, 44, 46 and 48) and novel mutant SD sequences (SEQ ID NOs: 33, 35, 37, 39, 41, 43, 45 and 47), of the present invention. FIG. 11 also shows a sequence analysis of CAT mRNA mutants (SEQ ID NOs: 34, 36, 38, 40, 42, 44, 46 and 48). Potential duplex formations are boxed and the mutated nucleotides are underlined. The start codon (AUG) is in bold. A −1 indicates no induction, while a +1 indicates induction with 1 mM IPTG.

FIGS. 12a-b depicts novel mutant ASD sequences (FIG. 12 a-1: SEQ ID NOs: 50, 52, 54, 56 and 58, FIG. 12 a-2: SEQ ID NOs: 60, 62, 64, 66, 68, 70, 72, 74, 76, 78 and 80, FIG. 12 a-3: 82, 84, 86, 88, 90, 92, 94, 96, 98 and 100, FIG. 12 b-1: 102, 104, and 106, FIG. 12 b-2: 108, 110, 112, 114, 116, 118, 120, 122, 124, 126, and 128, FIG. 12-b3: 130, 132, 134, 136, 138, 140, 142, 144, 146 and 148) and novel mutant SD sequences (FIG. 12 a-1: SEQ ID NOs: 49, 51, 53, 55, and 57, FIG. 12 a-2: SEQ ID NOs: 59, 61, 63, 65, 67, 69, 71, 73, 75, 77 and 79, FIG. 12 a-3: 81, 83, 85, 87, 89, 91, 93, 95, 97 and 99, FIG. 12 b-1: 101, 103 and 105, FIG. 12 b-2: 107, 109, 111, 113, 115, 117, 119, 121, 123, 125, and 127, FIG. 12 b-3: 129, 131, 133, 135, 137, 139, 141, 143, 145 and 147) of the present invention.

FIG. 14 depicts a tabulation of 16s rRNA hybrid *P. aeruginosa* and *E. coli* sequences and the resulting measured GFP percentage. (GFP 100% was set for *E. coli* sequence with no *P. aeruginosa* sequence.) The last entry in the table demonstrates the significance of nucleotides 176-188; this is shown pictorially in FIG. 15.

Figure 2B:
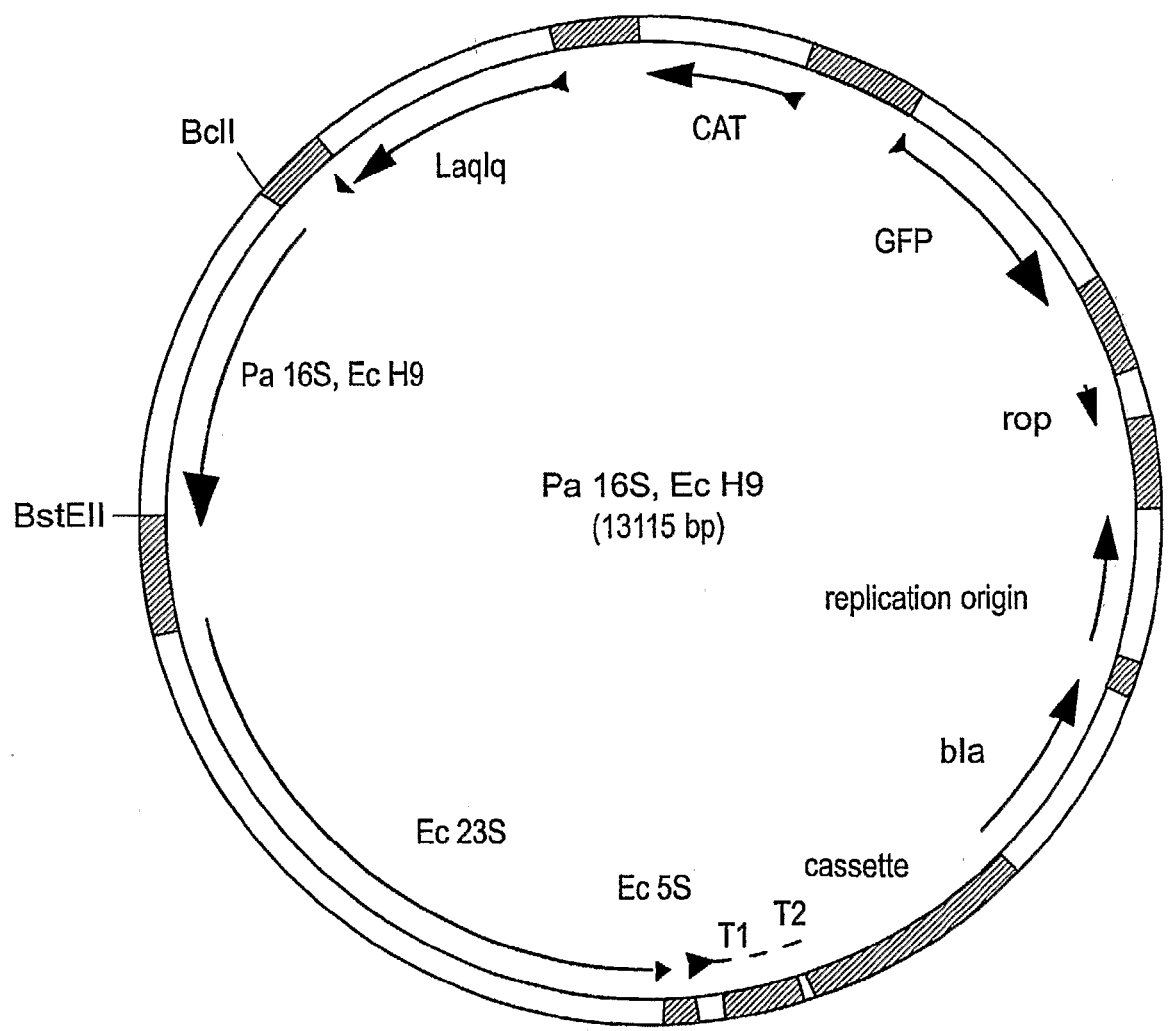
FIG. 2 depicts the plasmid construct Pa 16S Ec H9 pRNA228 wherein the E. coli 16S is replaced with the P. aeruginosa between the E. coli BclI and EstEII sites and the P. aeruginosa helix 9 (H9) sequence is replaced with the E. coli H9 sequence. In other words, the plasmid is made up of E. coli rRNA sequence at positions 1-14, 176-188 and 1499-1536; and P. aeruginosa rRNA sequence at positions 15-175 and 189-1489. The E. coli H9 sequence is AUAACGUCG-CAAGACCAAA (SEQ ID NO: 1) and the P. aeruginosa H9 sequence is AUACGUCCUGAGGGAGAAA (SEQ ID NO: 2). 10 mutations were made and they are denoted with an underline in the P. aeruginosa H9 sequence shown above.

In addition, FIGS. 1-26 of WO 2004/003511 (some of which may also be found in Lee, K., et al. Genetic Approaches to Studying Protein Synthesis: Effects of Mutations at Pseudouridine 516 and A535 in *Escherichia coli* 16S rRNA. Symposium: Translational Control: A. Mechanistic Perspective at the Experimental Biology 2001 Meeting (2001); and Lee, K., et al., J. Mol. Biol. 269: 732-743 (1997)) are expressly incorporated herein by reference.

DETAILED DESCRIPTION

Overview. The "instant evolution" system (as described in WO 2004/003511; herein incorporated by reference in its entirety) was initially developed in *E. coli*, primarily because of the ease with which this organism can be genetically manipulated. Because many of the functionally important regions of rRNA are conserved among bacteria, drug leads developed against conserved targets in the *E. coli* system may produce broad-spectrum anti-infectives.

Recently, however, emphasis has been placed on the development of narrow spectrum antimicrobials because of the reduced likeliness of adverse effects and because resistance to narrow-spectrum antibiotics is less likely to occur. Several rRNA genes from human pathogens were therefore tested to see whether their genes could be expressed in *E. coli*.

Compositions and Methods of the Invention. In one embodiment, compositions and methods are provided to identify functional mutant *P. aeruginosa* ribosomes suitable as drug targets. The compositions and methods of the invention allow for the expression of *P. aeruginosa* ribosomes in *E. coli*. The compositions and methods further allow for the isolation and analysis of mutations that would normally be lethal and allow direct selection of rRNA mutants with predetermined levels of ribosome function. The compositions and methods of the present invention may additionally be used to identify antibiotics to treat generally and/or selectively, human pathogens such as *P. aeruginosa*.

According to one embodiment of the invention, a functional genomics database for 16S rRNA genes of a variety of species is generated. In particular, the rRNA gene is randomly mutated using a generalized mutational strategy. A host *E. coli* cell is then transformed with a mutagenized plasmid of the invention comprising: an *P. aeruginosa* rRNA gene having a mutant ASD sequence, the mutated *P. aeruginosa* rRNA gene, and a genetically engineered gene which encodes a selectable marker having a mutant SD sequence. In certain embodiments, said *P. aeruginosa* DNA is further modified so as to replace helix 9 with the corresponding *E. coli* helix (FIG. 15); in other embodiments the host cell is further transformed with a plasmid encoding the *P. aeruginosa* S20 gene. The selectable marker gene, such as CAT, may be used to select mutants that are functional, e.g., by plating the transformed cells onto growth medium containing chloramphenicol. The mutant rRNA genes contained in each plasmid DNA of the individual clones from each colony are selected and characterized. The function of each of the mutant rRNA genes is assessed by measuring the amount of an additional selectable marker gene, such as GFP, produced by each clone upon induction of the rRNA operon. A functional genomics database may thus be assembled, which contains the sequence and functional data of the functional mutant rRNA genes. In particular, functionally important regions of the rRNA gene that will serve as drug targets are identified by comparing the sequences of the functional genomics database and correlating the sequence with the amount of GFP protein produced.

In another embodiment, the nucleotides in the functionally important target regions identified in the above methods may be simultaneously randomly mutated, e.g., by using standard methods of molecular mutagenesis, and cloned into a plasmid of the invention to form a plasmid pool containing random mutations at each of the nucleotide positions in the target region. The resulting pool of plasmids containing random mutations is then used to transform cells, e.g., *E. coli* cells, and form a library of clones, each of which contains a unique combination of mutations in the target region. The library of mutant clones are grown in the presence of IPTG to induce production of the mutant rRNA genes and a selectable marker is used, such as CAT, to select clones of rRNA mutants containing nucleotide combinations of the target region that produce functional ribosomes. The rRNA genes producing functional ribosomes are sequenced and may be incorporated into a database.

In yet another embodiment, a series of oligonucleotides may be synthesized that contain the functionally-important nucleotides and nucleotide motifs within the target region and may be used to sequentially screen compounds and compound libraries to identify compounds that recognize (bind to) the functionally important sequences and motifs. The compounds that bind to all of the oligonucleotides are then counter-screened against oligonucleotides and/or other RNA containing molecules to identify drug candidates. Drug candidates selected by the methods of the present invention are thus capable of recognizing all of the functional variants of the target sequence, i.e., the target cannot be mutated in a way that the drug cannot bind, without causing loss of function to the ribosome.

In still another embodiment, after the first stage mutagenesis of the entire rRNA is performed using techniques known in the art, e.g., error-prone PCR mutagenesis, the mutants are analyzed to identify regions within the rRNA that are important for function. These regions are then sorted based on their phylogenetic conservation, as described herein, and are then used for further mutagenesis.

Ribosomal RNA sequences from each species are different and the more closely related two species are, the more their rRNAs are alike. For instance, humans and monkeys have very similar rRNA sequences, but humans and bacteria have very different rRNA sequences. These differences may be utilized for the development of very specific drugs with a narrow spectrum of action and also for the development of broad-spectrum drugs that inhibit large groups of organisms that are only distantly related, such as all bacteria.

In another embodiment, the functionally important regions identified above are divided into groups based upon whether or not they occur in closely related groups of organisms. For instance, some regions of rRNA are found in all bacteria but not in other organisms. Other areas of rRNA are found only in closely related groups of bacteria, such as all of the members of a particular species, e.g., members of the genus *Mycobacterium* or *Streptococcus*.

In a further embodiment, the regions found in very large groups of organisms, e.g., all bacteria or all fungi, are used to develop broad-spectrum antibiotics that may be used to treat infections from a large number of organisms within that group. The methods of the present invention may be performed on these regions and functional mutant ribosomes identified. These functional mutant ribosomes may be screened, for example, with compound libraries.

In yet another embodiment, regions that are located only in relatively small groups of organisms, such as all members of the genus *Streptococcus* or all members of the genus *Mycobacterium*, may be used to design narrow spectrum antibiotics that will only inhibit the growth of organisms that fall within these smaller groups. The methods of the present invention may be performed on these regions and functional mutant ribosomes identified. These functional mutant ribosomes will be screened, e.g., compound libraries.

The invention provides novel plasmid constructs, e.g. those depicted in FIGS. 1 to 4. In addition, the novel plasmid constructs of the present invention employ novel mutant anti-Shrine-Delgarno (ASD) and mutant Shine-Delgarno (SD) sequences set forth in FIGS. 10, 11 and 12. The mutant ASD and mutant SD sequences may be used as mutually compatible pairs (see FIGS. 10, 11 and 12). It will be appreciated that the mutually compatible pairs of mutant ASD and SD sequences interact as pairs in the form of RNA, to permit translation of only the mRNAs containing the altered SD sequence.

Definitions. For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

As used herein, the term "mutation" includes an alteration in the nucleotide sequence of a given gene or regulatory sequence from the naturally occurring or normal nucleotide sequence. A mutation may be a single nucleotide alteration (e.g., deletion, insertion, substitution, including a point mutation), or a deletion, insertion, or substitution of a number of nucleotides.

By the term "selectable marker" is meant a gene whose expression allows one to identify functional mutant ribosomes. Useful selectable markers are well known in the art and include, for example, antibiotic and herbicide resistance genes, gas concentrations, nutrients, and waste products. Specific examples of such genes are disclosed in Weising et al. Weising, K, et al., (1988) Ann Rev of Genetics 22:421-478; the contents of which are incorporated by reference. Examples of selectable marker genes are genes encoding a protein such as G418 and hygromycin which confer resistance to certain drugs, for example, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The term 'Gram-positive bacteria' is an art recognized term for bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium* complex, *Mycobacterium chelonae*, *Mycobacterium fortuitum*, *Mycobacterium haemophilium*, *Mycobacterium kansasii*,

*Mycobacteriuni leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis.*

The term "Gram-negative bacteria" is an art recognized term for bacteria characterized by the presence of a double membrane surrounding each bacterial cell. Representative Gram-negative bacteria include *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chlamydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salinonella typhi, Serratia marcescens, Shigella* spp., *Treponema carateum, Treponema pallidum, Treponema pallidum endeinicuin, Treponema pertenue, Veillonella* spp., *Vibrio cholerae, Vibrio vulnificus, Yersinia enterocolitica, Yersinia pestis.*

Isolated Nucleic Acid Molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium, when produced by recombinant techniques, or substantially free of chemical precursors or other chemicals when chemically synthesized.

Figure 12A-2:
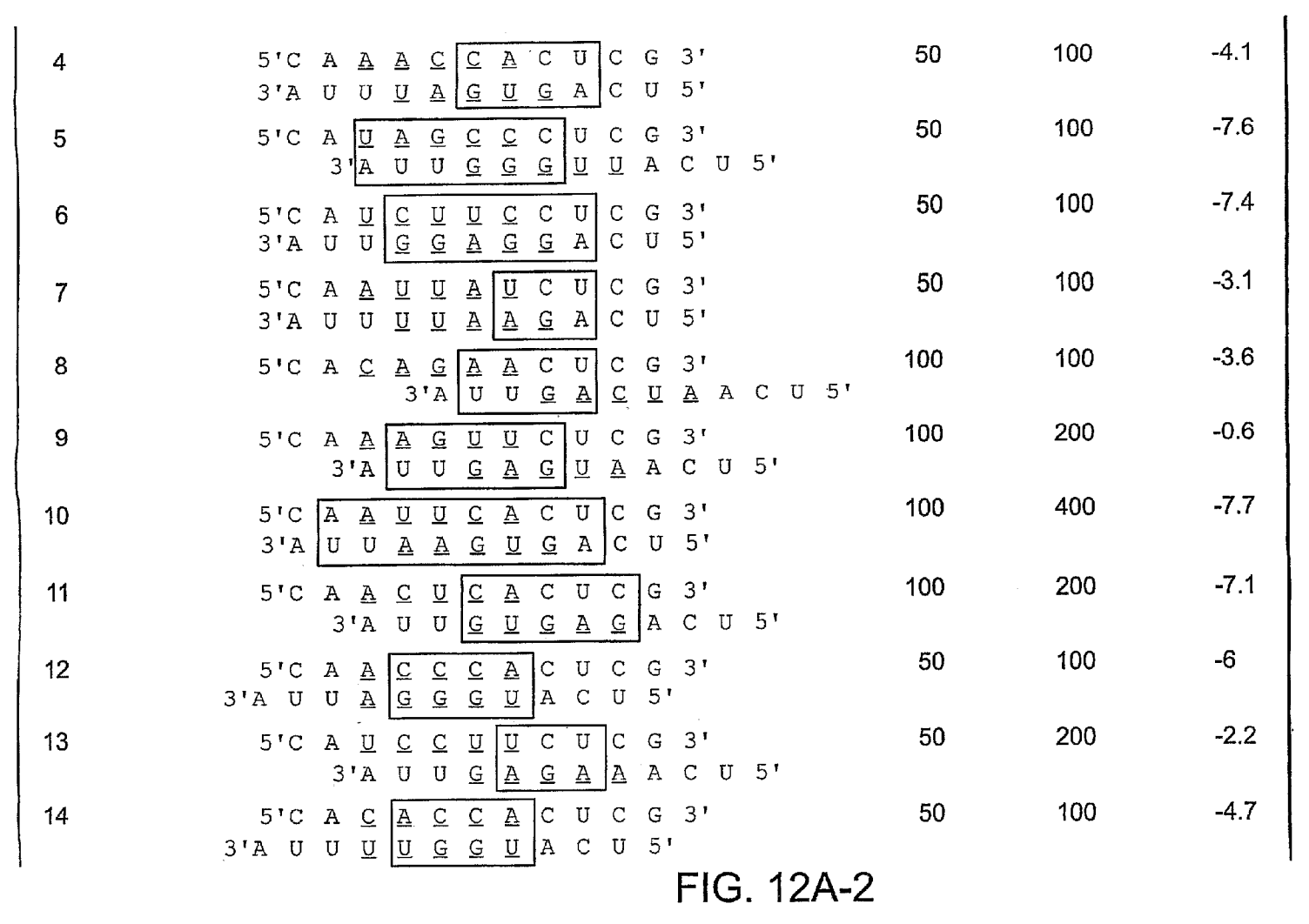

A nucleic acid molecule of the present invention, e.g., a nucleic acid molecule having the nucleotide sequence set forth in FIGS. 10, 11, and 12, or a portion thereof, can be isolated using standard molecular biology techniques and the sequence information provided herein. Using all or portion of the nucleic acid sequence set forth in FIGS. 10, 11, and 12 as a hybridization probe, the nucleic acid molecules of the present invention can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of the sequence set forth in FIGS. 10, 11, and 12, can be isolated by the polymerase chain reaction (PCR) using synthetic oligonucleotide primers designed based upon the sequence set forth in FIGS. 10, 11, and 12.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequences of the present invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence set forth in FIGS. 10, 11, and 12, or a portion of any of these nucleotide sequences. A nucleic acid molecule which is complementary to the nucleotide sequence shown in FIGS. 10, 11, and 12 is one which is sufficiently complementary to the nucleotide sequence shown in FIGS. 10, 11, and 12, such that it can hybridize to the nucleotide sequence shown in FIGS. 10, 11, and 12, respectively, thereby forming a stable duplex.

"Homology" or alternatively "identity" refers to sequence similarity between two nucleic acid molecules. Homology may be determined by comparing a position in each sequence, which may be aligned for purposes of comparison. When a position in the compared sequence is occupied by the same base, then the molecules are homologous at that position. A degree of homology between sequences is a function of the number of matching or homologous positions shared by the sequences.

The term "percent identical" refers to sequence identity between two nucleotide sequences. Identity may be determined by comparing a position in each sequence, which may be aligned for purposes of comparison. When an equivalent position in the compared sequences is occupied by the same base or amino acid, then the molecules are identical at that position; when the equivalent site is occupied by the same or a similar base (e.g., similar in steric and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and may be used with, e.g., default settings. ENTREZ is available through the National Center for Biotechnology Information, National Library of Medicine, National Institutes of Health, Bethesda, Md. In one embodiment, the percent identity of two sequences may be determined by the GCG program with a gap weight of 1, e.g., each nucleic acid gap is weighted as if it were a single nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method may be utilized to align sequences. An alternative search strategy uses MPSRCH software, which runs on a MASPAR computer. MPSRCH uses a Smith-Waterman algorithm to score sequences on a massively parallel computer. This approach improves the ability to pick up distantly related matches, and is especially tolerant of small gaps and nucleotide sequence errors. Nucleic acid-encoded amino acid sequences may be used to search both protein and DNA databases. Databases with individual sequences are described in *Methods in Enzymology*, ed. Doolittle, supra. Databases include Genbank, EMBL, and DNA Database of Japan (DDBJ).

The terms "polynucleotide", and "nucleic acid" are used interchangeably to refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semi-synthetic, or synthetic origin, which either does not occur in nature or is linked to another polynucleotide in a non-natural arrangement. An "oligonucleotide" refers to a single stranded polynucleotide having less than about 100 nucleotides, less than about, e.g., 75, 50, 25, or 10 nucleotides.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions, which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available in which G-C stacking interactions, solvent effects, the desired assay temperature and the like are taken into account. For example, probes can be designed to have a dissociation temperature (Td) of approximately 60° C., using the formula: $Td=(((((3\times\#GC)+(2\times\#AT))\times37)-562)/\#bp)-5$; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution comprising, or consisting of, 50% formamide, 10×Denhardt (0.2% Ficoll, 0.2% Polyvinylpyrrolidone, 0.2% bovine serum albumin) and 200 µg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, N.Y.; and Tibanyenda, N. et al., Eur. J. Biochem. 139:19 (1984) and Ebel, S. et al., Biochem. 31:12083 (1992).

The term "substantially homologous" when used in connection with a nucleic acid or amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

Recombinant Expression Vectors and Host Cells. Another aspect of the invention pertains to vectors, preferably expression vectors, containing a nucleic acid molecule of the present invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al. (1988) Gene 69:301-315) and pET 11d (Studier et al. (1990) Methods Enzymol. 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the expression vector may be a yeast expression vector. Examples of vectors for expression in yeast S. cerevisiae include pYepSec1 (Baldari et al. (1987) Embo J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379).

Another aspect of the invention pertains to host cells into which a the nucleic acid molecule of the invention is introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Nucleic acid encoding a selectable marker can be introduced into a host cell on the same vector as that encoding a protein or can be introduced on a separate vector. Cells stably transfected with the introduced nucleic acid can be identified by drug selection (e.g., cells that have incorporated the selectable marker gene will survive, while the other cells die).

Making *P. aeruginosa* 16S rRNA active in *E. coli*. As already mentioned herein, a plasmid comprising the 16S rRNA gene from *P. aeruginosa*, mutated to replace the natural helix 9 region with the corresponding region of the *E. coli* rRNA, is provided to form functional mutant ribosomes. In addition, in certain embodiments, a plasmid comprising the *Pseudomonas aeruginosa* S20 protein is provided, thereby yielding functional ribosomes in *E. coli* cells.

There are many different ribosomal proteins. The 30S ribosomal proteins are designated S1-S21. It is known that S4, S7, S8, S15, S17 and S20 bind independently to 16S rRNA. Binding of these primary binding proteins folds the rRNA and allows binding of the secondary binding proteins (S5, S6, S9, S12, S13, S16, S18, and S19). These proteins also fold the ribosome to allow the addition of S2, S3, S10, S11, S14 and S21 (which are known as tertiary binding proteins).

Figure 16:
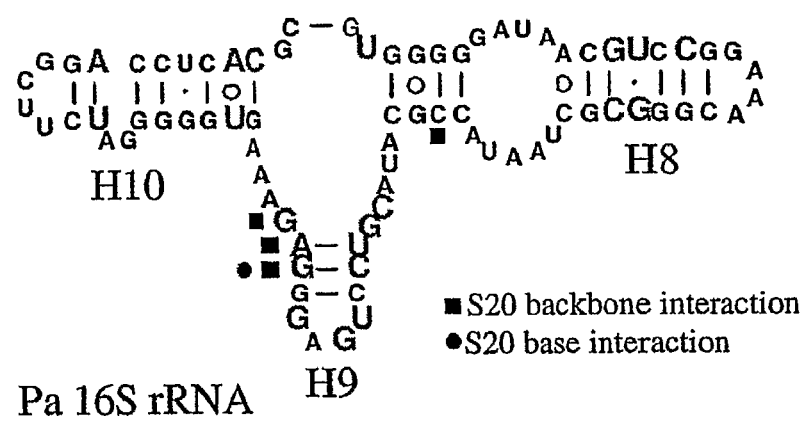
FIG. 16 depicts the ribosomal protein S20 binding site on *P. aeruginosa* 16S rRNA (SEQ ID NO: 152).
Figure 17:
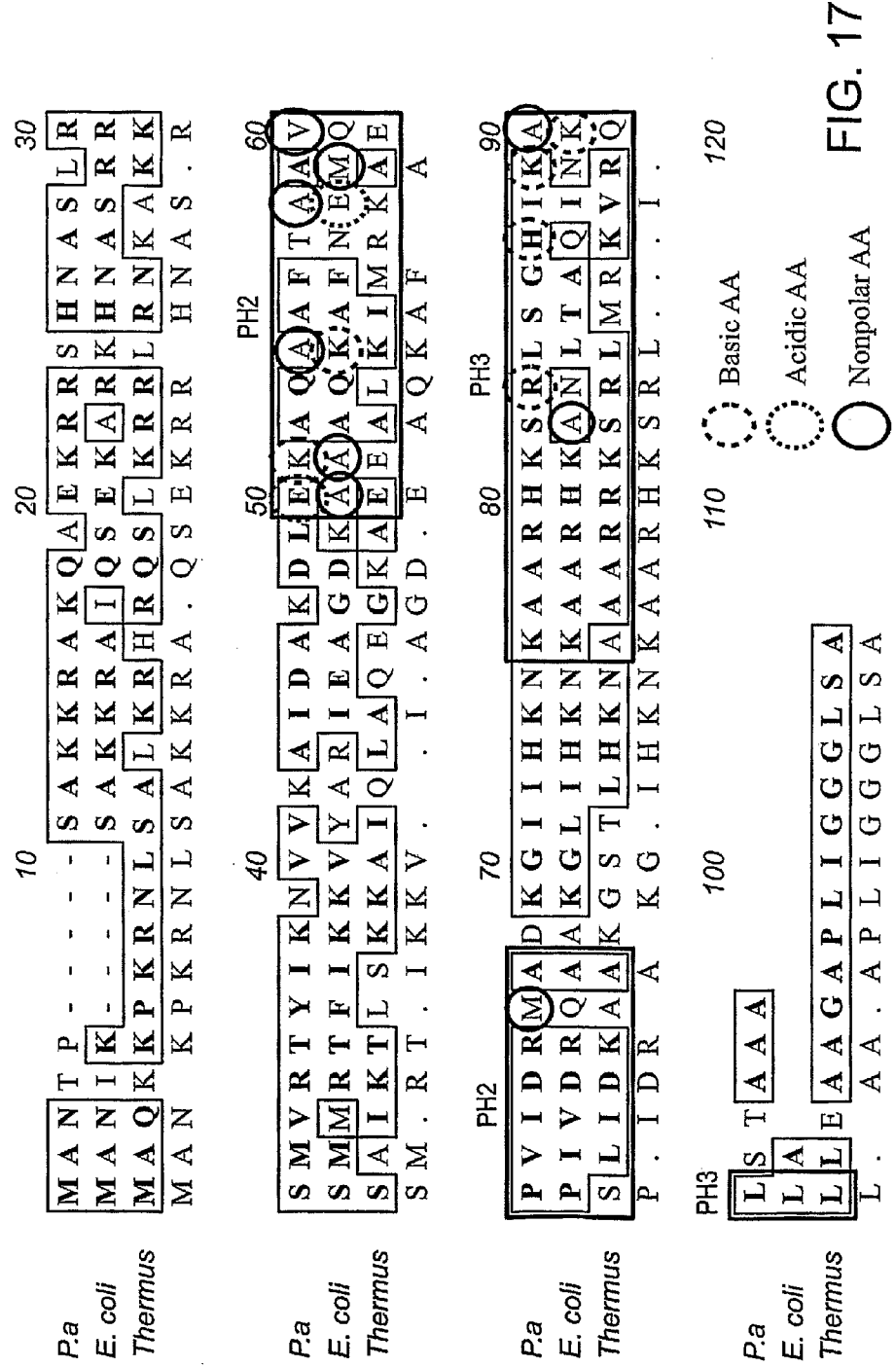
FIG. 17 depicts an S20 protein alignment of *E. coli* (SEQ ID NO: 154) compared with *P. aeruginosa* (SEQ ID NO: 153) and *Thermus* species (SEQ ID NO: 155).

The ribosomal protein S20 binding site on *P. aeruginosa* are shown in FIG. 16. 16S rRNA Protein alignments for *E. coli* and *P. aeruginosa* are shown in FIG. 17. As shown therein, S20's pH2 and pH3 interact with H9 of the 16S rRNA. It is hypothesized that charge differences between *E. coli* and *P. aeruginosa* S20 composition may play a role in binding of the protein to the rRNA.

Figure 18:
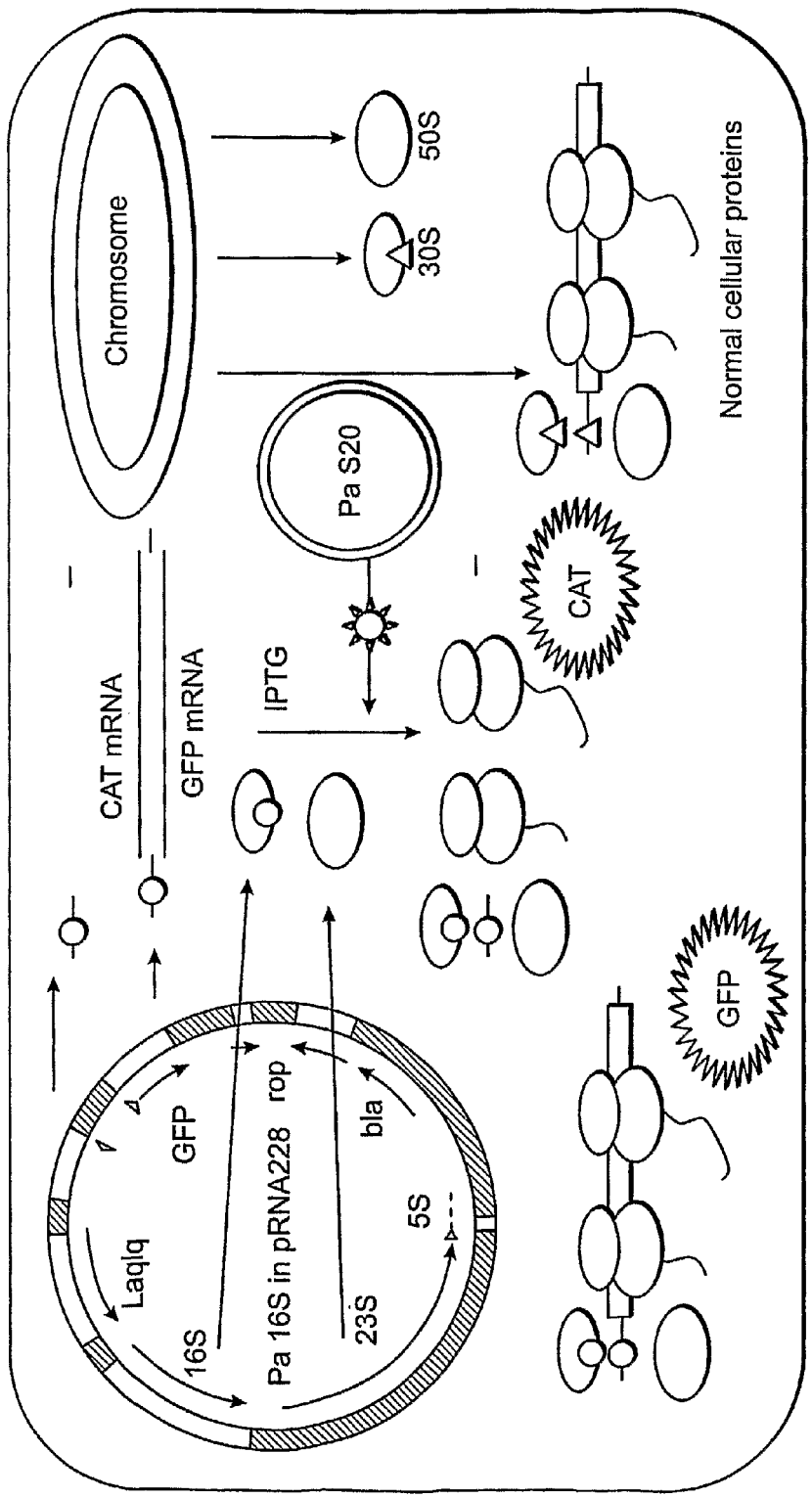
FIG. 18 depicts a schematic of the addition of a plasmid containing the S20 gene into transformed in cells containing the 16S rRNA of *E. coli* and *P. aeruginosa*, and the measurement of resulting activity by GFP.

The expression of *P. aeruginosa* S20 can be made in the presence of *E. coli* and *P. aeruginosa* 16S RNA. One begins by obtaining chromosomal DNA from *P. aeruginosa*. Then the S20 gene is PCRed. Next, this gene is cloned into an expression vector. Finally, the plasmid containing the S20 gene is transformed in cells (e.g. DH5 cells) containing the 16S rRNA of *E. coli* and *P. aeruginosa*, and the activity is measured. A schematic of this process is shown in FIG. 18. GFP analysis of *P. aeruginosa* (46% activity of ribosomes without *P. aeruginosa* S20 and 96.4% activity of ribosomes with *P. aeruginosa* S20) confirms that *P. aeruginosa* 16S rRNA is complemented by *P. aeruginosa* S20. When the vector only was assayed (i.e. no S20) no increase in ribosomal activity was observed.

*P. aeruginosa* 16S rRNAs may therefore be made active in *E. coli* by replacing helix 9 of *P. aeruginosa* 16S rRNA with the corresponding sequence from *E. coli* or by adding *P. aeruginosa* S20 to cells that are making the *P. aeruginosa* 16S rRNA. Both constructs can be used to develop antibiotics that target *P. aeruginosa* 16S rRNA.

Making other pathogen's 16S rRNA active in *E. coli*. Given *P. aeruginosa* 16S rRNA can be fully expressed in *E. coli*, it is likely that the rRNAs from other pathogens (e.g. Gram-positive or Gram-negative bacteria) can also be expressed in *E. coli*. This will facilitate the identification of new antibiotic targets, and therefore new classes of antibiotics which are less susceptible to the development of resistance. The inventive system described herein can be used to identify antibiotic leads that disrupt the interaction between critical nucleotides of pathogenic 16S rRNA and the critical amino acids on ribosomal proteins (such as critical nucleotides on *P. aeruginosa* 16S rRNA and *P. aeruginosa* S20). An antibiotic developed in this manner with specifically target the pathogen used, and its close relatives, without effecting other bacteria.

Uses and Methods of the Invention. The nucleic acid molecules described herein may be used in a plasmid construct, e.g. pRNA228, to carry out one or more of the following methods: (1) creation of a functional genomics database of the rRNA genes generated by the methods of the present invention; (2) mining of the database to identify functionally important regions of the rRNA; (3) identification of functionally important sequences and structural motifs within each target region; (4) screening compounds and compound libraries against a series of functional variants of the target sequence to identify compounds that bind to all functional variants of the target sequence; and (5) counterscreening the compounds against nontarget RNAs, such as human ribosomes or ribosomal RNA sequences.

One aspect of the invention relates to a plasmid comprising a first nucleic acid sequence and a second nucleic acid sequence; wherein said first nucleic acid sequence encodes a *Pseudomonas aeruginosa* 16S rRNA comprising a mutant Anti-Shine-Dalgarno sequence and at least one additional mutation outside the Anti-Shine-Dalgarno region; and said second sequence encodes a selectable marker having a mutant Shine-Dalgarno sequence; wherein said mutant Anti-Shine-Dalgarno specifically hybridizes to said mutant Shine-Dalgarno sequence.

Another aspect of the invention relates to the plasmid of FIG. 1.

Another aspect of the invention relates to a plasmid comprising a first nucleic acid sequence and a second nucleic acid sequence; wherein said first nucleic acid sequence encodes a *Pseudomonas aeruginosa* 16S rRNA comprising a mutant Anti-Shine-Dalgarno sequence, a mutant helix 9 sequence, and at least one additional mutation outside the Anti-Shine-Dalgarno region; and said second sequence encodes a selectable marker having a mutant Shine-Dalgarno sequence; wherein said mutant Anti-Shine-Dalgarno specifically hybridizes to said mutant Shine-Dalgarno sequence.

Another aspect of the invention relates to the plasmid of FIG. 2.

In certain embodiments the present invention relates to the aforementioned plasmid, wherein the selectable marker is chosen from the group consisting of chloramphenicol acetyltransferase (CAT), green fluorescent protein (GFP), and both CAT and GFP.

In certain embodiments the present invention relates to the aforementioned plasmid, wherein said mutant helix 9 sequence is SEQ ID NO: 1.

In certain embodiments the present invention relates to the aforementioned plasmid, wherein the mutant Anti-Shine-Dalgarno sequence is selected from the group consisting of the sequences set forth in FIGS. 10, 11 and 12.

In certain embodiments the present invention relates to the aforementioned plasmid, wherein the mutant Shine-Dalgarno sequence is selected from the group consisting of the sequences set forth in FIGS. 10, 11 and 12.

In certain embodiments the present invention relates to the aforementioned plasmid, wherein the mutant Anti-Shine-Dalgarno sequence and the mutant SD sequence are a complementary pair selected from the group consisting of the sequences set forth in FIGS. 10, 11 and 12.

In certain embodiments the present invention relates to the aforementioned plasmid, wherein the complementary mutant Shine-Dalgarno and mutant Anti-Shine-Dalgarno pair permits translation by the rRNA of the selectable marker.

In certain embodiments the present invention relates to the aforementioned plasmid, wherein the selectable marker is CAT.

In certain embodiments the present invention relates to the aforementioned plasmid, wherein the selectable marker is GFP.

In certain embodiments the present invention relates to the aforementioned plasmid, wherein the DNA sequence encoding the rRNA gene is under the control of an inducible promoter.

Another aspect of the invention relates to a plasmid comprising a *Pseudomonas aeruginosa* S20 gene.

Figure 3:
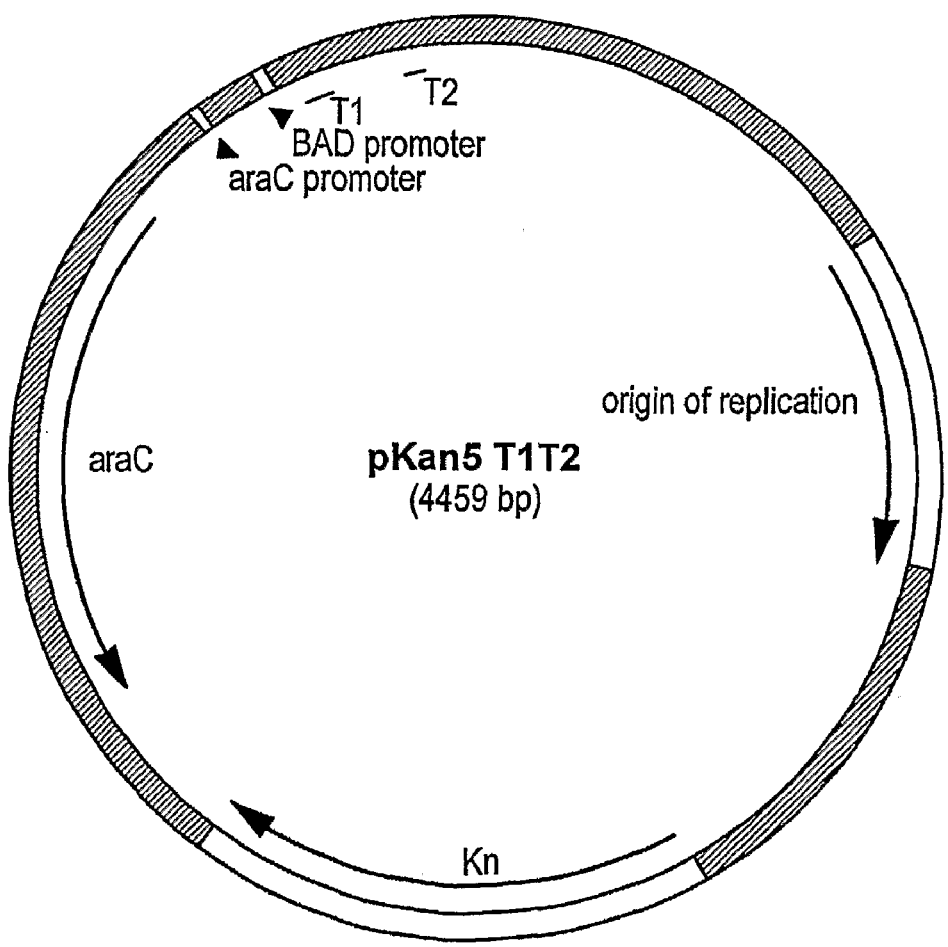
FIG. 3 depicts a pKan5-T1T2 vector wherein the E. coli terminators from pRNA228 were moved (via PCR) into the multicloning site of pKAN5 using restriction enzymes XbaI and EcoRI. The locations of specific sites in pKan5-T1T2 are as follows: the replication origin corresponds to nucleic acids 723-1268; aph (3')-la (kanamycin resistance) corresponds to nucleic acids 1862-2677; araC corresponds to nucleic acids 2950-3828; Pc (the araC promoter) corresponds to nucleic acids 3979-4005; the pBAD promoter corresponds to nucleic acids 4104-4131; the terminator T1 of E. coli rrnB operon corresponds to nucleic acids 4163-4206; and the terminator T2 of E. coli rrnB operon corresponds to nucleic acids 4338-4366.
Figure 4:
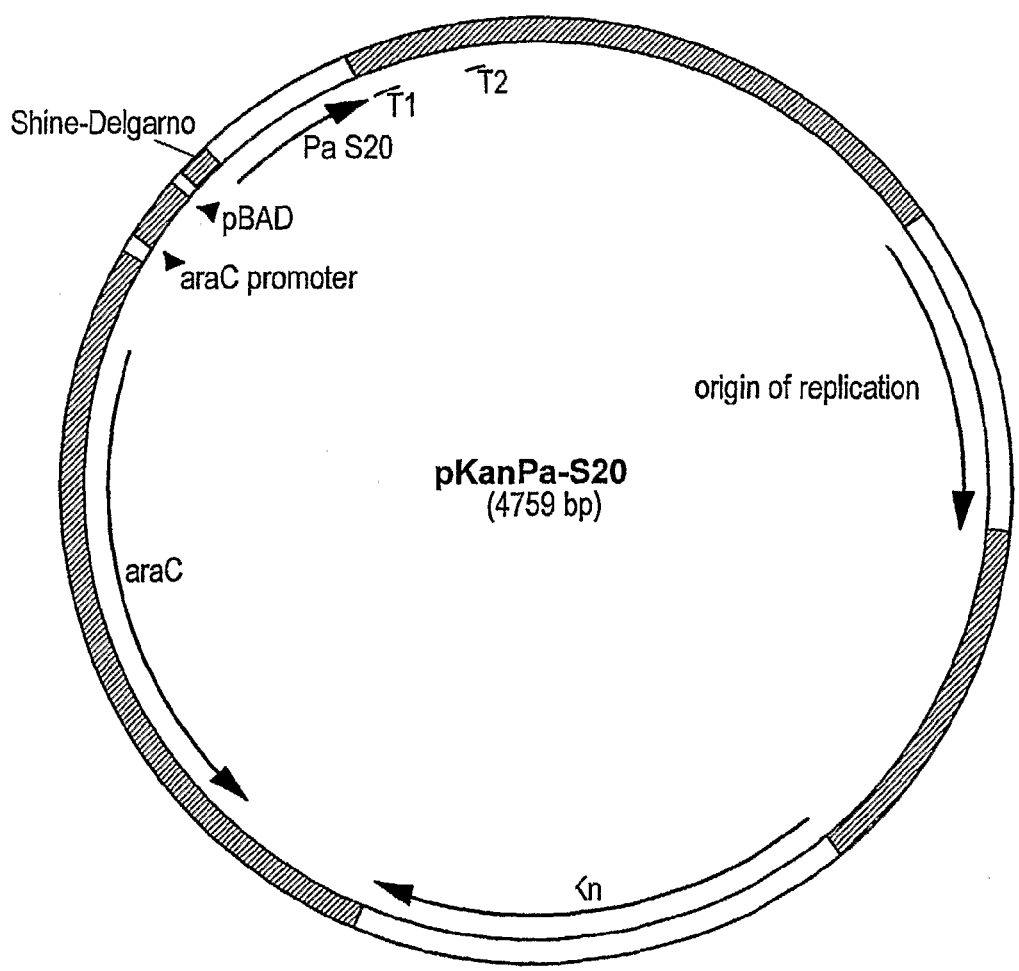
FIG. 4 depicts a pKan5 vector wherein the E. coli terminators from pRNA228 were moved (via PCR) into the multicloning site of pKan5 using restriction enzymes XbaI and EcoRI; and the P. aeruginosa S20 protein was also cloned into the vector using enzymes NotI and XbaI (denoted herein as "pKanPa-S20"). The locations of specific sites in pKan5 Pa-S20 are as follows: the replication origin corresponds to nucleic acids 723-1268; aph (3')-la (kanamycin resistance) corresponds to nucleic acids 1862-2677; araC corresponds to nucleic acids 2950-3828; Pc (the araC promoter) corresponds to nucleic acids 3979-4005; the pBAD promoter corresponds to nucleic acids 4104-4131; the Shine-Dalgarno sequence (GAGGA) corresponds to nucleic acids 4168-4172; P. aeruginosa S20 corresponds to 4181-4453; the terminator T1 of E. coli rrnB operon corresponds to nucleic acids 4463-4506; and the terminator T2 of E. coli rrnB operon corresponds to nucleic acids 4638-4666.
Figure 13:
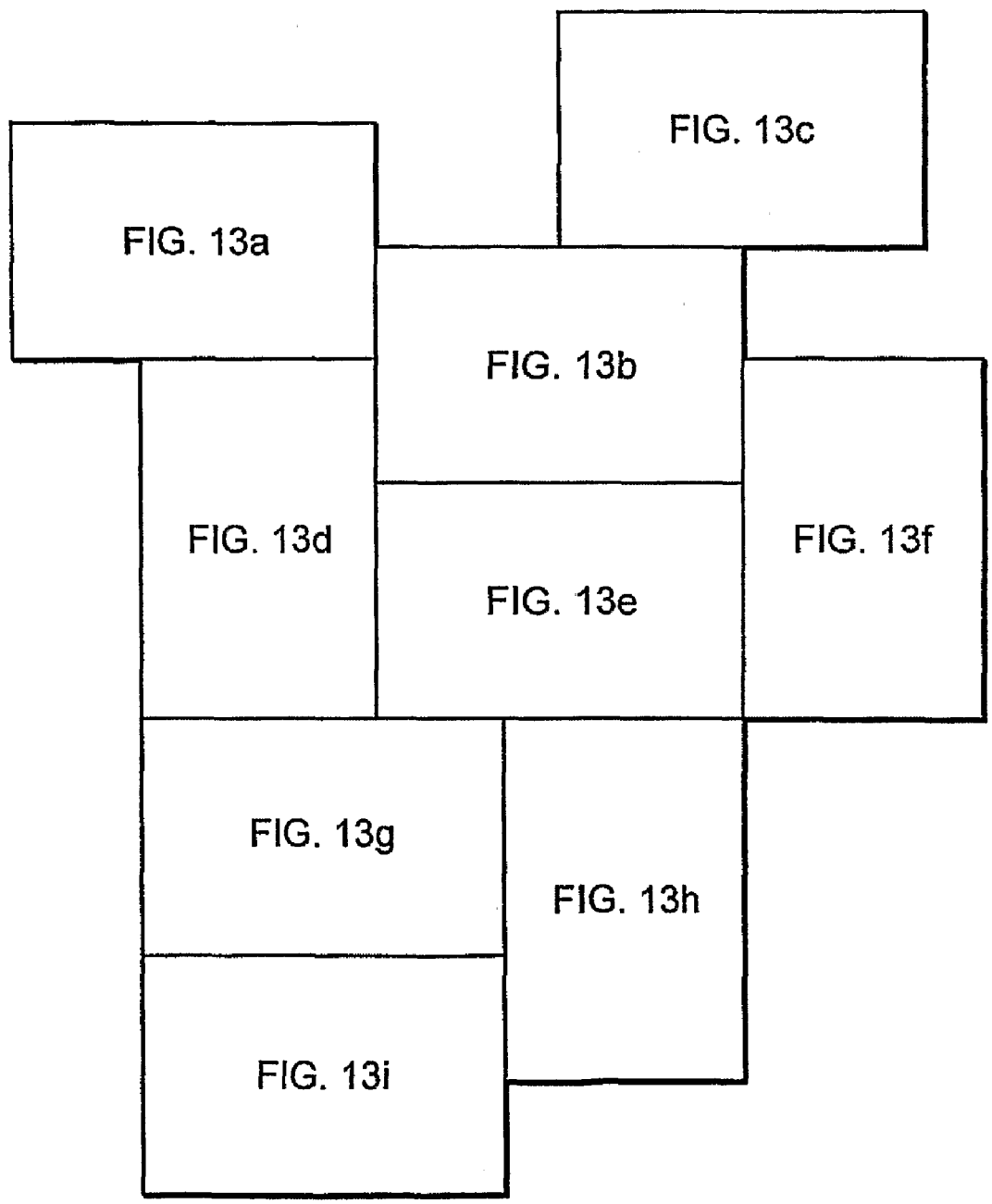
FIG. 13 depicts the nucleotide differences between *E. coli* (SEQ ID NO: 150) and *P. aeruginosa* 16S rRNA (SEQ ID NO: 149). The *P. aeruginosa* 16S rRNA is shown in full, with the *E. coli* sequence differences shown in circles.
Figure 13A:
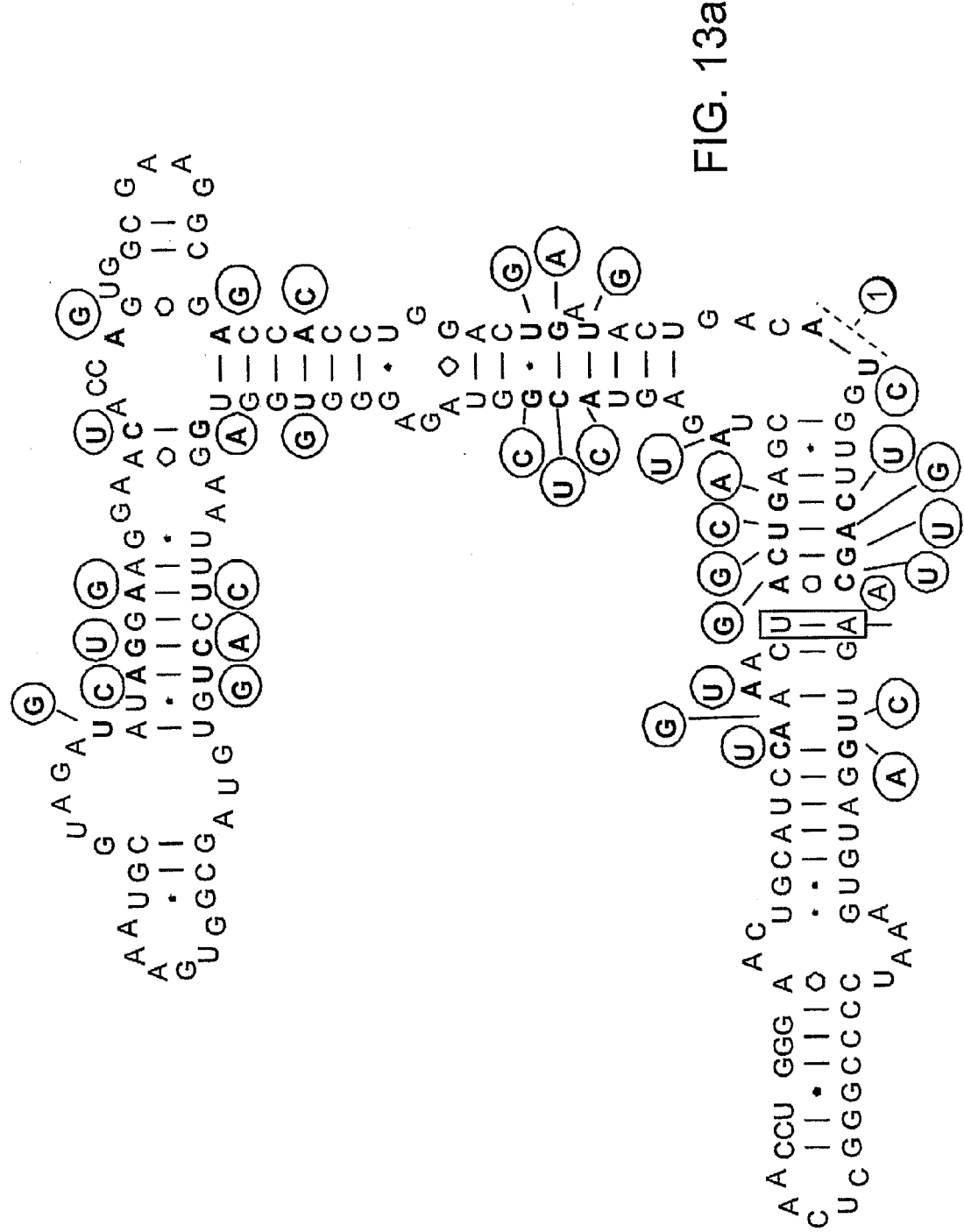
Figure 13B:
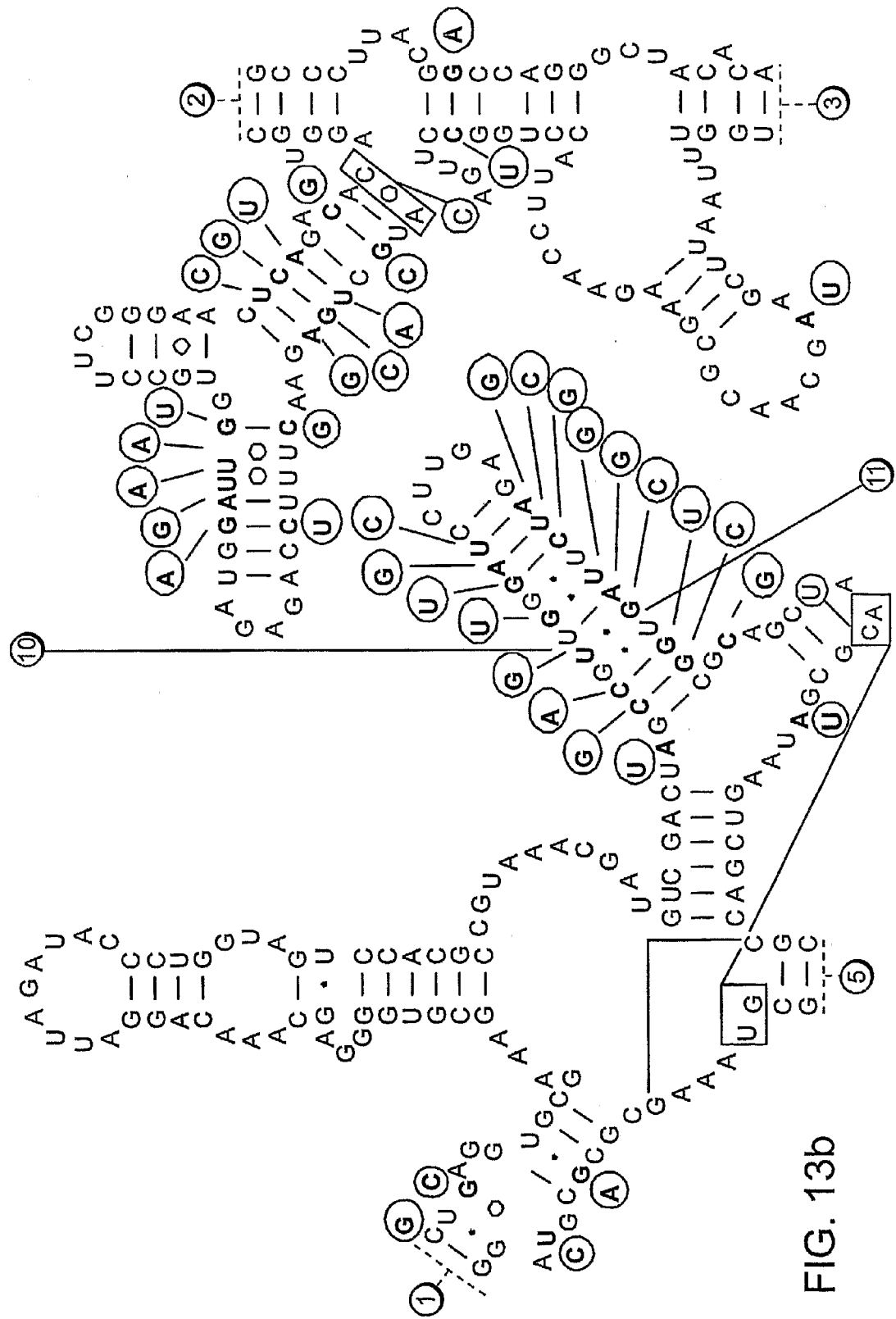
Figure 13C:
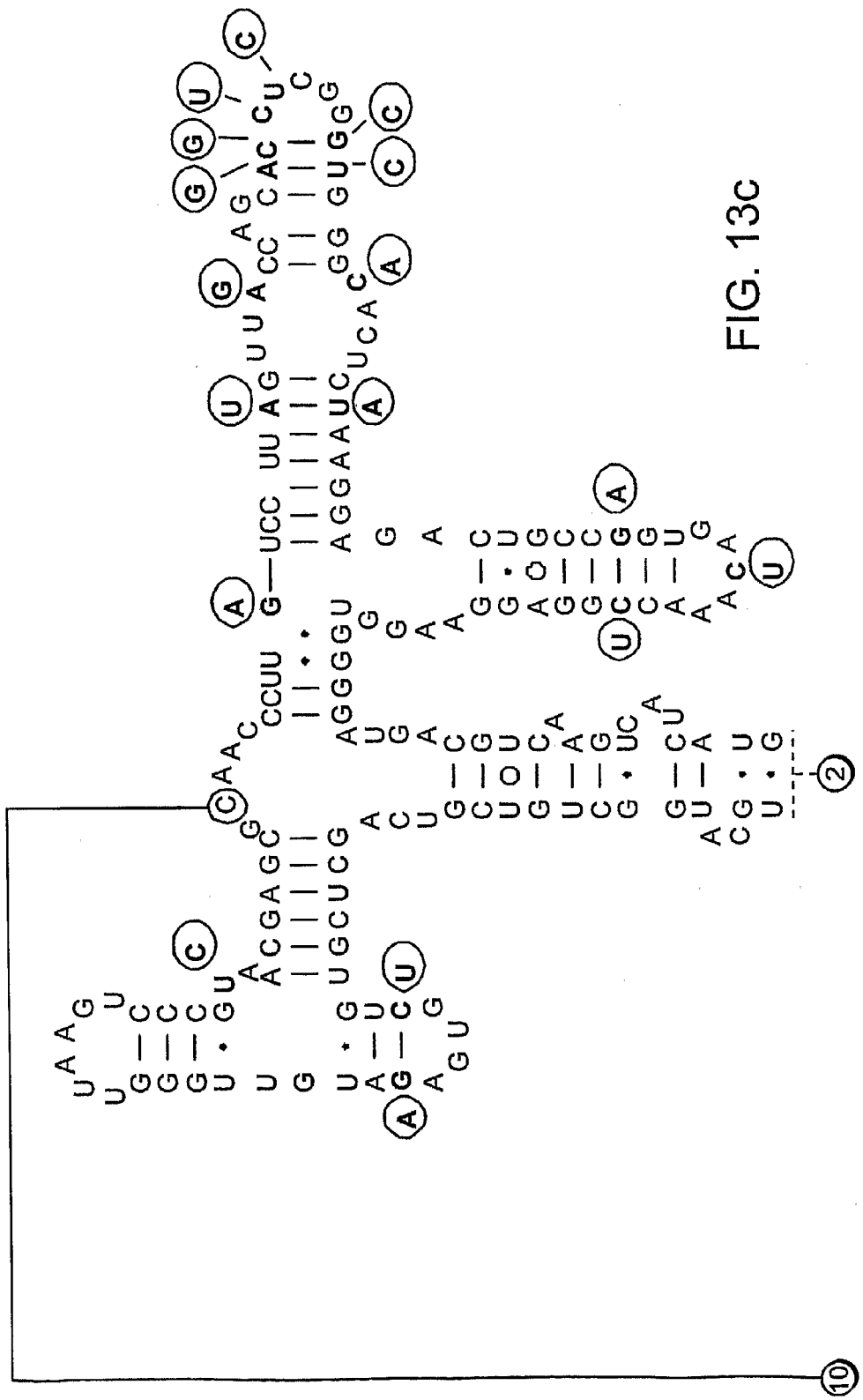
Figure 13D:
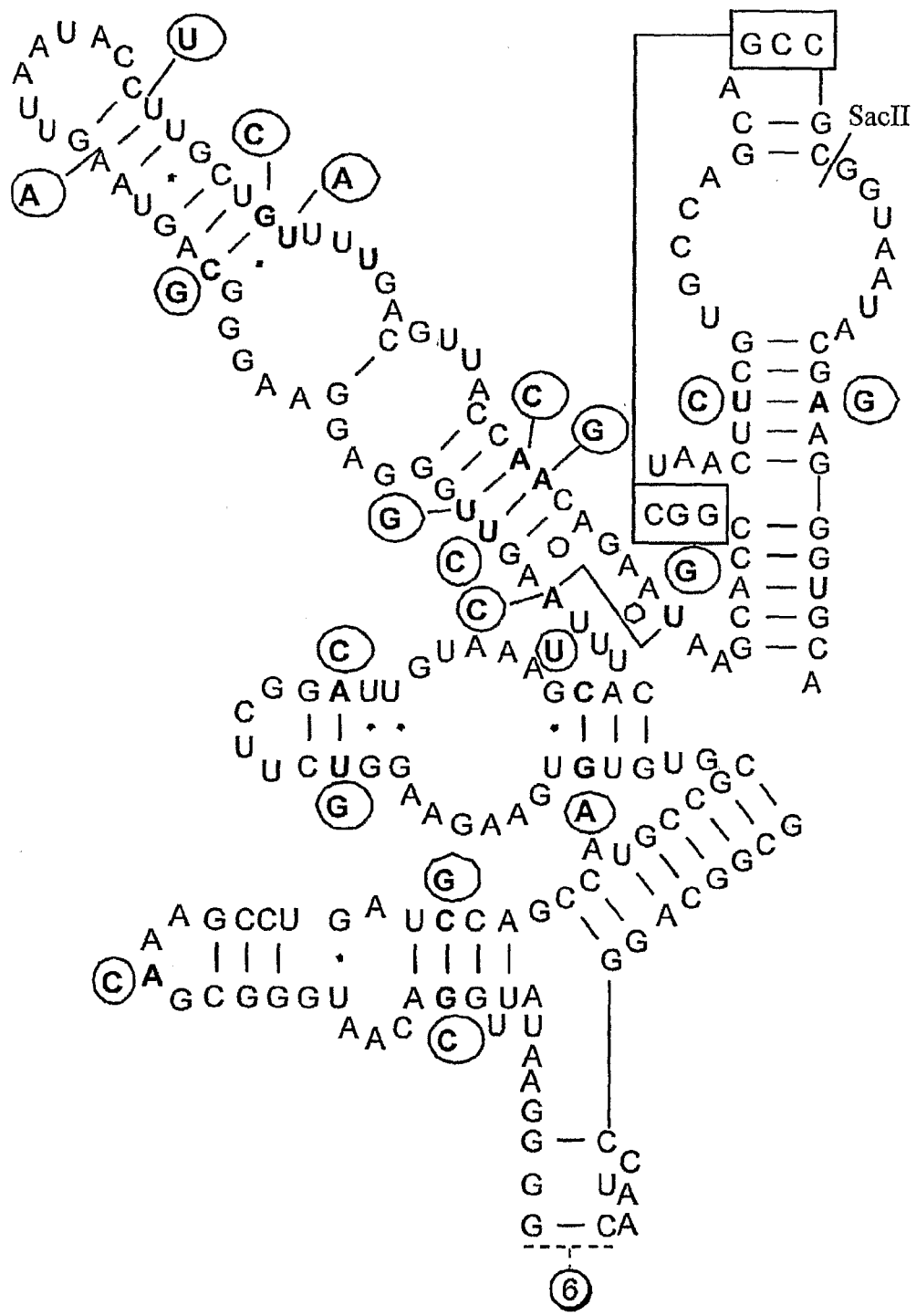
Figure 13E:
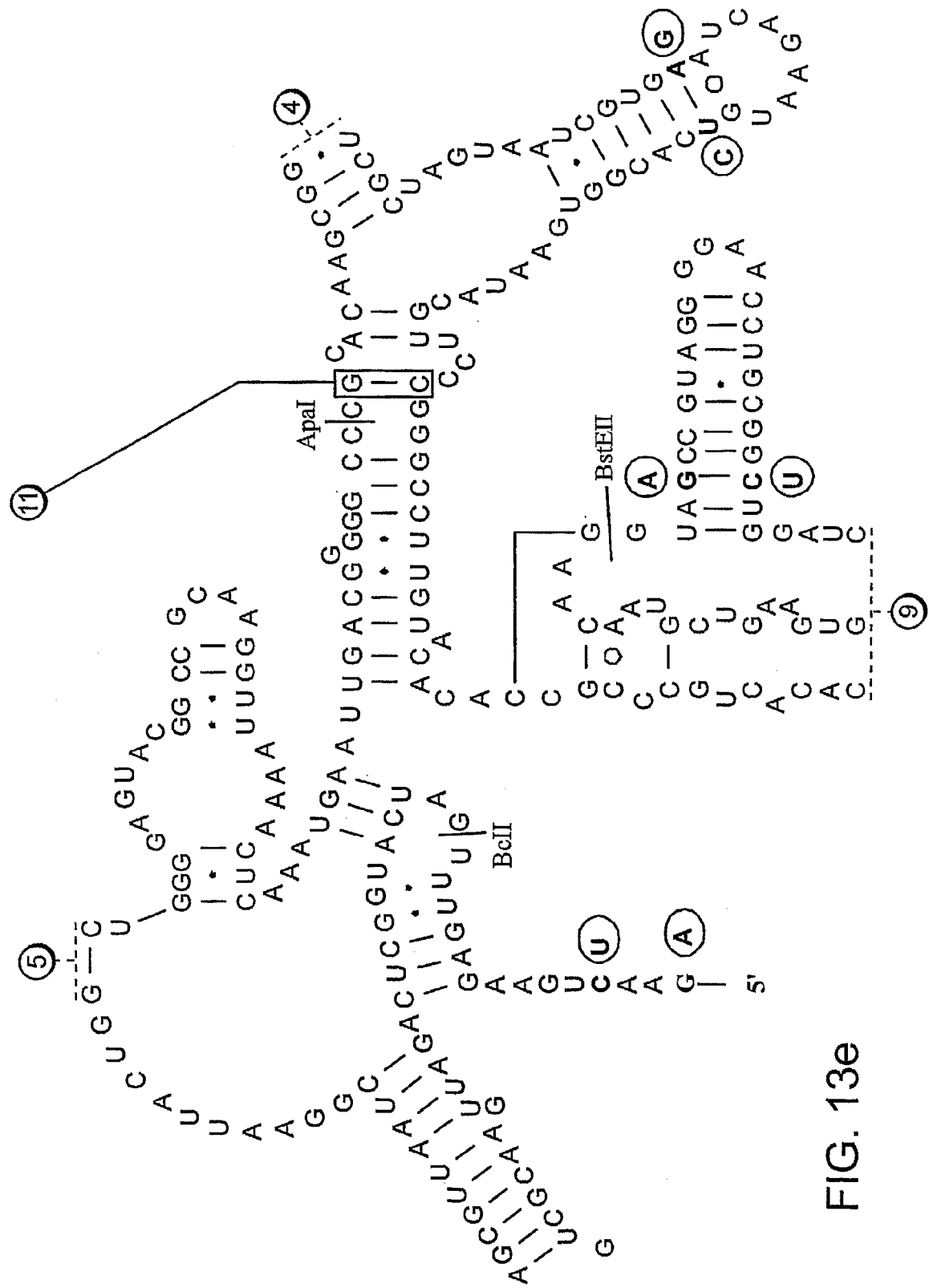
Figure 13F:
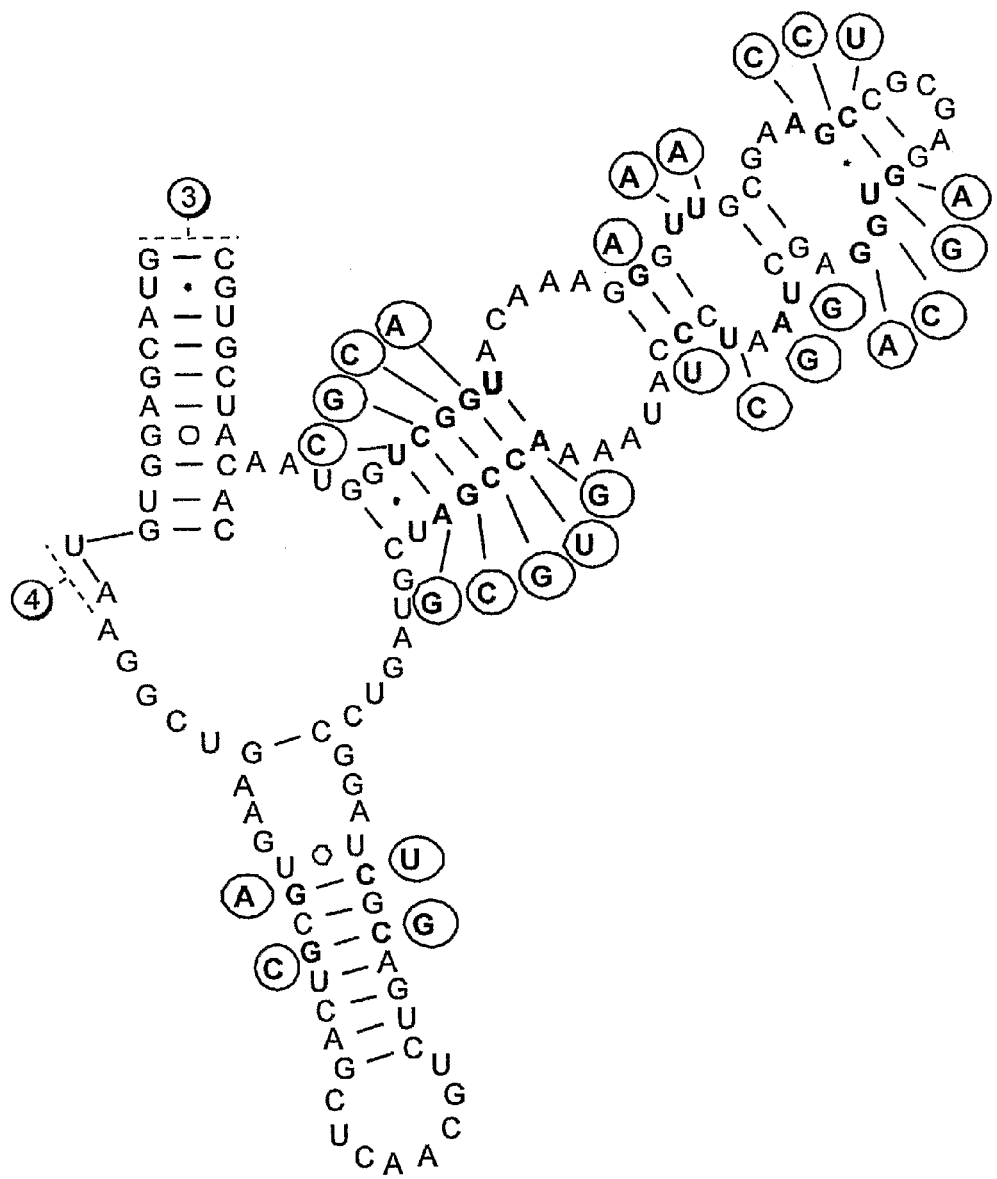
Figure 13G:
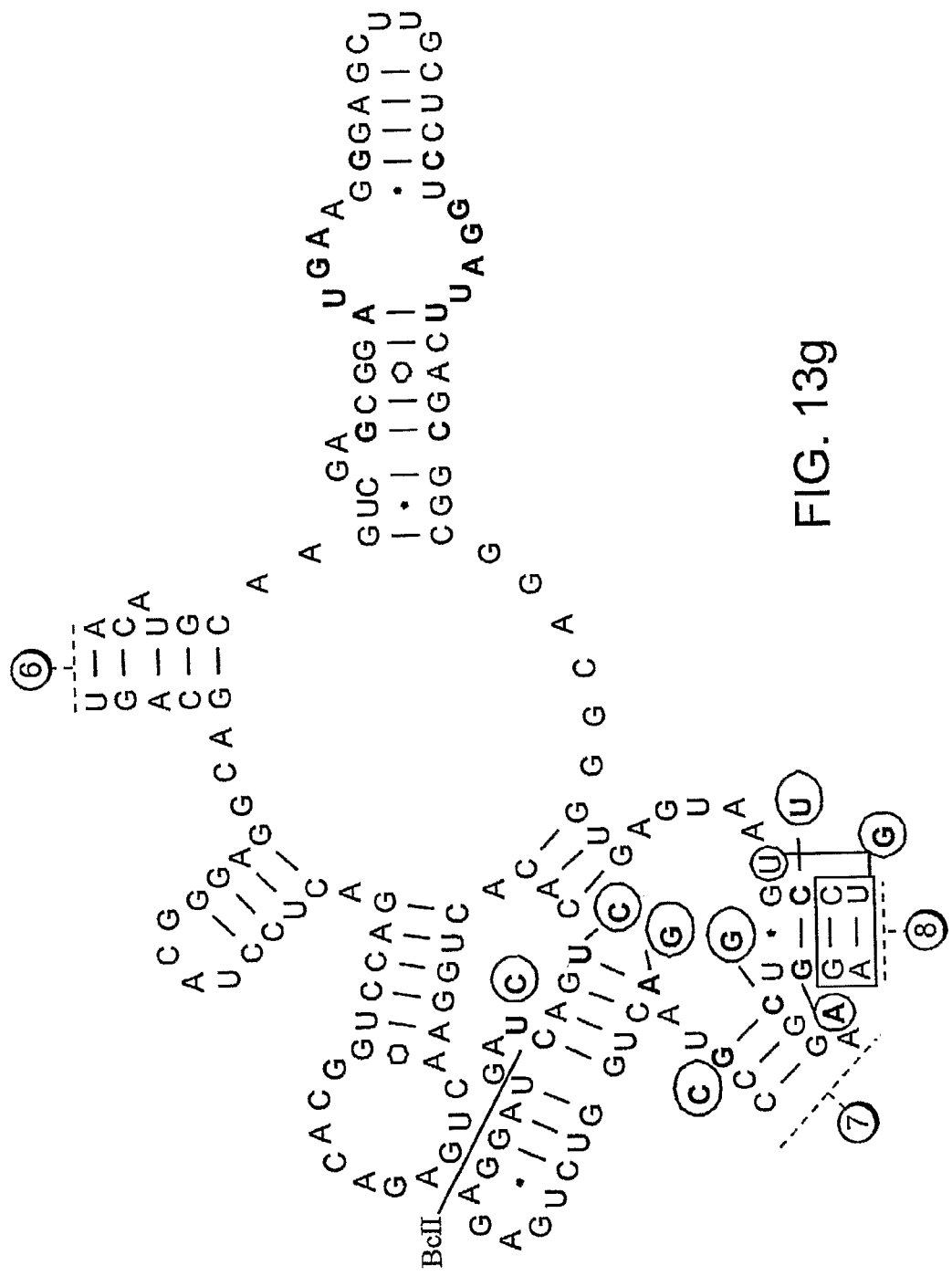
Figure 13H:
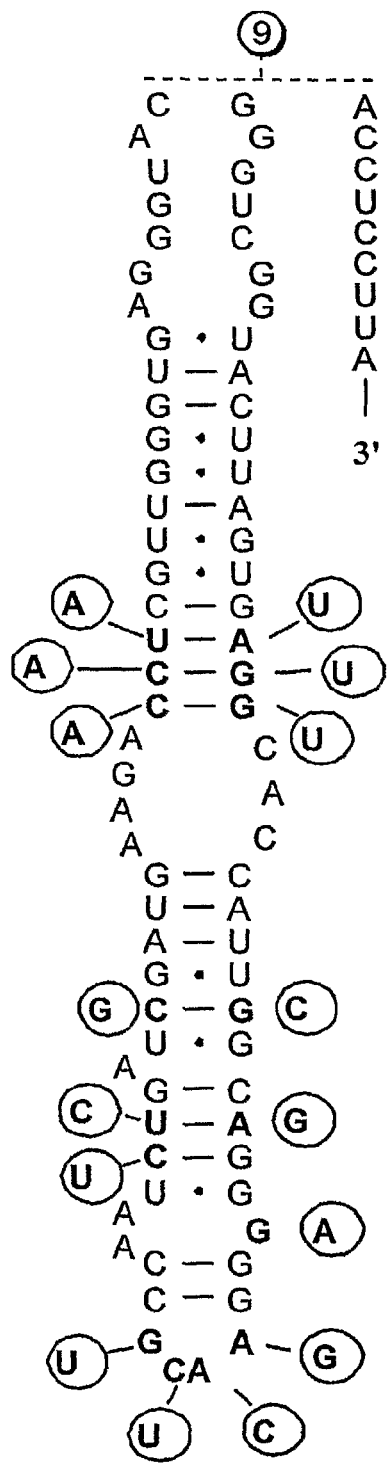
Figure 13I:
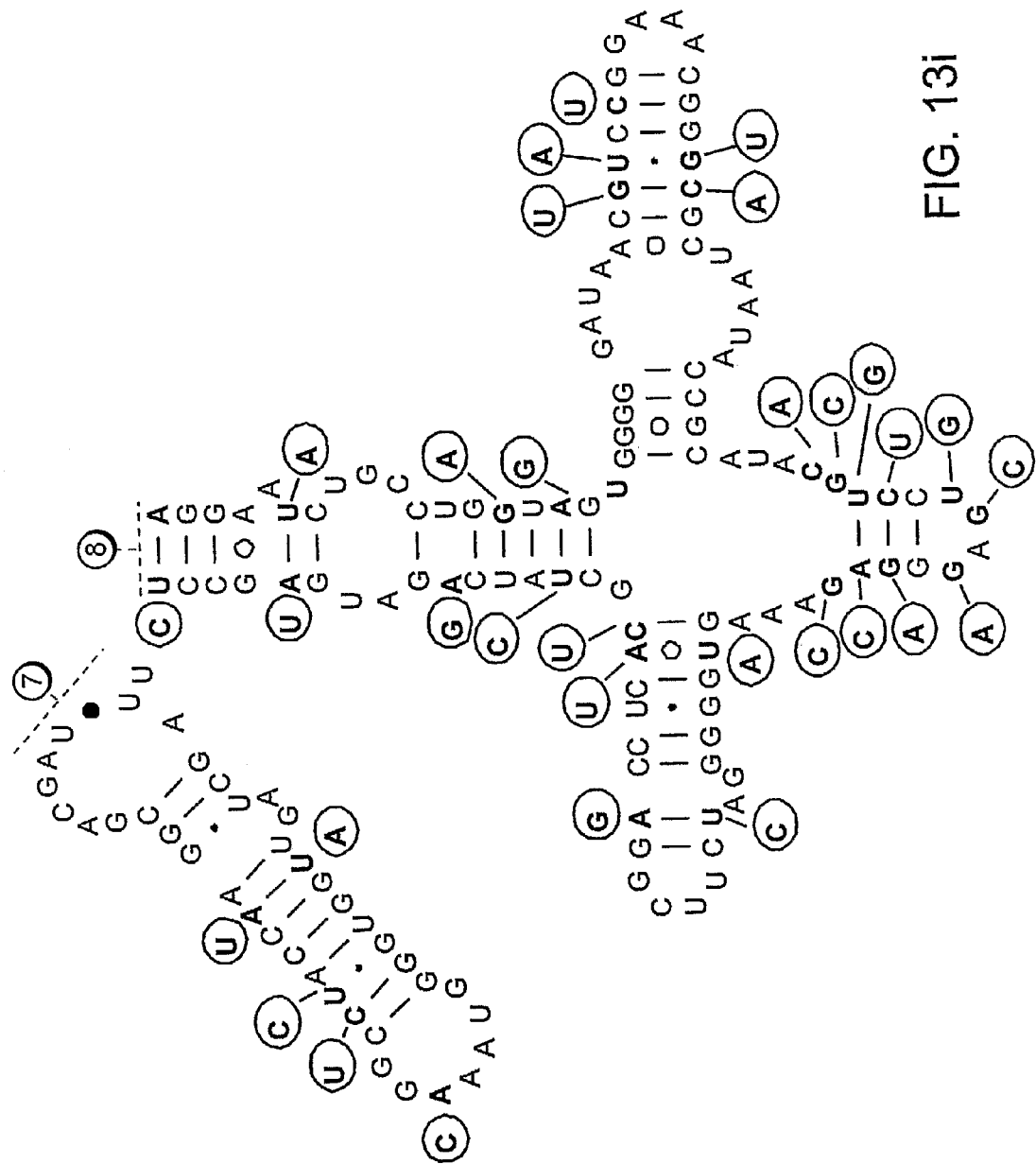
Figure 15:
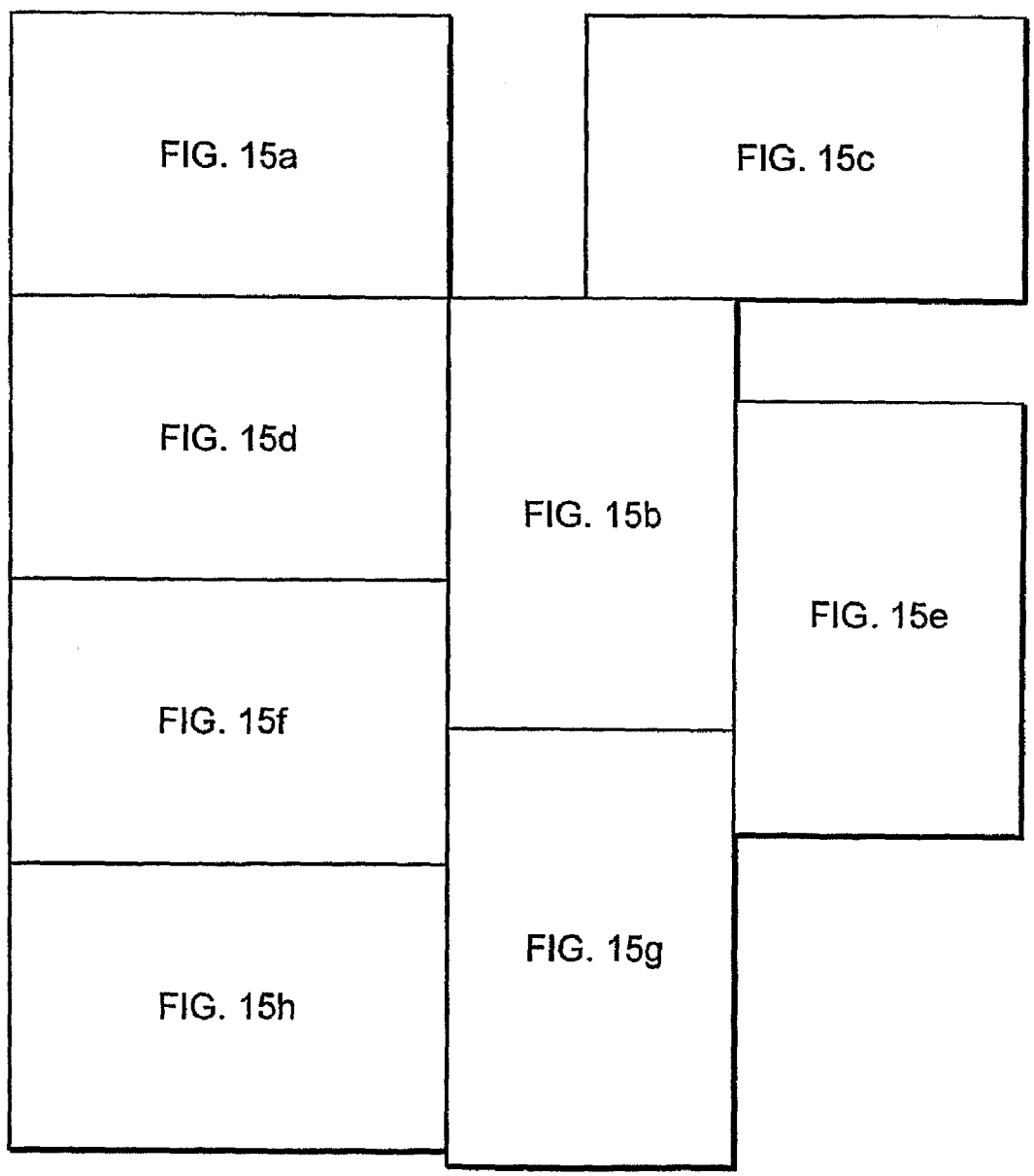
FIG. 15 depicts a mutant *P. aeruginosa* 16S rRNA wherein the helix 9 (H9) nucleotides, 176-188 (boxed in the lower left), have been replaced with the corresponding *E. coli* H9 nucleotides (SEQ ID NO: 151).
Figure 15A:
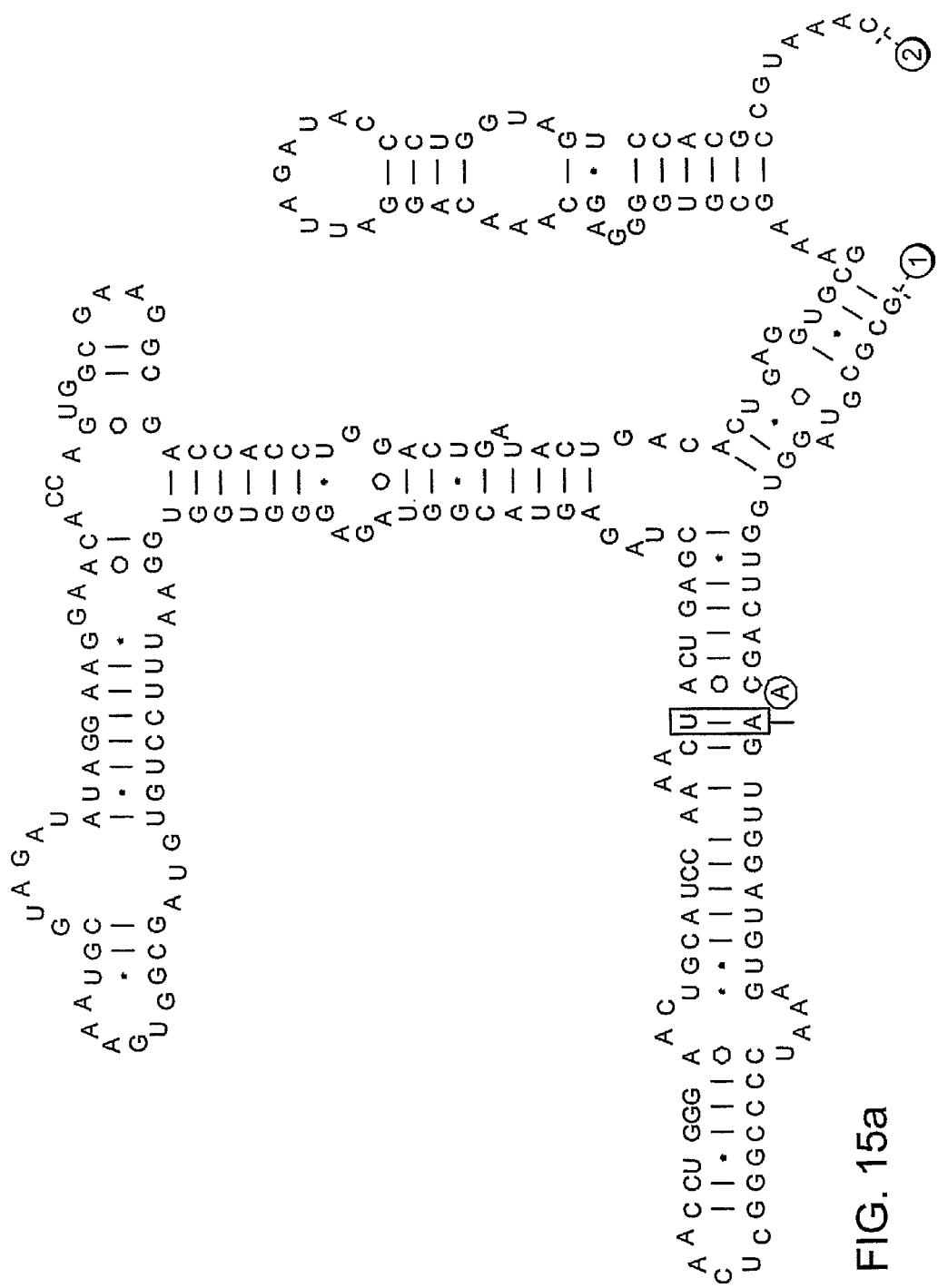
Figure 15B:
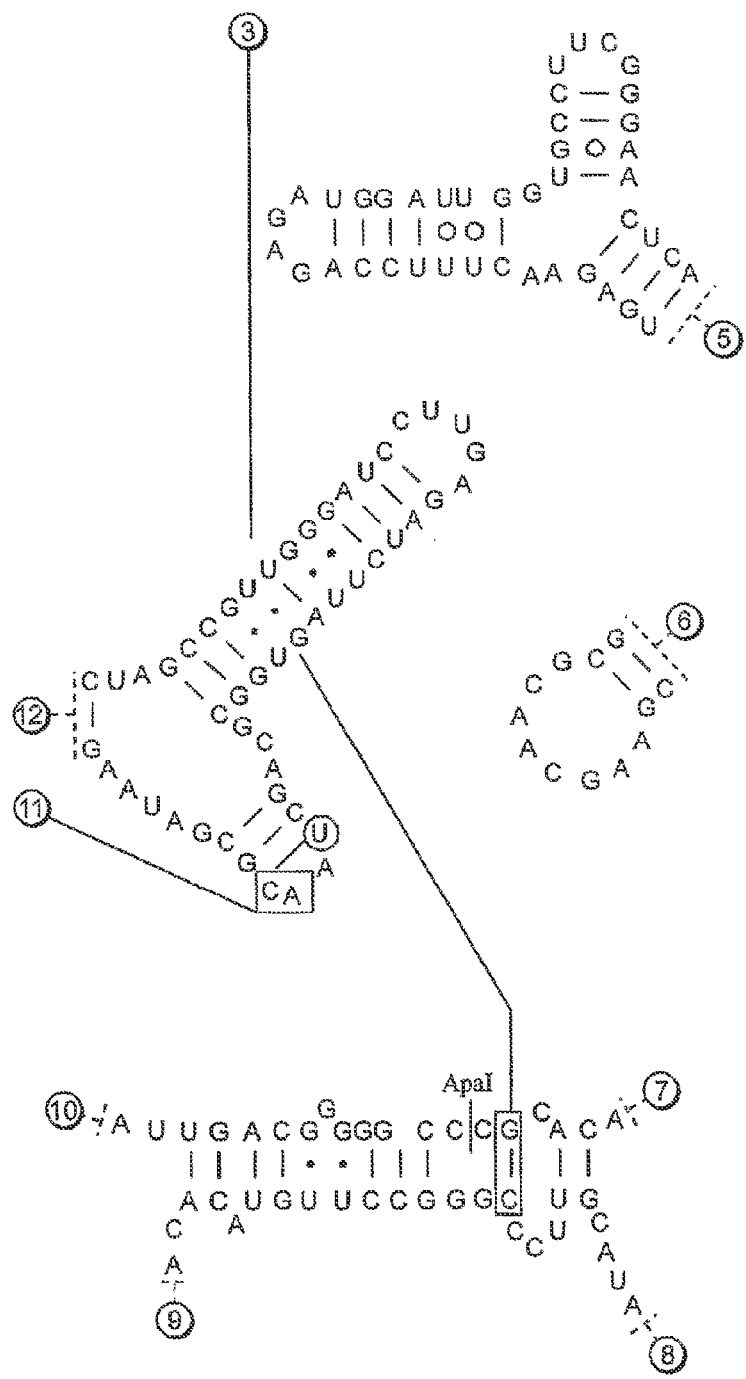
Figure 15C:
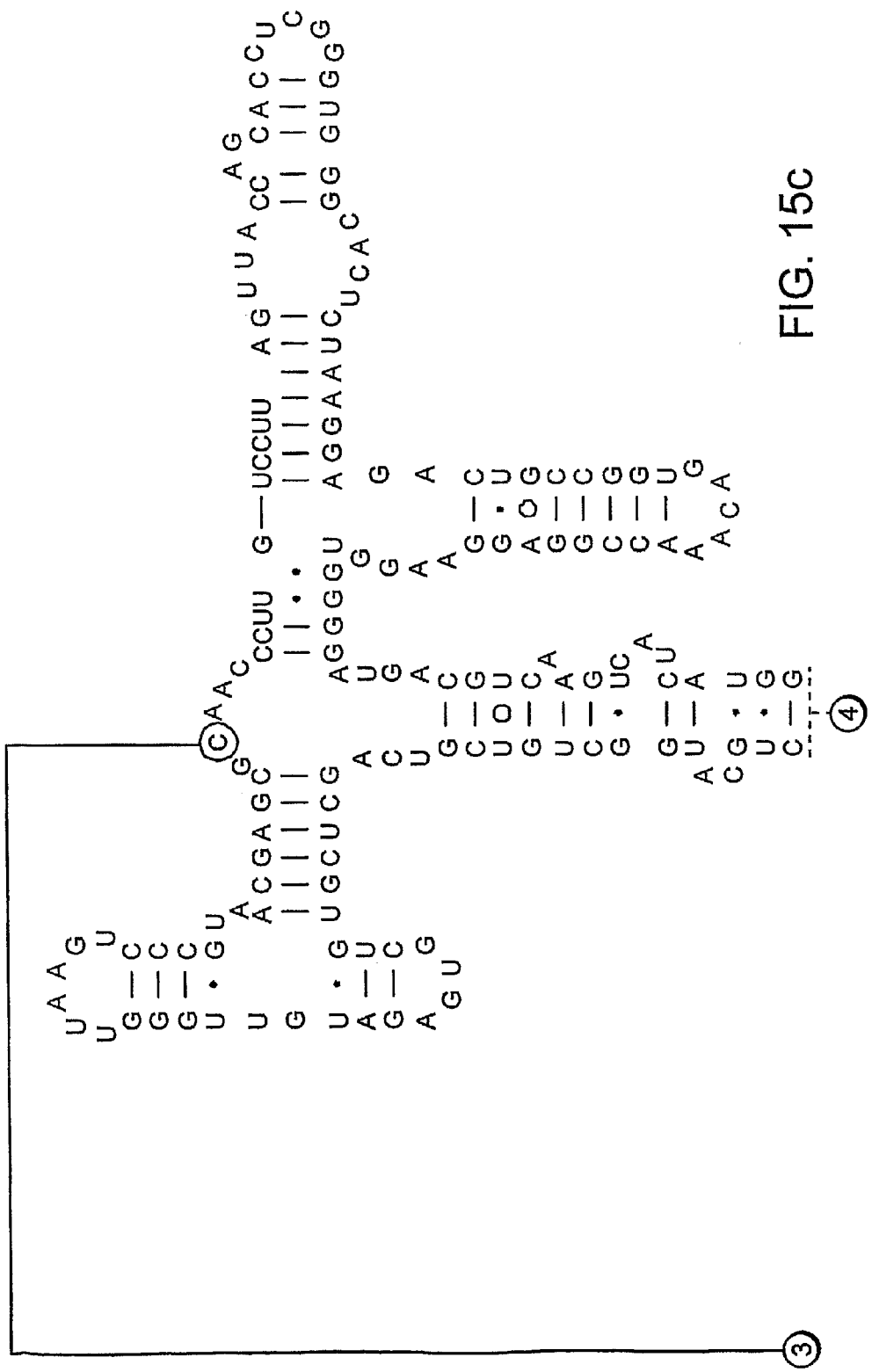
Figure 15D:
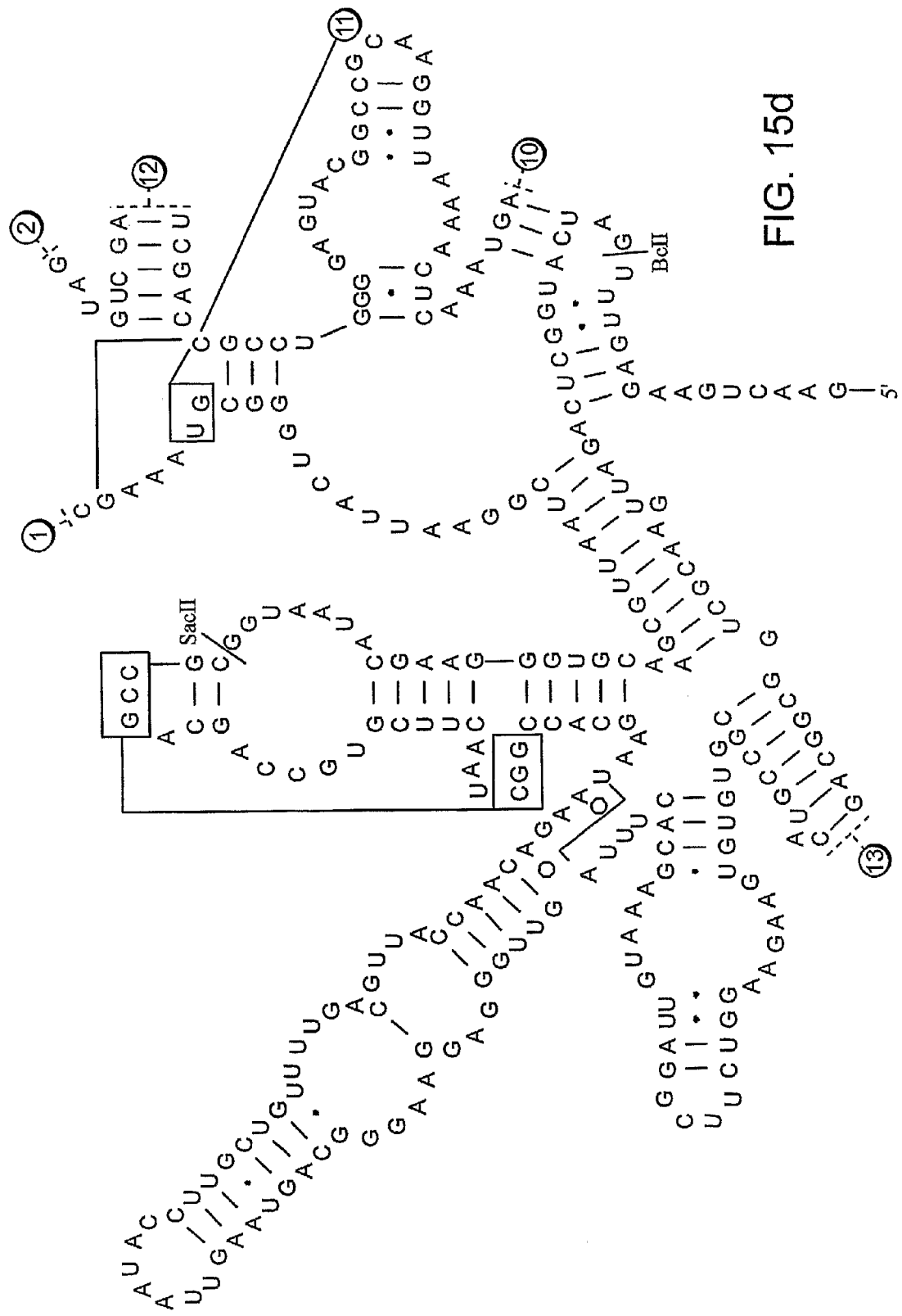
Figure 15E:
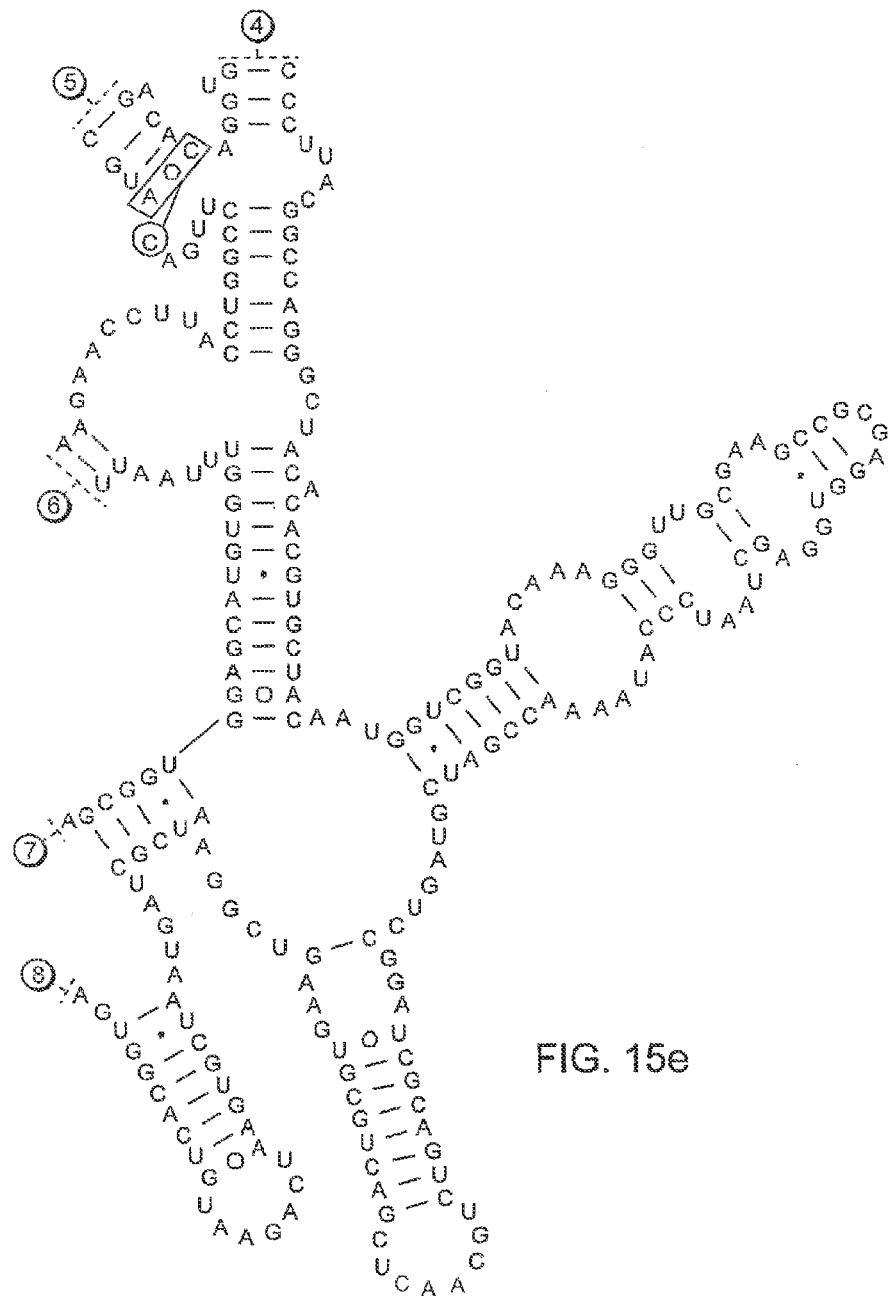
Figure 15F:
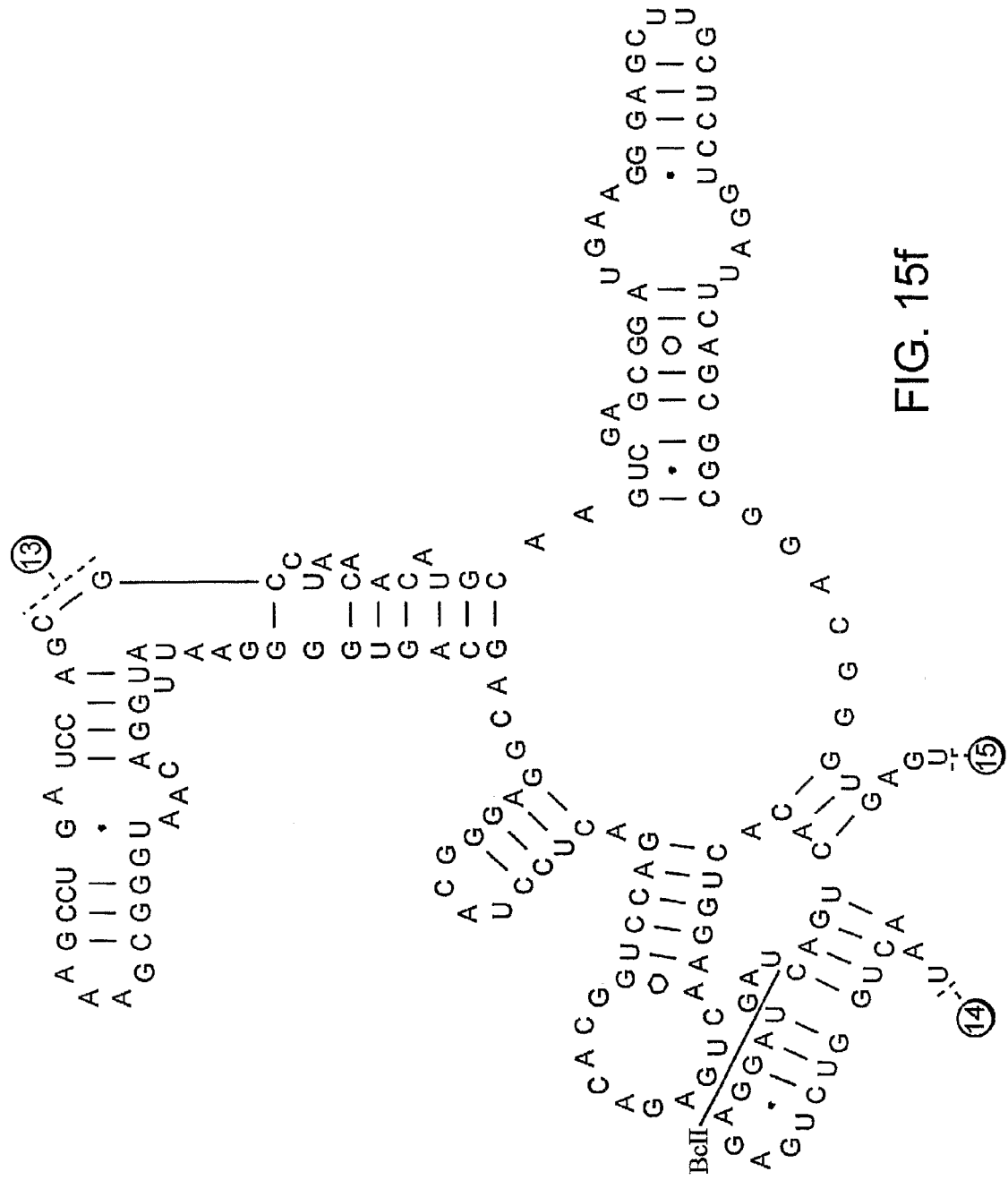
Figure 15G:
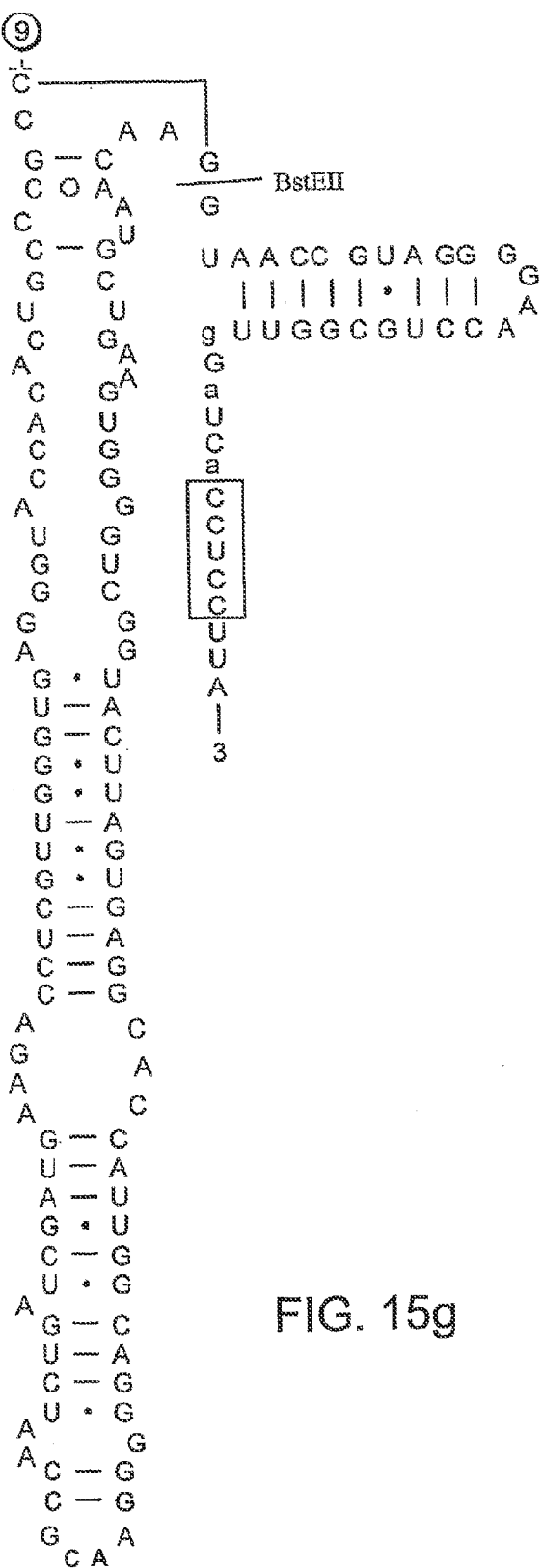
Figure 15H:
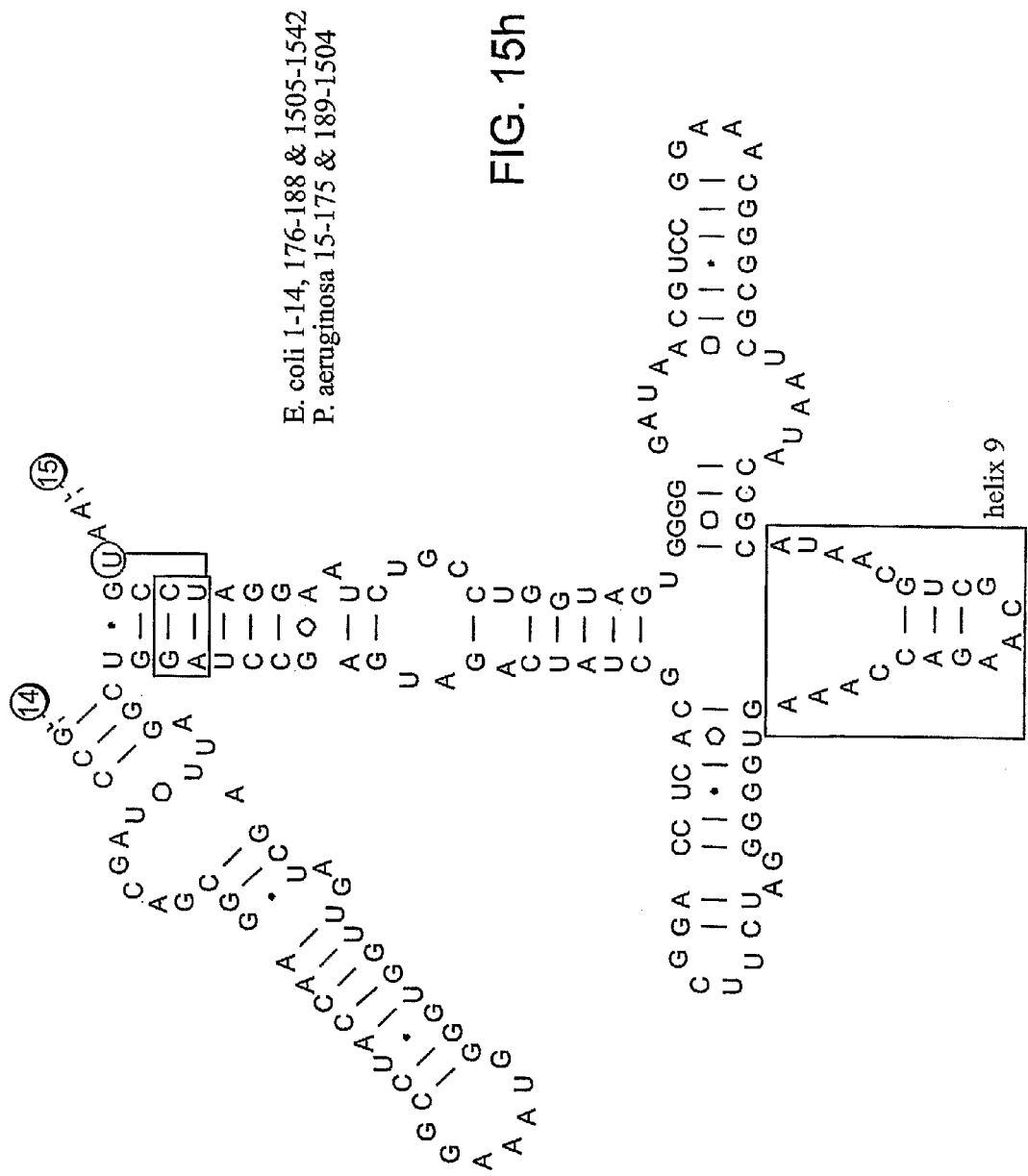

Another aspect of the invention relates to a plasmid of FIG. 3 or 4.

In certain embodiments the present invention relates to the aforementioned plasmid, further comprising aph (3')-la (kanamycin resistance) gene.

In certain embodiments the present invention relates to the aforementioned plasmid, further comprising the terminator T1 and terminator T2 of the *Escherichia coli* rrnA, rrnB, rrnC, rrnD, rrnE, rrnG or rrnH operon; or a T1 terminator from one and a T2 terminator from another.

In certain embodiments the present invention relates to the aforementioned plasmid, comprising an operon from a bacteria.

In certain embodiments the present invention relates to the aforementioned plasmid, further comprising the terminator T1 and terminator T2 of the *Escherichia coli* rrnB operon.

In certain embodiments the present invention relates to the aforementioned plasmid, further comprising the terminator T1 and terminator T2 of the *Escherichia coli* rrnC operon.

In certain embodiments the present invention relates to the aforementioned plasmid, further comprising the terminator T1 and terminator T2 of an *Escherichia coli* rrn operon.

In certain embodiments the present invention relates to the aforementioned plasmid, further comprising the pBAD promoter and the AraC activator.

In certain embodiments the present invention relates to the aforementioned plasmid, further comprising the Shine-Dalgarno sequence GAGGA.

In certain embodiments the present invention relates to the aforementioned plasmid, wherein the DNA sequence encoding the rRNA gene is under the control of an inducible promoter.

Another aspect of the invention relates to a cell comprising an aforementioned plasmid. In certain embodiments said cell comprises a plasmid which comprises a first nucleic acid sequence and a second nucleic acid sequence; wherein said first nucleic acid sequence encodes a *Pseudomonas aeruginosa* 16S rRNA comprising a mutant Anti-Shine-Dalgarno sequence and at least one additional mutation outside the Anti-Shine-Dalgarno region; and said second sequence encodes a selectable marker having a mutant Shine-Dalgarno sequence; wherein said mutant Anti-Shine-Dalgarno specifically hybridizes to said mutant Shine-Dalgarno sequence. In certain embodiments said cell comprises a plasmid which comprises a first nucleic acid sequence and a second nucleic acid sequence; wherein said first nucleic acid sequence encodes a *Pseudomonas aeruginosa* 16S rRNA comprising a mutant Anti-Shine-Dalgarno sequence and at least one additional mutation outside the Anti-Shine-Dalgarno region; and said second sequence encodes a selectable marker having a mutant Shine-Dalgarno sequence; wherein said mutant Anti-Shine-Dalgarno specifically hybridizes to said mutant Shine-Dalgarno sequence.

Another aspect of the invention relates to a cell comprising two of the aforementioned plasmids. In certain embodiments said cell comprises a plasmid which comprises a first nucleic acid sequence and a second nucleic acid sequence; wherein said first nucleic acid sequence encodes a *Pseudomonas aeruginosa* 16S rRNA comprising a mutant Anti-Shine-Dalgarno sequence and at least one additional mutation outside the Anti-Shine-Dalgarno region; and said second sequence encodes a selectable marker having a mutant Shine-Dalgarno sequence; wherein said mutant Anti-Shine-Dalgarno specifically hybridizes to said mutant Shine-Dalgarno sequence; and a plasmid which comprises a *Pseudomonas aeruginosa* S20 gene.

In certain embodiments the present invention relates to the aforementioned cell, wherein the mutations in the rRNA gene affect the quantity of selectable marker produced.

In certain embodiments the present invention relates to the aforementioned cell, wherein the cell is a bacterial cell.

In certain embodiments the present invention relates to the aforementioned cell, wherein the cell is an *E. coli* cell.

Another aspect of the present invention is a method for identifying functional mutant ribosomes comprising:
(a) transforming a set of host cells with a set of plasmids, each plasmid comprising a mutant *Pseudomonas aeruginosa* 16S rRNA gene and a selectable marker gene;
wherein said mutant *Pseudomonas aeruginosa* 16S rRNA gene comprises at least one mutation and a first mutant Anti-Shine-Dalgarno sequence; and said first selectable marker gene comprises a first mutant Shine-Dalgarno sequence; and
wherein said first mutant Anti-Shine-Dalgarno sequence and said first mutant Shine-Dalgarno sequence are a mutually compatible pair;
thereby forming a set of transformed host cells;
(b) transforming said set of host cells with a plasmid comprising a *Pseudomonas aeruginosa* S20 gene;
(c) isolating from the set of transformed host cells those host cells which express the selectable marker gene product; and
(d) sequencing the mutant *Pseudomonas aeruginosa* 16S rRNA gene from each host cell isolated in step (c), thereby identifying functional mutant ribosomes.

Another aspect of the present invention is a method for identifying functional mutant ribosomes comprising:
(a) transforming a set of host cells with a set of plasmids, each plasmid comprising a mutant *Pseudomonas aeruginosa* 16S rRNA gene and a green fluorescent protein gene;
wherein said mutant *Pseudomonas aeruginosa* 16S rRNA gene comprises at least one mutation and a first mutant Anti-Shine-Dalgarno sequence; and said green fluorescent protein gene comprises a first mutant Shine-Dalgarno sequence; and
wherein said first mutant Anti-Shine-Dalgarno sequence and said first mutant Shine-Dalgarno sequence are a mutually compatible pair;
thereby forming a set of transformed host cells;
(b) transforming said set of host cells with a plasmid comprising a *Pseudomonas aeruginosa* S20 gene;
(c) isolating from the set of transformed host cells those host cells which express the green fluorescent protein gene product; and
(d) sequencing the mutant *Pseudomonas aeruginosa* 16S rRNA gene from each host cell isolated in step (c), thereby identifying functional mutant ribosomes.

Another aspect of the present invention is a method for identifying functional mutant ribosomes that may be suitable as drug targets comprising:
(a) transforming a first set of host cells with a first set of plasmids, each plasmid comprising a mutant *Pseudomonas aeruginosa* 16S rRNA gene and a selectable marker gene;
wherein said mutant *Pseudomonas aeruginosa* 16S rRNA gene comprises at least one mutation and a first mutant Anti-Shine-Dalgarno sequence; and said first selectable marker gene comprises a first mutant Shine-Dalgarno sequence; and
wherein said first mutant Anti-Shine-Dalgarno sequence and said first mutant Shine-Dalgarno sequence are a mutually compatible pair;
thereby forming a first set of transformed host cells;
(b) transforming said first set of host cells with a plasmid comprising a *Pseudomonas aeruginosa* S20 gene;
(c) isolating from the first set of transformed host cells those host cells which express the selectable marker gene product;
(d) sequencing the mutant *Pseudomonas aeruginosa* 16S rRNA gene from each host cell isolated in step (c) to identify regions of interest, wherein the regions of interest comprise sequences of one or more nucleic acids which are conserved in each first mutant *Pseudomonas aeruginosa* 16S rRNA gene sequenced;
(e) generating a second set of mutant *Pseudomonas aeruginosa* 16S rRNA genes wherein the regions of interest from step (d) are mutated; and each rRNA gene further comprises a second mutant Anti-Shine-Dalgarno sequence;
(f) inserting the second set of mutant *Pseudomonas aeruginosa* 16S rRNA genes comprising the mutated regions of interest from step (e) into a second set of plasmids; wherein said plasmids further comprise a second genetically engineered gene which encodes a second selectable marker having a second mutant Shine-Dalgarno sequence, wherein the second mutant Anti-Shine-Dalgarno and the second mutant Shine-Dalgarno sequence are a mutually compatible pair;
(g) transforming a second set of host cells with the plasmids from step (f) and plasmids comprising a *Pseudomonas aeruginosa* S20 gene, thereby forming a second set of transformed host cells;
(h) isolating from the second set of transformed host cells from step (g) those host cells which express the selectable marker gene product; and
(i) sequencing the *Pseudomonas aeruginosa* 16S rRNA gene from each host cell isolated in step (h), thereby identifying functional mutant ribosomes that may be suitable as drug targets.

Another aspect of the present invention is a method for identifying functional mutant ribosomes that may be suitable as drug targets comprising:
(a) transforming a first set of host cells with a first set of plasmids, each plasmid comprising a mutant *Pseudomonas aeruginosa* 16S rRNA gene and a first green fluorescent protein gene;
wherein said mutant *Pseudomonas aeruginosa* 16S rRNA gene comprises at least one mutation and a first mutant Anti-Shine-Dalgarno sequence; and said first green fluorescent protein gene comprises a first mutant Shine-Dalgarno sequence; and
wherein said first mutant Anti-Shine-Dalgarno sequence and said first mutant Shine-Dalgarno sequence are a mutually compatible pair;
thereby forming a first set of transformed host cells;
(b) transforming said first set of host cells with a plasmid comprising a *Pseudomonas aeruginosa* S20 gene;
(c) isolating from the first set of transformed host cells those host cells which express the green fluorescent protein gene product;
(d) sequencing the mutant *Pseudomonas aeruginosa* 16S rRNA gene from each host cell isolated in step (c) to identify regions of interest, wherein the regions of interest comprise sequences of one or more nucleic acids which are conserved in each first mutant *Pseudomonas aeruginosa* 16S rRNA gene sequenced;
(e) generating a second set of mutant *Pseudomonas aeruginosa* 16S rRNA genes wherein the regions of interest from step (d) are mutated; and each rRNA gene further comprises a second mutant Anti-Shine-Dalgarno sequence;

(f) inserting the second set of mutant *Pseudomonas aeruginosa* 16S rRNA genes comprising the mutated regions of interest from step (e) into a second set of plasmids; wherein said plasmids further comprise a second genetically engineered gene which encodes a second green fluorescent protein having a second mutant Shine-Dalgarno sequence, wherein the second mutant Anti-Shine-Dalgarno and the second mutant Shine-Dalgarno sequence are a mutually compatible pair;

(g) transforming a second set of host cells with the plasmids from step (f) and plasmids comprising a *Pseudomonas aeruginosa* S20 gene, thereby forming a second set of transformed host cells;

(h) isolating from the second set of transformed host cells from step (g) those host cells which express the green fluorescent protein gene product; and (i) sequencing the *Pseudomonas aeruginosa* 16S rRNA gene from each host cell isolated in step (h), thereby identifying functional mutant ribosomes that may be suitable as drug targets.

Another aspect of the present invention is a method for identifying drug candidates comprising:
(a) transforming a first set of host cells with a first set of plasmids, each plasmid comprising a mutant *Pseudomonas aeruginosa* 16S rRNA gene and a selectable marker gene;
wherein said mutant *Pseudomonas aeruginosa* 16S rRNA gene comprises at least one mutation and a first mutant Anti-Shine-Dalgarno sequence; and said first selectable marker gene comprises a first mutant Shine-Dalgarno sequence; and
wherein said first mutant Anti-Shine-Dalgarno sequence and said first mutant Shine-Dalgarno sequence are a mutually compatible pair;
thereby forming a first set of transformed host cells;
(b) transforming said first set of host cells with a plasmid comprising a *Pseudomonas aeruginosa* S20 gene;
(c) isolating from the first set of transformed host cells those host cells which express the selectable marker gene product;
(d) sequencing the mutant *Pseudomonas aeruginosa* 16S rRNA gene from each host cell isolated in step (c) to identify regions of interest, wherein the regions of interest comprise sequences of one or more nucleic acids which are conserved in each first mutant *Pseudomonas aeruginosa* 16S rRNA gene sequenced;
(e) generating a second set of mutant *Pseudomonas aeruginosa* 16S rRNA genes wherein the regions of interest from step (d) are mutated; and each rRNA gene further comprises a second mutant Anti-Shine-Dalgarno sequence;
(f) inserting the second set of mutant *Pseudomonas aeruginosa* 16S rRNA genes comprising the mutated regions of interest from step (e) into a second set of plasmids; wherein said plasmids further comprise a second genetically engineered gene which encodes a second selectable marker having a second mutant Shine-Dalgarno sequence, wherein the second mutant Anti-Shine-Dalgarno and the second mutant Shine-Dalgarno sequence are a mutually compatible pair;
(g) transforming a second set of host cells with the plasmids from step (f) and plasmids comprising a *Pseudomonas aeruginosa* S20 gene, thereby forming a second set of transformed host cells;
(h) isolating from the second set of transformed host cells from step (g) those host cells which express the selectable marker gene product;
(i) sequencing the *Pseudomonas aeruginosa* 16S rRNA gene from each host cell isolated in step (h), to identify the mutated regions of interest;
(j) screening compounds against the mutated regions of interest from step (i) and wildtype *Pseudomonas aeruginosa* 16S rRNA;
(k) identifying the compounds from step (j) that bind to the mutated regions of interest from step (h) and the wildtype *Pseudomonas aeruginosa* 16S rRNA;
(l) screening the compounds from step (k) against human 16S rRNA; and
(m) identifying the drug candidates from step (l) that do not bind to the human 16S rRNA, thereby identifying drug candidates.

Another aspect of the present invention is a method for identifying drug candidates comprising:
(a) transforming a first set of host cells with a first set of plasmids, each plasmid comprising a mutant *Pseudomonas aeruginosa* 16S rRNA gene and a first green fluorescent protein gene;
wherein said mutant *Pseudomonas aeruginosa* 16S rRNA gene comprises at least one mutation and a first mutant Anti-Shine-Dalgarno sequence; and said first green fluorescent protein gene comprises a first mutant Shine-Dalgarno sequence; and
wherein said first mutant Anti-Shine-Dalgarno sequence and said first mutant Shine-Dalgarno sequence are a mutually compatible pair;
thereby forming a first set of transformed host cells;
(b) transforming said first set of host cells with a plasmid comprising a *Pseudomonas aeruginosa* S20 gene;
(c) isolating from the first set of transformed host cells those host cells which express the green fluorescent protein gene product;
(d) sequencing the mutant *Pseudomonas aeruginosa* 16S rRNA gene from each host cell isolated in step (c) to identify regions of interest, wherein the regions of interest comprise sequences of one or more nucleic acids which are conserved in each first mutant *Pseudomonas aeruginosa* 16S rRNA gene sequenced;
(e) generating a second set of mutant *Pseudomonas aeruginosa* 16S rRNA genes wherein the regions of interest from step (d) are mutated; and each rRNA gene further comprises a second mutant Anti-Shine-Dalgarno sequence;
(f) inserting the second set of mutant *Pseudomonas aeruginosa* 16S rRNA genes comprising the mutated regions of interest from step (e) into a second set of plasmids; wherein said plasmids further comprise a second genetically engineered gene which encodes a second green fluorescent protein having a second mutant Shine-Dalgarno sequence, wherein the second mutant Anti-Shine-Dalgarno and the second mutant Shine-Dalgarno sequence are a mutually compatible pair;
(g) transforming a second set of host cells with the plasmids from step (f) and plasmids comprising a *Pseudomonas aeruginosa* S20 gene, thereby forming a second set of transformed host cells;
(h) isolating from the second set of transformed host cells from step (g) those host cells which express the green fluorescent protein gene product;
(i) sequencing the *Pseudomonas aeruginosa* 16S rRNA gene from each host cell isolated in step (h), to identify the mutated regions of interest;
(j) screening compounds against the mutated regions of interest from step (i) and wildtype *Pseudomonas aeruginosa* 16S rRNA;

(k) identifying the compounds from step (j) that bind to the mutated regions of interest from step (h) and the wild-type *Pseudomonas aeruginosa* 16S rRNA;

(l) screening the compounds from step (k) against human 16S rRNA; and (m) identifying the drug candidates from step (l) that do not bind to the human 16S rRNA, thereby identifying drug candidates.

Another aspect of the present invention is a method for identifying functional mutant ribosomes comprising:

(a) transforming a set of host cells with a set of plasmids, each plasmid comprising a mutant *Pseudomonas aeruginosa* 16S rRNA gene and a selectable marker gene;

wherein said mutant *Pseudomonas aeruginosa* 16S rRNA gene comprises at least one mutation, a mutant helix 9 sequence, and a first mutant Anti-Shine-Dalgarno sequence; and said first selectable marker gene comprises a first mutant Shine-Dalgarno sequence; and wherein said first mutant Anti-Shine-Dalgarno sequence and said first mutant Shine-Dalgarno sequence are a mutually compatible pair;

thereby forming a set of transformed host cells;

(b) isolating from the set of transformed host cells those host cells which express the selectable marker gene product; and (c) sequencing the mutant *Pseudomonas aeruginosa* 16S rRNA gene from each host cell isolated in step (b), thereby identifying functional mutant ribosomes.

Another aspect of the present invention is a method for identifying functional mutant ribosomes comprising:

(a) transforming a set of host cells with a set of plasmids, each plasmid comprising a mutant *Pseudomonas aeruginosa* 16S rRNA gene and a green fluorescent protein gene;

wherein said mutant *Pseudomonas aeruginosa* 16S rRNA gene comprises at least one mutation, a mutant helix 9 sequence, and a first mutant Anti-Shine-Dalgarno sequence; and said green fluorescent protein gene comprises a first mutant Shine-Dalgarno sequence; and wherein said first mutant Anti-Shine-Dalgarno sequence and said first mutant Shine-Dalgarno sequence are a mutually compatible pair;

thereby forming a set of transformed host cells;

(b) isolating from the set of transformed host cells those host cells which express the green fluorescent protein gene product; and (c) sequencing the mutant *Pseudomonas aeruginosa* 16S rRNA gene from each host cell isolated in step (b), thereby identifying functional mutant ribosomes.

Another aspect of the present invention is a method for identifying functional mutant ribosomes that may be suitable as drug targets comprising:

(a) transforming a first set of host cells with a first set of plasmids, each plasmid comprising a mutant *Pseudomonas aeruginosa* 16S rRNA gene and a selectable marker gene;

wherein said mutant *Pseudomonas aeruginosa* 16S rRNA gene comprises at least one mutation, a mutant helix 9 sequence, and a first mutant Anti-Shine-Dalgarno sequence; and said first selectable marker gene comprises a first mutant Shine-Dalgarno sequence; and wherein said first mutant Anti-Shine-Dalgarno sequence and said first mutant Shine-Dalgarno sequence are a mutually compatible pair;

thereby forming a first set of transformed host cells;

(b) isolating from the first set of transformed host cells those host cells which express the selectable marker gene product;

(c) sequencing the mutant *Pseudomonas aeruginosa* 16S rRNA gene from each host cell isolated in step (b) to identify regions of interest, wherein the regions of interest comprise sequences of one or more nucleic acids which are conserved in each first mutant *Pseudomonas aeruginosa* 16S rRNA gene sequenced;

(d) generating a second set of mutant *Pseudomonas aeruginosa* 16S rRNA genes wherein the regions of interest from step (c) are mutated; and each mutant *Pseudomonas aeruginosa* 16S rRNA gene further comprises a mutant helix 9 sequence, and a second mutant Anti-Shine-Dalgarno sequence;

(e) inserting the second set of mutant *Pseudomonas aeruginosa* 16S rRNA genes comprising the mutated regions of interest from step (d) into a second set of plasmids; wherein said plasmids further comprise a second genetically engineered gene which encodes a second selectable marker having a second mutant Shine-Dalgarno sequence, wherein the second mutant Anti-Shine-Dalgarno and the second mutant Shine-Dalgarno sequence are a mutually compatible pair;

(f) transforming a second set of host cells with the plasmids from step (e), thereby forming a second set of transformed host cells;

(g) isolating from the second set of transformed host cells from step (f) those host cells which express the selectable marker gene product; and (h) sequencing the *Pseudomonas aeruginosa* 16S rRNA gene from each host cell isolated in step (g), thereby identifying functional mutant ribosomes that may be suitable as drug targets.

Another aspect of the present invention is a method for identifying functional mutant ribosomes that may be suitable as drug targets comprising:

(a) transforming a first set of host cells with a first set of plasmids, each plasmid comprising a mutant *Pseudomonas aeruginosa* 16S rRNA gene and a first green fluorescent protein gene;

wherein said mutant *Pseudomonas aeruginosa* 16S rRNA gene comprises at least one mutation, a mutant helix 9 sequence, and a first mutant Anti-Shine-Dalgarno sequence; and said first green fluorescent protein gene comprises a first mutant Shine-Dalgarno sequence; and wherein said first mutant Anti-Shine-Dalgarno sequence and said first mutant Shine-Dalgarno sequence are a mutually compatible pair;

thereby forming a first set of transformed host cells;

(b) isolating from the first set of transformed host cells those host cells which express the green fluorescent protein gene product;

(c) sequencing the mutant *Pseudomonas aeruginosa* 16S rRNA gene from each host cell isolated in step (b) to identify regions of interest, wherein the regions of interest comprise sequences of one or more nucleic acids which are conserved in each first mutant *Pseudomonas aeruginosa* 16S rRNA gene sequenced;

(d) generating a second set of mutant *Pseudomonas aeruginosa* 16S rRNA genes wherein the regions of interest from step (d) are mutated; and each mutant

*Pseudomonas aeruginosa* 16S rRNA gene further comprises a mutant helix 9 sequence, and a second mutant Anti-Shine-Dalgarno sequence;
(e) inserting the second set of mutant *Pseudomonas aeruginosa* 16S rRNA genes comprising the mutated regions of interest from step (d) into a second set of plasmids; wherein said plasmids further comprise a second genetically engineered gene which encodes a second green fluorescent protein having a second mutant Shine-Dalgarno sequence, wherein the second mutant Anti-Shine-Dalgarno and the second mutant Shine-Dalgarno sequence are a mutually compatible pair;
(f) transforming a second set of host cells with the plasmids from step (e), thereby forming a second set of transformed host cells;
(g) isolating from the second set of transformed host cells from step (f) those host cells which express the green fluorescent protein gene product; and
(h) sequencing the *Pseudomonas aeruginosa* 16S rRNA gene from each host cell isolated in step (g), thereby identifying functional mutant ribosomes that may be suitable as drug targets.

Another aspect of the present invention is a method for identifying drug candidates comprising:
(a) transforming a first set of host cells with a first set of plasmids, each plasmid comprising a mutant *Pseudomonas aeruginosa* 16S rRNA gene and a selectable marker gene;
wherein said mutant *Pseudomonas aeruginosa* 16S rRNA gene comprises at least one mutation, a mutant helix 9 sequence, and a first mutant Anti-Shine-Dalgarno sequence; and said first selectable marker gene comprises a first mutant Shine-Dalgarno sequence; and
wherein said first mutant Anti-Shine-Dalgarno sequence and said first mutant Shine-Dalgarno sequence are a mutually compatible pair;
thereby forming a first set of transformed host cells;
(b) isolating from the first set of transformed host cells those host cells which express the selectable marker gene product;
(c) sequencing the mutant *Pseudomonas aeruginosa* 16S rRNA gene from each host cell isolated in step (b) to identify regions of interest, wherein the regions of interest comprise sequences of one or more nucleic acids which are conserved in each first mutant *Pseudomonas aeruginosa* 16S rRNA gene sequenced;
(d) generating a second set of mutant *Pseudomonas aeruginosa* 16S rRNA genes wherein the regions of interest from step (c) are mutated; and each mutant *Pseudomonas aeruginosa* 16S rRNA gene further comprises a mutant helix 9 sequence, and a second mutant Anti-Shine-Dalgarno sequence;
(e) inserting the second set of mutant *Pseudomonas aeruginosa* 16S rRNA genes comprising the mutated regions of interest from step (d) into a second set of plasmids; wherein said plasmids further comprise a second genetically engineered gene which encodes a second selectable marker having a second mutant Shine-Dalgarno sequence, wherein the second mutant Anti-Shine-Dalgarno and the second mutant Shine-Dalgarno sequence are a mutually compatible pair;
(f) transforming a second set of host cells with the plasmids from step (e), thereby forming a second set of transformed host cells;
(g) isolating from the second set of transformed host cells from step (f) those host cells which express the selectable marker gene product;
(h) sequencing the *Pseudomonas aeruginosa* 16S rRNA gene from each host cell isolated in step (g), to identify the mutated regions of interest;
(i) screening compounds against the mutated regions of interest from step (h) and wildtype *Pseudomonas aeruginosa* 16S rRNA;
(j) identifying the compounds from step (i) that bind to the mutated regions of interest from step (h) and the wildtype *Pseudomonas aeruginosa* 16S rRNA;
(k) screening the compounds from step (j) against human 16S rRNA; and
(l) identifying the drug candidates from step (k) that do not bind to the human 16S rRNA, thereby identifying drug candidates.

Another aspect of the present invention is a method for identifying drug candidates comprising:
(a) transforming a first set of host cells with a first set of plasmids, each plasmid comprising a mutant *Pseudomonas aeruginosa* 16S rRNA gene and a first green fluorescent protein gene;
wherein said mutant *Pseudomonas aeruginosa* 16S rRNA gene comprises at least one mutation, a mutant helix 9 sequence, and a first mutant Anti-Shine-Dalgarno sequence; and said first green fluorescent protein gene comprises a first mutant Shine-Dalgarno sequence; and
wherein said first mutant Anti-Shine-Dalgarno sequence and said first mutant Shine-Dalgarno sequence are a mutually compatible pair;
thereby forming a first set of transformed host cells;
(b) isolating from the first set of transformed host cells those host cells which express the green fluorescent protein gene product;
(c) sequencing the mutant *Pseudomonas aeruginosa* 16S rRNA gene from each host cell isolated in step (b) to identify regions of interest, wherein the regions of interest comprise sequences of one or more nucleic acids which are conserved in each first mutant *Pseudomonas aeruginosa* 16S rRNA gene sequenced;
(d) generating a second set of mutant *Pseudomonas aeruginosa* 16S rRNA genes wherein the regions of interest from step (d) are mutated; and each mutant *Pseudomonas aeruginosa* 16S rRNA gene further comprises a mutant helix 9 sequence, and a second mutant Anti-Shine-Dalgarno sequence;
(e) inserting the second set of mutant *Pseudomonas aeruginosa* 16S rRNA genes comprising the mutated regions of interest from step (d) into a second set of plasmids; wherein said plasmids further comprise a second genetically engineered gene which encodes a second green fluorescent protein having a second mutant Shine-Dalgarno sequence, wherein the second mutant Anti-Shine-Dalgarno and the second mutant Shine-Dalgarno sequence are a mutually compatible pair;
(f) transforming a second set of host cells with the plasmids from step (e), thereby forming a second set of transformed host cells;
(g) isolating from the second set of transformed host cells from step (f) those host cells which express the green fluorescent protein gene product;
(h) sequencing the *Pseudomonas aeruginosa* 16S rRNA gene from each host cell isolated in step (g), to identify the mutated regions of interest;

(i) screening compounds against the mutated regions of interest from step (h) and wildtype *Pseudomonas aeruginosa* 16S rRNA;

(j) identifying the compounds from step (i) that bind to the mutated regions of interest from step (h) and the wildtype *Pseudomonas aeruginosa* 16S rRNA;

(k) screening the compounds from step (j) against human 16S rRNA; and (l) identifying the drug candidates from step (k) that do not bind to the human 16S rRNA, thereby identifying drug candidates.

This invention is further illustrated by the following examples, which should not be construed as limiting. The contents of all references, patents and published patent applications cited throughout this application, as well as the Figures and Appendices, are incorporated herein by reference.

EXEMPLIFICATION

Example 1

Identification of Mutant SD and Mutant ASD Combinations

It has been shown that by coordinately changing the SD and ASD, a particular mRNA containing an altered SD could be targeted to ribosomes containing the altered ASD. This and all other efforts to modify the ASD, however, have proved lethal, as cells containing these mutations died within two hours after the genes containing them were activated.

Using random mutagenesis and genetic selection, mutant SD-ASD combinations are screened in order to identify non-lethal SD-ASD combinations. The mutant SD-ASD mutually compatible pairs are set forth in FIGS. 10, 11 and 12. The mutually compatible pairs of mutant sequences interact as pairs in the form of RNA. The novel mutant SD-ASD sequence combinations of the present invention permit translation of only the mRNAs containing the altered SD sequence.

Example 2A

Construction of the Pa 16S pRNA228 Plasmid

A plasmid construct of the present invention identified as the Pa 16S pRNA228 plasmid, is set forth in FIGS. 1 and 6. *E. coli* cells contain a single chromosome with seven copies of the rRNA genes and all of the genes for the ribosomal proteins. The plasmid, Pa 16S pRNA228, in the cell contains a genetically engineered copy of one of the 16S rRNA genes from *P. aeruginosa* and two genetically engineered genes that are not normally found in *E. coli*, referred to herein as a "selectable markers." One gene encodes the protein chloramphenicol acetyltransferase (CAT). This protein renders cells resistant to chloramphenicol by chemically modifying the antibiotic. Another gene, the Green Fluorescent Protein (GFP), is also included in the system. GFP facilitates high-throughput functional analysis. The amount of green light produced upon irradiation with ultraviolet light is proportional to the amount of GFP present in the cell.

Ribosomes from Pa 16S pRNA228 have an altered ASD sequence. Therefore, the ribosomes can only translate mRNAs that have an altered SD sequence. Only two genes in the cell produce mRNAs with altered SD sequences that may be translated by the plasmid-encoded ribosomes: the CAT and GFP gene. Mutations in rRNA affect the ability of the resulting mutant ribosome to make protein. The present invention thus provides a system whereby the mutations in the plasmid-encoded rRNA gene only affect the amount of GFP and CAT produced. A decrease in plasmid ribosome function makes the cell more sensitive to chloramphenicol and reduces the amount of green fluorescence of the cells. Translation of the other mRNAs in the cell is unaffected since these mRNAs are translated only by ribosomes that come from the chromosome. Hence, cells containing functional mutants may be identified and isolated via the selectable marker.

Example 2B

Construction of the Pa 16S pRNA228 Plasmid

A plasmid construct of the present invention identified as the Pa 16S Ec H9 pRNA228 plasmid, is set forth in FIGS. 2 and 7. *E. coli* cells contain a single chromosome with seven copies of the rRNA genes and all of the genes for the ribosomal proteins. The plasmid, Pa 16S Ec H9 pRNA228, in the cell contains a genetically engineered copy of one of the 16S rRNA genes from *P. aeruginosa* wherein the *P. aeruginosa* helix 9 sequence has been replaced with the corresponding *E. coli* sequence, and two genetically engineered genes that are not normally found in *E. coli*, referred to herein as a "selectable markers." One gene encodes the protein chloramphenicol acetyltransferase (CAT). This protein renders cells resistant to chloramphenicol by chemically modifying the antibiotic. Another gene, the Green Fluorescent Protein (GFP), is also included in the system. GFP facilitates high-throughput functional analysis. The amount of green light produced upon irradiation with ultraviolet light is proportional to the amount of GFP present in the cell.

Ribosomes from Pa 16S Ec H9 pRNA228 have an altered ASD sequence. Therefore, the ribosomes can only translate mRNAs that have an altered SD sequence. Only two genes in the cell produce mRNAs with altered SD sequences that may be translated by the plasmid-encoded ribosomes: the CAT and GFP gene. Mutations in rRNA affect the ability of the resulting mutant ribosome to make protein. The present invention thus provides a system whereby the mutations in the plasmid-encoded rRNA gene only affect the amount of GFP and CAT produced. A decrease in plasmid ribosome function makes the cell more sensitive to chloramphenicol and reduces the amount of green fluorescence of the cells. Translation of the other mRNAs in the cell is unaffected since these mRNAs are translated only by ribosomes that come from the chromosome. Hence, cells containing functional mutants may be identified and isolated via the selectable marker.

Example 2C

Construction of the pKan5-T1T2 and pKanPa-S20 Plasmid

A plasmid construct of the present invention identified as the pKan5-T1T2 plasmid, is set forth in FIGS. 3 and 8. The plasmid, pKan5-T1T2, is a PACYC177 derivative. It was used in the preparation of the pKanPa-S20 plasmid, which encodes the *P. aeruginosa* S20 protein, which is set forth in FIGS. 4 and 9.

Example 3

Genetic System for Functional Analysis of Ribosomal RNA

Identification of Functionally Important Regions of rRNA. Functionally important regions of rRNA molecules that may be used as drug targets using a functional genomics approach may be identified through a series of steps. Namely, in step I.a., the entire rRNA gene is randomly mutated using error-prone PCR or another generalized mutational strategy. In step I.b., a host cell is then transformed with a mutagenized plasmid comprising: an rRNA gene having a mutant ASD sequence, at least one mutation in said rRNA gene, and a genetically engineered gene which encodes a selectable marker having a mutant SD sequence, and production of the rRNA genes from the plasmid are induced by growing the cells in the presence of IPTG. In step I.c., the CAT gene is used to select mutants that are functional by plating the transformed cells onto growth medium containing chloramphenicol. In step I.d., individual clones from each of the colonies obtained in step I.c. are isolated. In step I.e., the plasmid DNA from each of the individual clones from step I.d. is isolated. In step I.f., the rRNA genes contained in each of the plasmids that had been isolated in step I.e. are sequenced. In step I.g., the function of each of the mutants from step I.f. is assessed by measuring the amount of GFP produced by each clone from step I.e. upon induction of the rRNA operon. In step I.h., a functional genomics database is assembled containing the sequence and functional data from steps I.f. and I.g. In step I.i., functionally important regions of the rRNA gene that will serve as drug targets are identified. Functionally important regions may be identified by comparing the sequences of all of the functional genomics database constructed in step I.g. and correlating the sequence with the amount of GFP protein produced. Contiguous sequences of three or more rRNA nucleotides, in which substitution of the nucleotides in the region produces significant loss of function, will constitute a functionally important region and therefore a potential drug target. Helix 9 (SEQ ID NO 1 and SEQ ID NO 2) is a functional important region, as shown herein, and is therefore a potential drug target.

Isolation of Functional Variants of the Target Regions. A second aspect of the invention features identification of mutations of the target site that might lead to antibiotic resistance using a process termed, "instant evolution", as described below. In step II.a., for a given target region identified in step I.i., each of the nucleotides in the target region is simultaneously randomly mutated using standard methods of molecular mutagenesis, such as cassette mutagenesis or PCR mutagenesis, and cloned into the plasmid of step I.b. to form a plasmid pool containing random mutations at each of the nucleotide positions in the target region. In step II.b., the resulting pool of plasmids containing random mutations from step II.a. is used to transform E. coli cells and form a library of clones, each of which contains a unique combination of mutations in the target region. In step II.c., the library of mutant clones from step II.b. is grown in the presence of IPTG to induce production of the mutant rRNA genes. In step II.d., the induced mutants are plated on medium containing chloramphenicol, and CAT is used to select clones of rRNA mutants containing nucleotide combinations of the target region that produce functional ribosomes. In step II.e., the functional clones isolated in step II.d. are sequenced and GFP is used to measure ribosome function in each one. In step II.f., the data from step II.e. are incorporated into a mutational database.

Isolation of Drug Leads. In step III.a., the database in step II.f. is analyzed to identify functionally-important nucleotides and nucleotide motifs within the target region. In step III.b., the information from step III.a. is used to synthesize a series of oligonucleotides that contain the functionally important nucleotides and nucleotide motifs identified in step III.a. In step III.c., the oligonucleotides from step III.b. are used to sequentially screen compounds and compound libraries to identify compounds that recognize (bind to) the functionally important sequences and motifs. In step III.d., compounds that bind to all of the oligonucleotides are counterscreened against oligonucleotides and/or other RNA containing molecules to identify drug candidates. "Drug candidates" are compounds that 1) bind to all of the oligonucleotides containing the functionally important nucleotides and nucleotide motifs, but do not bind to molecules that do not contain the functionally important nucleotides and nucleotide motifs and 2) do not recognize human ribosomes. Drug candidates selected by the methods of the present invention therefore recognize all of the functional variants of the target sequence, i.e., the target cannot be mutated in a way that the drug cannot bind, without causing loss of function to the ribosome.

Example 4

Genetic System for Studying Protein Synthesis

All plasmids are maintained and expressed in E. coli DH5 (e.g. supE44, hsdR17, recA1, endA1, gyrA96, thi-1 and relA1; Hanahan, D. (1983) J. Mol. Biol. 166:557-580). To induce synthesis of plasmid-derived rRNA from the lacUV5 promoter, IPTG is added to a final concentration of 1 mM. Chloramphenicol acetyltransferase activity will be determined essentially as described by Nielsen et al. (1989) Anal. Biochem. 179: 19-23. Cultures for CAT assays are grown in LB-Ap100. MIC will be determined by standard methods in microtiter plates as described in Lee, K., et al. (1997) J. Mol. Biol. 269: 732-743. Procedures are followed as in outlined in Example 4 of Cunningham et al. (WO 2004/003511).

Example 5

In Vivo Determination of RNA Structure-Function Relationships

Bacterial strains and media. Plasmids are maintained and expressed in E. coli DH5 (e.g. supE44, hsdR17, recA1, endA1, gyrA9 and thi-1; Hanahan, D. (1983) J. Mol. Biol. 166:557-580). Cultures are grown in LB medium (Luria, S. E. & Burrous, J. W. (1957) J. Bacteriol. 74:461-476) or LB medium containing 100 μg/ml ampicillin (LB-Ap100). To induce synthesis of plasmid-derived rRNA from the lacUV5 promoter, IPTG is added to a final concentration of 1 mM at the times indicated in each experiment. Strains are transformed by electroporation (Dower, W. J., et al. (1988) Nucl. Acids Res. 16: 6127) using a Gibco-BRL Cell Porator. Transformants are grown in SOC medium (Hanahan, 1983, supra) for one hour prior to plating on selective medium to allow expression of plasmid-derived genes.

Chloramphenicol acetyltransferase assays. CAT activity is determined essentially as described (Nielsen, D. A. et al. (1989) Anal. Biochem. 60:191-227). Cultures for CAT assays will be grown in LB-Ap100. Briefly, 0.5 ml aliquots of mid-log cultures (unless otherwise indicated) is added to an equal volume of 500 mM Tris-HCl (pH8) and lysed using 0.01% (w/v) SDS and chloroform (Miller, J. H. (1992) A Short Course in Bacterial Genetics, (Miller, J. H., ed.), pp. 71-80, Cold Spring Harbor Laboratory Press, Cold Spring Harbor, N.Y.). The resulting lysate is either be used directly or diluted in assay buffer prior to use. Assay mixtures contain cell extract (5 μl or 10 μl), 250 mM Tris (pH 8), 214 μM butyryl-coenzyme A (Bu-CoA), and 40 μM [$^3$H]chloramphenicol in a 125 μl volume. Two concentrations of lysate are assayed for one hour at 37° C. to ensure that the signal was proportional to protein concentrations. The product, butyryl-[$^3$H]chloramphenicol is extracted into 2,6,10,14-tetramethylpentadecane: xylenes (2:1) and measured directly in a Beckman LS-3801 liquid scintillation counter. Blanks are prepared exactly as described above, except that uninoculated LB medium was used instead of culture.

Minimum inhibitory concentration determination. MICs are determined by standard methods in microtiter plates or on solid medium. Overnight cultures grown in LB-Ap100 are diluted and induced in the same medium containing 1 mM IPTG for three hours. Approximately 10$^4$ induced cells are then added to wells (or spotted onto solid medium) containing LB-Ap100+IPTG (1 mM) and chloramphenicol at increasing concentrations. Cultures are grown for 24 hours and the lowest concentration of chloramphenicol that completely inhibited growth is designated as the MIC.

Oligoribonucleotide synthesis. Oligoribonucleotides are synthesized on solid support with the phosphoramidite method (Capaldi, D. & Reese, C. (1994) *Nucl. Acids Res.* 22:2209-2216) on a Cruachem PS 250 DNA/RNA synthesizer. Oligomers are removed from solid support and deprotected by treatment with ammonia and acid following the manufacturer's recommendations. The RNA is purified on a silica gel Si500F TLC plate (Baker) eluted for five hours with n-propanol/ammonia/water (55:35:10, by vol.). Bands are visualized with an ultraviolet lamp and the least mobile band was cut out and eluted three times with 1 ml of purified water. Oligomers are further purified with a Sep-pak C-18 cartridge (Waters) and desalted by continuous-flow dialysis (BRL). Purities are checked by analytical C-8 HPLC (Perceptive Biosystems).

INCORPORATION BY REFERENCE

All of the references including, without limitation, U.S. patents, U.S. patent application publications, published international applications and journal articles cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A plasmid comprising a first nucleic acid sequence and a second nucleic acid sequence; wherein said first nucleic acid sequence encodes a *Pseudomonas aeruginosa* 16S rRNA comprising a mutant Anti-Shine-Dalgarno sequence, a mutant helix 9 sequence, and at least one additional mutation outside the Anti-Shine-Dalgarno region; and said second sequence encodes a selectable marker having a mutant Shine-Dalgarno sequence; wherein said mutant Anti-Shine-Dalgarno sequence specifically hybridizes to said mutant Shine-Dalgarno sequence.

2. The plasmid of claim 1, wherein said mutant helix 9 sequence is SEQ ID NO: 1.

3. The plasmid of claim 1, wherein the selectable marker is chosen from the group consisting of chloramphenicol acetyltransferase, green fluorescent protein, and both chloramphenicol acetyltransferase and green fluorescent protein.

4. The plasmid of claim 1, wherein the mutant Anti-Shine-Dalgarno sequence is selected from the group consisting of SEQ ID NOs: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146 and 148.

5. The plasmid of claim 1, wherein the mutant Shine-Dalgarno sequence is selected from the group consisting of SEQ ID NOs: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145 and 147.

6. The plasmid of claim 1, wherein the mutant Shine-Dalgarno sequence and the mutant Anti-Shine-Dalgarno sequence are a complementary pair selected from the group consisting of SEQ ID NOs: 7 and 8, 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, 131 and 132, 133 and 134, 135 and 136, 137 and 138, 139 and 140, 141 and 142, 143 and 144, 145 and 146, and 147 and 148.

7. The plasmid of claim 1, wherein the complementary mutant Shine-Dalgarno and mutant Anti-Shine-Dalgarno pair permits translation by the rRNA of the selectable marker.

8. The plasmid of claim 1, wherein the selectable marker is chloramphenicol acetyltransferase.

9. The plasmid of claim 1, wherein the selectable marker is green fluorescent protein.

10. The plasmid of claim 1, wherein the DNA sequence encoding the rRNA gene is under the control of an inducible promoter.

11. A cell comprising the plasmid of claim 1.

12. The cell of claim 11, wherein the mutations in the rRNA gene affect the quantity of selectable marker produced.

13. The cell of claim 11, wherein the cell is a bacterial cell.

14. The cell of claim 11, wherein the cell is an *E. coli* cell.

15. A cell comprising first and second plasmids, wherein the first plasmid comprises a first nucleic acid sequence and a second nucleic acid sequence; wherein said first nucleic acid sequence encodes a *Pseudomonas aeruginosa* 16S rRNA comprising a mutant Anti-Shine-Dalgarno sequence and at least one additional mutation outside the Anti-Shine-Dalgarno region; and said second sequence encodes a selectable marker having a mutant Shine-Dalgarno sequence; wherein said mutant Anti-Shine-Dalgarno sequence specifically hybridizes to said mutant Shine-Dalgarno sequence, and the second plasmid comprises a *Pseudomonas aeruginosa* S20 gene.

16. The cell of claim 15, wherein the mutation in the 16S rRNA gene affects the quantity of selectable marker produced.

17. The cell of claim 15, wherein the cell is a bacterial cell.

18. The cell of claim 15, wherein the cell is an *E. coli* cell.

* * * * *

SEQUENCE LISTING

```
<160> NUMBER OF SEQ ID NOS: 155

<210> SEQ ID NO 1
<211> LENGTH: 19
<212> TYPE: RNA
<213> ORGANISM: Escherichia coli

<400> SEQUENCE: 1
auaacgucgc aagaccaaa                                                  19

<210> SEQ ID NO 2
<211> LENGTH: 19
<212> TYPE: RNA
<213> ORGANISM: Pseudomonas aeruginosa

<400> SEQUENCE: 2
auacguccug agggagaaa                                                  19

<210> SEQ ID NO 3
<211> LENGTH: 13115
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3 ttacgcccg  ccctgccact  catcgcagta  ctgttgtaat  tcattaagca  ttctgccgac      60
atggaagcca  tcacagacgg  catgatgaac  ctgaatcgcc  agcggcatca  gcaccttgtc     120
gccttgcgta  taatatttgc  ccatggtgaa  aacgggggcg  aagaagttgt  ccatattggc     180
cacgtttaaa  tcaaaactgg  tgaaactcac  ccagggattg  gctgagacga  aaaacatatt     240
ctcaataaac  cctttaggga  aataggccag  gttttcaccg  taacacgcca  catcttgcga     300
atatatgtgt  agaaactgcc  ggaaatcgtc  gtggtattca  ctccagagcg  atgaaaacgt     360
ttcagtttgc  tcatggaaaa  cggtgtaaca  agggtgaaca  ctatcccata  tcaccagctc     420
accgtctttc  attgccatac  ggaattccgg  atgagcattc  atcaggcggg  caagaatgtg     480
```

```
aataaaggcc ggataaaact tgtgcttatt tttctttacg gtctttaaaa aggccgtaat      540
atccagctga acggtctggt tataggtaca ttgagcaact gactgaaatg cctcaaaatg      600
ttctttacga tgccattggg atatatcaac ggtggtatat ccagtgattt ttttctccat      660
ttgcggaggg atatgaaagc ggccgcttcc acacattaaa ctagttcgat gattaattgt      720
caacagctcg ccggcggcac ctcgctaacg gattcaccac tccaagaatt ggagccaatc      780
gattcttgcg gagaactgtg aatgcgcaaa ccaacccttg cagaacata tccatcgcgt       840 ccgccatctc cagcagccgc acgcggcgca tctcgggcag cgttgggtcc tggccacggg      900
tgcgcatgat cgtgctcctg tcgttgagga cccggctagg ctggcggggt tgccttactg      960
gttagcagaa tgaatcaccg atacgcgagc gaacgtgaag cgactgctgc tgcaaaacgt     1020
ctgcgacctg agcaacaaca tgaatggtct tcggtttccg tgtttcgtaa agtctggaaa     1080
cgcggaagtc agcgccctgc accattatgt tccggatctg ggtacccgca ttcacagttc     1140
tccgcaagaa tcgattggct ccaattcttg gagtggtgaa tccgttagcg aggtgccgcc     1200
ggcgagctgt tgacaattaa tcatcgaact agtttaatgt gtggaagcgg ccgctttcat     1260
atccctccgc aaatggagaa aaaatcact gctagcaaag gagaagaact tttcactgga     1320
gttgtcccaa ttcttgttga attagatggt gatgttaatg gcacaaaatt ttctgtcagt     1380
ggagagggtg aaggtgatgc tacatacgga aagcttaccc ttaaatttat ttgcactact     1440
ggaaaactac ctgttccatg ccaacacttt gtcactactt tctcttatgg tgttcaatgc     1500
ttttcccgtt atccggatca tatgaaacgg catgactttt tcaagagtgc catgcccgaa     1560
ggttatgtac aggaacgcac tatatctttc aaagatgacg ggaactacaa gacgcgtgct     1620
gaagtcaagt ttgaaggtga tacccttgtt aatcgtatcg agttaaaagg tattgatttt     1680
aaagaagatg gaaacattct cggacacaaa ctcgagtaca actataactc acacaatgta     1740
tacatcacgg cagacaaaca aaagaatgga atcaaagcta acttcaaaat tcgccacaac     1800
attgaagatg gatccgttca actagcagac cattatcaac aaaatactcc aattggcgat     1860
ggccctgtcc ttttaccaga caaccattac ctgtcgacac aatctgccct ttcgaaagat     1920
cccaacgaaa agcgtgacca catggtcctt cttgagtttg taactgctgc tgggattaca     1980
catggcatgg atgagctcta caaataatct agtcgtagcg ccgatggtag tgtgggtct     2040 ccccatgcga gagtagggaa ctgccaggca tcaaataaaa cgaaaggctc agtcgaaaga     2100
ctgggccttt cgttttatct gttgtttgtc ggtgaacgct ctcctgagta ggacaaatcc     2160
gccgggagcg gatttgaacg ttgcgaagca acggcccgga gggtggcggg caggacgccc     2220
gccataaact gccaggcatc aaattaagca gaaggccatc ctgacggatg ccttttttgc     2280
gtttctacaa actcttcctg tcgtcagtgc aggtaccgag ctcgaattca ctggccgtcg     2340
ttttacaacg tcgtgactgg gaaaaccctg gcgttaccca acttaatcgc cttgcagcac     2400 atccccettt cgccaggcat cgcaggatgc tgctggctac cctgtggaac acctacatct     2460
gtattaacga agcgctggca ttgaccctga gtgatttttc tctggtcccg ccgcatccat     2520
accgccagtt gtttaccctc acaacgttcc agtaaccggg catgttcatc atcagtaacc     2580
cgtatcgtga gcatcctctc tcgtttcatc ggtatcatta ccccatgaa cagaaattcc     2640 cccttacacg gaggcatcaa gtgaccaaac aggaaaaaac cgcccttaac atggcccgct     2700
ttatcagaag ccagacatta acgcttctgg agaaactcaa cgagctggac gcggatgaac     2760
aggcagacat ctgtgaatcg cttcacgacc acgctgatga gctttaccgc agctgcctcg     2820
cgcgtttcgg tgatgacggt gaaaacctct gacacatgca gctcccggag acggtcacag     2880
```

```
cttgtctgta agcggatgcc gggagcagac aagcccgtca gggcgcgtca gcgggtgttg   2940
gcgggtgtcg gggcgcagcc atgacccagt cacgtagcga tagcggagtg tatactggct   3000
taactatgcg gcatcagagc agattgtact gagagtgcac catatgcggt gtgaaatacc   3060
gcacagatgc gtaaggagaa ataccgcat  caggcgctct  tccgcttcct  cgctcactga   3120
ctcgctgcgc tcggtcgttc ggctgcggcg agcggtatca gctcactcaa aggcggtaat   3180
acggttatcc acagaatcag gggataacgc aggaaagaac atgtgagcaa aaggccagca   3240
aaaggccagg aaccgtaaaa aggccgcgtt gctggcgttt ttccataggc tccgcccccc   3300
tgacgagcat cacaaaaatc gacgctcaag tcagaggtgg cgaaacccga caggactata   3360
aagataccag gcgtttcccc ctggaagctc cctcgtgcgc tctcctgttc cgaccctgcc   3420
gcttaccgga tacctgtccg cctttctccc ttcgggaagc gtggcgcttt ctcatagctc   3480
acgctgtagg tatctcagtt cggtgtaggt cgttcgctcc aagctgggct gtgtgcacga   3540 acccccccgtt cagcccgacc gctgcgcctt atccggtaac tatcgtcttg agtccaaccc   3600
ggtaagacac gacttatcgc cactggcagc agccactggt aacaggatta gcagagcgag   3660
gtatgtaggc ggtgctacag agttcttgaa gtggtggcct aactacggct acactagaag   3720
gacagtattt ggtatctgcg ctctgctgaa gccagttacc ttcggaaaaa gagttggtag   3780
ctcttgatcc ggcaaacaaa ccaccgctgg tagcggtggt ttttttgttt gcaagcagca   3840
gattacgcgc agaaaaaaag gatctcaaga agatcctttg atcttttcta cggggtctga   3900
cgctcagtgg aacgaaaact cacgttaagg gattttggtc atgagattat caaaaaggat   3960
cttcacctag atccttttaa attaaaaatg aagttttaaa tcaatctaaa gtatatatga   4020
gtaaacttgg tctgacagtt accaatgctt aatcagtgag gcacctatct cagcgatctg   4080
tctatttcgt tcatccatag ttgcctgact ccccgtcgtg tagataacta cgatacggga   4140
gggcttacca tctggcccca gtgctgcaat gataccgcga gacccacgct caccggctcc   4200
agatttatca gcaataaacc agccagccgg aagggccgag cgcagaagtg gtcctgcaac   4260
tttatccgcc tccatccagt ctattaattg ttgccgggaa gctagagtaa gtagttcgcc   4320
agttaatagt ttgcgcaacg ttgttgccat tgctgcaggc atcgtggtgt cacgctcgtc   4380
gtttggtatg gcttcattca gctccggttc ccaacgatca aggcgagtta catgatcccc   4440
catgttgtgc aaaaaagcgg ttagctcctt cggtcctccg atcgttgtca gaagtaagtt   4500
ggccgcagtg ttatcactca tggttatggc agcactgcat aattctctta ctgtcatgcc   4560
atccgtaaga tgcttttctg tgactggtga gtactcaacc aagtcattct gagaatagtg   4620
tatgcggcga ccgagttgct cttgcccggc gtcaacacgg ataataccg  cgccacatag   4680 cagaacttta aaagtgctca tcattggaaa acgttcttcg gggcgaaaac tctcaaggat   4740
cttaccgctg ttgagatcca gttcgatgta acccactcgt gcacccaact gatcttcagc   4800
atcttttact ttcaccagcg tttctgggtg agcaaaaaca ggaaggcaaa atgccgcaaa   4860
aaagggaata agggcgacac ggaaatgttg aatactcata ctcttccttt ttcaatatta   4920
ttgaagcatt tatcagggtt attgtctcat gagcggatac atatttgaat gtatttagaa   4980
aaataaacaa ataggggttc cgcgcacatt tccccgaaaa gtgccacctg acgtctaaga   5040
aaccattatt atcatgacat taacctataa aaataggcgt atcacgaggc cctttcgtct   5100
tcaagaattc tcatgtttga cagcttatca tcgataagct ttaatgcggt agtttatcac   5160
agttaaattg ctaacgcagt caggcaccgt gtatgaaatc taacaatgcg ctcatcgtca   5220
tcctcggcac cgtcaccctg gatgctgtag gcataggctt ggttatgccg gtactgccgg   5280
```

```
gcctcttgcg ggatatcgtc cattccgaca gcatcgccag tcactatggc gtgctgctag    5340
cgctatatgc gttgatgcaa tttctatgcg cacccgttct cggagcactg tccgaccgct    5400
ttggccgccg cccagtcctg ctcgcttcgc tacttggagc cactatcgac tacgcgatca    5460
tggcgaccac acccgtcctg tggatcccag acgagttaag tcaccatacg ttagtacagg    5520
ttgccactct tttggcagac gcagacctac ggctacaata gcgaagcggt cctggtattc    5580
atgtttaaaa atactgtcgc gatagccaaa acggcactct ttggcagtta agcgcacttg    5640
cttgcctgtc gccagttcaa cagaatcaac ataagcgcaa actcgctgta attctacgcc    5700
ataagcacca atattctgga taggtgatga gccgacacaa ccaggaatta atgccagatt    5760
ttccagacca ggcataccct tcctgcaaagt gtattttacc agacgatgcc agttttctcc    5820
ggctcctaca tgtaaatacc acgcatcagg ttcatcatga atttcgatac ctttgatccg    5880
gttgatgatc cctgcaggcc cttaaggcca tttaaatggc gcgccgatca atgccaaatg    5940
tgttccaggg ttttaaggag tggttcatag ctgcttttcct gatgcaaaaa cgaggctagt    6000
ttaccgtatc tgtgggggga tggcttgtag atatgacgac aggaagagtt tgtagaaacg    6060
caaaaaggcc atccgtcagg atggccttct gcttaatttg atgcctggca gtttatggcg    6120
ggcgtcctgc ccgccaccct ccgggccgtt gcttcgcaac gttcaaatcc gctcccggcg    6180
gatttgtcct actcaggaga gcgttcaccg acaaacaaca gataaaacga aaggcccagt    6240
ctttcgactg agcctttcgt tttatttgat gcctggcagt tccctactct cgcatgggga    6300
gacccccacac taccatcggc gctacggcgt ttcacttctg agttcggcat ggggtcaggt    6360
gggaccaccg cgctactgcc gccaggcaaa ttctgtttta tcagaccgct tctgcgttct    6420
gatttaatct gtatcaggct gaaaatcttc tctcatccgc caaaacagct tcggcgttgt    6480
aaggttaagc ctcacggttc attagtaccg gttagctcaa cgcatcgctg cgcttacaca    6540
cccggcctat caacgtcgtc gtcttcaacg ttccttcagg accctaaaag ggtcagggag    6600
aactcatctc ggggcaagtt tcgtgcttag atgctttcag cacttatctc ttccgcattt    6660
agctaccggg cagtgccatt ggcatgacaa cccgaacacc agtgatgcgt ccactccggt    6720
cctctcgtac taggagcagc cccctcagt tctccagcgc ccacggcaga tagggaccga    6780
actgtctcac gacgttctaa acccagctcg cgtaccactt taaatggcga acagccatac    6840
ccttgggacc tacttcagcc ccaggatgtg atgagccgac atcgaggtgc caaacaccgc    6900
cgtcgatatg aactcttggg cggtatcagc ctgttatccc cggagtacct tttatccgtt    6960
gagcgatggc ccttccattc agaaccaccg gatcactatg acctgctttc gcacctgctc    7020
gcgccgtcac gctcgcagtc aagctggctt atgccattgc actaacctcc tgatgtccga    7080
ccaggattag ccaaccttcg tgctcctccg ttactcttta ggaggagacc gccccagtca    7140
aactacccac cagacactgt ccgcaacccg gattacgggt caacgttaga acatcaaaca    7200
ttaaagggtg gtatttcaag gtcggctcca tgcagactgg cgtccacact tcaaagcctc    7260
ccacctatcc tacacatcaa ggctcaatgt tcagtgtcaa gctatagtaa aggttcacgg    7320
ggtctttccg tcttgccgcg ggtacactgc atcttcacag cgagttcaat ttcactgagt    7380
ctcgggtgga gacagcctgg ccatcattac gccattcgtg caggtcggaa cttacccgac    7440
aaggaatttc gctaccttag gaccgttata gttacgccg ccgtttaccg gggcttcgat    7500
caagagcttc gcttgcgcta accccatcaa ttaaccttcc ggcaccgggc aggcgtcaca    7560
ccgtatacgt ccactttcgt gtttgcacag tgctgtgttt ttaataaaca gttgcagcca    7620
gctggtatct tcgactgatt tcagctccat ccgcgaggga cctcacctac atatcagcgt    7680
```

```
gccttctccc gaagttacgg caccatttg cctagttcct tcacccgagt tctctcaagc  7740
gccttggtat tctctacctg accacctgtg tcggtttggg gtacgatttg atgttacctg  7800
atgcttagag gcttttcctg gaagcagggc atttgttgct tcagcaccgt agtgcctcgt  7860
catcacgcct cagccttgat tttccggatt tgcctggaaa accagcctac acgcttaaac  7920
cgggacaacc gtcgcccggc caacatagcc ttctccgtcc cccttcgca gtaacaccaa  7980 gtacaggaat attaacctgt ttcccatcga ctacgccttt cggcctcgcc ttaggggtcg  8040
actcaccctg ccccgattaa cgttggacag gaacccttgg tcttccggcg agcgggcttt  8100
tcacccgctt tatcgttact tatgtcagca ttcgcacttc tgatacctcc agcatgcctc  8160
acagcacacc ttcgcaggct tacagaacgc tcccctaccc aacaacgcat aagcgtcgct  8220
gccgcagctt cggtgcatgg tttagccccg ttacatcttc cgcgcaggcc gactcgacca  8280
gtgagctatt acgctttctt taaatgatgg ctgcttctaa gccaacatcc tggctgtctg  8340
ggccttccca catcgtttcc cacttaacca tgactttggg accttagctg gcggtctggg  8400
ttgtttccct cttcacgacg gacgttagca cccgccgtgt gtctcccgtg ataacattct  8460
ccggtattcg cagtttgcat cgggttggta agtcggatg acccccttgc cgaaacagtg  8520
ctctaccccc ggagatgaat tcacgaggcg ctacctaaat agctttcggg gagaaccagc  8580
tatctcccgg tttgattggc ctttcacccc cagccacaag tcatccgcta atttttcaac  8640
attagtcggt tcggtcctcc agttagtgtt acccaacctt caacctgccc atggctagat  8700
caccgggttt cgggtctata ccctgcaact taacgcccag ttaagactcg gtttcccttc  8760 ggctcccta ttcggttaac cttgctacag aatataagtc gctgacccat tatacaaaag  8820
gtacgcagtc acacgcctaa gcgtgctccc actgcttgta cgtacacggt tcaggttct  8880 ttttcactcc cctcgccggg gttcttttcg cctttccctc acggtactgg ttcactatcg  8940
gtcagtcagg agtatttagc cttggaggat ggtcccccca tattcagaca ggataccacg  9000
tgtcccgccc tactcatcga gctcacagca tgtgcatttt tgtgtacggg gctgtcaccc  9060
tgtatcgcgc gccttccag acgcttccac taacacacac actgattcag gctctgggct  9120
gctccccgtt cgctcgccgc tactggggga atctcggttg atttcttttc ctcggggtac  9180
ttagatgttt cagttccccc ggttcgcctc attaacctat ggattcagtt aatgatagtg  9240
tgtcgaaaca cactgggttt ccccattcgg aaatcgccgg ttataacggt tcatatcacc  9300
ttaccgacgc ttatcgcaga ttagcacgtc cttcatcgcc tctgactgcc agggcatcca  9360
ccgtgtacgc ttagtcgctt aacctcacaa cccgaagatg tttctttcga ttcatcatcg  9420
tgttgcgaaa atttgagaga ctcacgaaca actctcgttg ttcagtgttt caattttcag  9480
cttgatccag atttttaaag agcaaatatc tcaaacatca cccgaagatg agttttgaga  9540
tattaaggtc ggcgactttc actcacaaac cagcaagtgg cgtcccctag gggattcgaa  9600
cccctgttac cgccgtgaaa gggcggtgtc ctgggcctct agacgaaggg gacacgaaaa  9660
ttgcttatca cgccgttgcgt gatatttcg tgtagggtga gctttcatta atagaaagcg  9720
aacggcctta ttctcttcag cctcactccc aacgcgtaaa cgccttgctt ttcacttct  9780 atcagacaat ctgtgtgagc actacaaagt acgcttcttt aaggtaatcc catgatccaa  9840
ccgcaggttc ccctacggtt accttgttac gacttcaccc cagtcatgaa tcactccgtg  9900
gtaaccgtcc cccttgcggt tagactagct acttctggag caacccactc ccatggtgtg  9960
acgggcggtg tgtacaaggc ccgggaacgt attcaccgtg acattctgat tcacgattac  10020
tagcgattcc gacttcacgc agtcgagttg cagactgcga tccggactac gatcggtttt  10080
```

```
atgggattag ctccacctcg cggcttggca acccttttgta ccgaccattg tagcacgtgt    10140
gtagccctgg ccgtaagggc catgatgact tgacgtcatc cccaccttcc tccggtttgt    10200
caccggcagt ctccttagag tgcccacccg aggtgctggt aactaaggac aagggttgcg    10260
ctcgttacgg gacttaaccc aacatctcac gacacgagct gacgacagcc atgcagcacc    10320
tgtgtctgag ttcccgaagg caccaatcca tctctggaaa gttctcagca tgtcaaggcc    10380
aggtaaggtt cttcgcgttg cttcgaatta aaccacatgc tccaccgctt gtgcgggccc    10440
ccgtcaattc atttgagttt taaccttgcg gccgtactcc ccaggcggtc gacttatcgc    10500
gttagctgcg ccactaagat ctcaaggatc caacggcta gtcgacatcg tttacggcgt    10560
ggactaccag ggtatctaat cctgtttgct ccccacgctt tcgcacctca gtgtcagtat    10620
cagtccaggt ggtcgccttc gccactggtg ttccttccta tatctacgca tttcaccgct    10680
acacaggaaa ttccaccacc ctctaccgta ctctagctca gtagttttgg atgcagttcc    10740
caggttgagc ccggggattt cacatccaac ttgctgaacc acctacgcgc gctttacgcc    10800
cagtaattcc gattaacgct tgcacccttc gtattaccgc ggctgctggc acgaagttag    10860
ccggtgctta ttctgttggt aacgtcaaaa cagcaaggta ttaacttact gcccttcctc    10920
ccaacttaaa gtgctttaca atccgaagac cttcttcaca cacgcggcat ggctggatca    10980
ggctttcgcc cattgtccaa tattccccac tgctgcctcc cgtaggagtc tggaccgtgt    11040
ctcagttcca gtgtgactga tcatcctctc agaccagtta cggatcgtcg ccttggtagg    11100
cctttacccc accaactagc taatccgacc taggctcatc tgatagcgtg aggtccgaag    11160
atcccccact ttctccctca ggacgtatgc ggtattagcg cccgtttccg gacgttatcc    11220
cccactacca ggcagattcc taggcattac tcacccgtcc gccgctgaat ccaggagcaa    11280
gctcccttca tccgctcgac ttgcatgtgt taggcctgcc gccagcgttc aatctgagcc    11340
atgatcaaac tcttcaattt aaaagtttga cgctcaaaga attaaacttc gtaatgaatt    11400
acgtgttcac tcttgagact tggtattcat ttttcgtctt gcgacgttaa gaatccgtat    11460
cttcgagtgc ccacacagat tgtctgataa attgttaaag agcagtgccg cttcgctttt    11520
tctcagcggc cgctgtgtga aattgttatc cgctcacaat tccacacatt atacgagccg    11580
gaagcataaa gtgtaaagcc tggggtgcct aatgagtgag ctaactcaca ttaattgcgt    11640
tgcgctcact gcccgctttc cagtcgggaa acctgtcgtg ccagctgcat taatgaatcg    11700
gccaacgcgc ggggagaggc ggtttgcgta ttgggcgcca gggtggtttt tcttttcacc    11760
agtgagacgg gcaacagctg attgcccttc accgcctggc cctgagagag ttgcagcaag    11820
cggtccacgc tggtttgccc cagcaggcga aaatcctgtt tgatggtggt tgacggcggg    11880
atataacatg agctgtcttc ggtatcgtcg tatcccacta ccgagatatc cgcaccaacg    11940
cgcagcccgg actcggtaat ggcgcgcatt gcgcccagcg ccatctgatc gttggcaacc    12000
agcatcgcag tgggaacgat gccctcattc agcatttgca tggtttgttg aaaaccggac    12060
atggcactcc agtcgccttc ccgttccgct atcggctgaa tttgattgcg agtgagatat    12120
ttatgccagc cagccagacg cagacgcgcc gagacagaac ttaatgggcc cgctaacagc    12180
gcgatttgct ggtgbcccaa tgcgaccaga tgctccacgc ccagtcgcgt accgtcttca    12240
tgggagaaaa taatactgtt gatgggtgtc tggtcagaga catcaagaaa taacgccgga    12300
acattagtgc aggcagcttc cacagcaatg gcatcctggt catccagcgg atagttaata    12360
atcagcccac tgacccgttg cgcgagaaga ttgtgcaccg ccgctttaca ggcttcgacg    12420
ccgcttcgtt ctaccatcga caccaccacg ctggcaccca gttgatcggc gcgagattta    12480
```

```
atcgccgcga caatttgcga cggcgcgtgc agggccagac tggaggtggc aacgccaatc   12540
agcaacgact gtttgcccgc cagttgttgt gccacgcggt tgggaatgta attcagctcc   12600
gccatcgccg cttccacttt ttcccgcgtt ttcgcagaaa cgtggctggc ctggttcacc   12660
acgcgggaaa cggtctgata agagacaccg gcatactctg cgacatcgta taacgttact   12720
ggtttcacat tcaccaccct gaattgactc tcttccgggc gctatcatgc cataccgcga   12780
aaggttttgc accattcgat ggtgtcggat cctctagccg gacccacttg cggccacgat   12840
ccgtccgccg taaggctcat accgttaatt attcccccc acgggagacc tgagcaaact   12900
gccctcaggc atttgagaag cacagggtca cactgcttcg ggtagtcaat aaaccggtaa   12960
accagcaata gacataagcg gctatttaac gaccctgccc tgaaccgacg accgggtcga   13020
atttgctttc gaatttctgc cattcatccg cttattatca cttattcagg cgtagcacca   13080
ggcgtttaag ggcaccaata actgccttaa aaaaa                              13115
```

<210> SEQ ID NO 4
<211> LENGTH: 13115
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 4

```
ttacgccccg ccctgccact catcgcagta ctgttgtaat tcattaagca ttctgccgac     60
atggaagcca tcacagacgg catgatgaac ctgaatcgcc agcggcatca gcaccttgtc    120
gccttgcgta taatatttgc ccatggtgaa aacgggggcg aagaagttgt ccatattggc    180 cacgttaaa tcaaaactgg tgaaactcac ccagggattg gctgagacga aaacatatt     240 ctcaataaac cctttaggga ataggccag gttttcaccg taacacgcca catcttgcga    300
atatatgtgt agaaactgcc ggaaatcgtc gtggtattca ctccagagcg atgaaaacgt    360
ttcagtttgc tcatggaaaa cggtgtaaca agggtgaaca ctatcccata tcaccagctc    420
accgtctttc attgccatac ggaattccgg atgagcattc atcaggcggg caagaatgtg    480
aataaaggcc ggataaaact tgtgcttatt tttctttacg gtctttaaaa aggccgtaat    540
atccagctga acggtctggt tataggtaca ttgagcaact gactgaaatg cctcaaaatg    600
ttctttacga tgccattggg atatatcaac ggtggtatat ccagtgattt ttttctccat    660
ttgcggaggg atatgaaagc ggccgcttcc acacattaaa ctagttcgat gattaattgt    720
caacagctcg ccggcggcac ctcgctaacg gattcaccac tccaagaatt ggagccaatc    780
gattcttgcg gagaactgtg aatgcgcaaa ccaacccttg gcagaacata tccatcgcgt    840
ccgccatctc cagcagccgc acgcggcgca tctcgggcag cgttgggtcc tggccacggg    900
tgcgcatgat cgtgctcctg tcgttgagga cccggctagg ctggcggggt tgccttactg    960
gttagcagaa tgaatcaccg atacgcgagc gaacgtgaag cgactgctgc tgcaaaacgt   1020
ctgcgacctg agcaacaaca tgaatggtct tcggtttccg tgtttcgtaa agtctggaaa   1080
cgcggaagtc agcgccctgc accattatgt tccggatctg ggtacccgca ttcacagttc   1140
tccgcaagaa tcgattggct ccaattcttg gagtggtgaa tccgttagcg aggtgccgcc   1200
ggcgagctgt tgacaattaa tcatcgaact agtttaatgt gtggaagcgg ccgctttcat   1260
atccctccgc aaatggagaa aaaaatcact gctagcaaag gagaagaact tttcactgga   1320
gttgtcccaa ttcttgttga attagatggt gatgttaatg ggcacaaatt ttctgtcagt   1380
```

-continued

```
ggagagggtg aaggtgatgc tacatacgga aagcttaccc ttaaatttat ttgcactact    1440
ggaaaactac ctgttccatg gccaacactt gtcactactt tctcttatgg tgttcaatgc    1500
ttttcccgtt atccggatca tatgaaacgg catgactttt tcaagagtgc catgcccgaa    1560
ggttatgtac aggaacgcac tatatctttc aaagatgacg ggaactacaa gacgcgtgct    1620
gaagtcaagt ttgaaggtga tacccttgtt aatcgtatcg agttaaaagg tattgatttt    1680
aaagaagatg gaaacattct cggacacaaa ctcgagtaca actataactc acacaatgta    1740
tacatcacgg cagacaaaca aaagaatgga atcaaagcta acttcaaaat tcgccacaac    1800
attgaagatg gatccgttca actagcagac cattatcaac aaaatactcc aattggcgat    1860
ggccctgtcc ttttaccaga caaccattac ctgtcgacac aatctgccct ttcgaaagat    1920
cccaacgaaa agcgtgacca catggtcctt cttgagtttg taactgctgc tgggattaca    1980
catggcatgg atgagctcta caaataatct agtcgtagcg ccgatggtag tgtgggtct     2040 ccccatgcga gagtagggaa ctgccaggca tcaaataaaa cgaaaggctc agtcgaaaga    2100
ctgggccttt cgttttatct gttgtttgtc ggtgaacgct ctcctgagta ggacaaatcc    2160
gccgggagcg gatttgaacg ttgcgaagca acggcccgga gggtggcggg caggacgccc    2220
gccataaact gccaggcatc aaattaagca gaaggccatc ctgacggatg gccttttgc     2280 gtttctacaa actcttcctg tcgtcagtgc aggtaccgag ctcgaattca ctggccgtcg    2340
ttttacaacg tcgtgactgg gaaaaccctg gcgttaccca acttaatcgc cttgcagcac    2400 atccccttt cgccaggcat cgcaggatgc tgctggctac cctgtggaac acctacatct     2460
gtattaacga agcgctggca ttgaccctga gtgattttt c tctggtcccg ccgcatccat    2520
accgccagtt gtttaccctc acaacgttcc agtaaccggg catgttcatc atcagtaacc    2580
cgtatcgtga gcatcctctc tcgtttcatc ggtatcatta cccccatgaa cagaaattcc    2640
cccttacacg gaggcatcaa gtgaccaaac aggaaaaaac cgcccttaac atggcccgct    2700
ttatcagaag ccagacatta acgcttctgg agaaactcaa cgagctggac gcggatgaac    2760
aggcagacat ctgtgaatcg cttcacgacc acgctgatga gctttaccgc agctgcctcg    2820
cgcgtttcgg tgatgacggt gaaaacctct gacacatgca gctcccggag acggtcacag    2880
cttgtctgta agcggatgcc gggagcagac aagcccgtca gggcgcgtca gcgggtgttg    2940
gcgggtgtcg gggcgcagcc atgacccagt cacgtagcga tagcggagtg tatactggct    3000
taactatgcg gcatcagagc agattgtact gagagtgcac catatgcggt gtgaaatacc    3060
gcacagatgc gtaaggagaa aataccgcat caggcgctct ccgcttcct cgctcactga     3120 ctcgctgcgc tcggtcgttc ggctgcggcg agcggtatca gctcactcaa aggcggtaat    3180
acggttatcc acagaatcag gggataacgc aggaaagaac atgtgagcaa aaggccagca    3240
aaaggccagg aaccgtaaaa aggccgcgtt gctggcgttt ttccataggc tccgcccccc    3300
tgacgagcat cacaaaaatc gacgctcaag tcagaggtgg cgaaacccga caggactata    3360
aagataccag gcgtttcccc ctggaagctc cctcgtgcgc tctcctgttc cgaccctgcc    3420
gcttaccgga tacctgtccg cctttctccc ttcgggaagc gtggcgcttt ctcatagctc    3480
acgctgtagg tatctcagtt cggtgtaggt cgttcgctcc aagctgggct gtgtgcacga    3540
accccccgtt cagcccgacc gctgcgcctt atccggtaac tatcgtcttg agtccaaccc    3600
ggtaagacac gacttatcgc cactggcagc agccactggt aacaggatta gcagagcgag    3660
gtatgtaggc ggtgctacag agttcttgaa gtggtggcct aactacggct acactagaag    3720
gacagtattt ggtatctgcg ctctgctgaa gccagttacc ttcggaaaaa gagttggtag    3780
```

```
ctcttgatcc ggcaaacaaa ccaccgctgg tagcggtggt tttttgtttt gcaagcagca   3840
gattacgcgc agaaaaaaag gatctcaaga agatcctttg atcttttcta cggggtctga   3900
cgctcagtgg aacgaaaact cacgttaagg gattttggtc atgagattat caaaaaggat   3960
cttcacctag atccttttaa attaaaaatg aagttttaaa tcaatctaaa gtatatatga   4020
gtaaacttgg tctgacagtt accaatgctt aatcagtgag gcacctatct cagcgatctg   4080
tctatttcgt tcatccatag ttgcctgact ccccgtcgtg tagataacta cgatacggga   4140
gggcttacca tctggcccca gtgctgcaat gataccgcga gacccacgct caccggctcc   4200
agatttatca gcaataaacc agccagccgg aagggccgag cgcagaagtg gtcctgcaac   4260
tttatccgcc tccatccagt ctattaattg ttgccgggaa gctagagtaa gtagttcgcc   4320
agttaatagt ttgcgcaacg ttgttgccat tgctgcaggc atcgtggtgt cacgctcgtc   4380
gtttggtatg gcttcattca gctccggttc ccaacgatca aggcgagtta catgatcccc   4440
catgttgtgc aaaaaagcgg ttagctcctt cggtcctccg atcgttgtca gaagtaagtt   4500
ggccgcagtg ttatcactca tggttatggc agcactgcat aattctctta ctgtcatgcc   4560
atccgtaaga tgcttttctg tgactggtga gtactcaacc aagtcattct gagaatagtg   4620
tatgcggcga ccgagttgct cttgcccggc gtcaacacgg gataataccg cgccacatag   4680
cagaacttta aaagtgctca tcattggaaa acgttcttcg gggcgaaaac tctcaaggat   4740
cttaccgctg ttgagatcca gttcgatgta acccactcgt gcacccaact gatcttcagc   4800
atcttttact ttcaccagcg tttctgggtg agcaaaaaca ggaaggcaaa atgccgcaaa   4860
aaagggaata agggcgacac ggaaatgttg aatactcata ctcttccttt ttcaatatta   4920
ttgaagcatt tatcagggtt attgtctcat gagcggatac atatttgaat gtatttagaa   4980
aaataaacaa ataggggttc cgcgcacatt tccccgaaaa gtgccacctg acgtctaaga   5040
aaccattatt atcatgacat taacctataa aaataggcgt atcacgaggc cctttcgtct   5100
tcaagaattc tcatgtttga cagcttatca tcgataagct ttaatgcggt agtttatcac   5160
agttaaattg ctaacgcagt caggcaccgt gtatgaaatc taacaatgcg ctcatcgtca   5220
tcctcggcac cgtcaccctg gatgctgtag gcataggctt ggttatgccg gtactgccgg   5280
gcctcttgcg ggatatcgtc cattccgaca gcatcgccag tcactatggc gtgctgctag   5340
cgctatatgc gttgatgcaa tttctatgcg cacccgttct cggagcactg tccgaccgct   5400
ttggccgccg cccagtcctg ctcgcttcgc tacttggagc cactatcgac tacgcgatca   5460
tggcgaccac acccgtcctg tggatcccag acgagttaag tcaccatacg ttagtacagg   5520
ttgccactct tttggcagac gcagacctac ggctacaata gcgaagcggt cctggtattc   5580
atgtttaaaa atactgtcgc gatagccaaa acggcactct ttggcagtta agcgcacttg   5640
cttgcctgtc gccagttcaa cagaatcaac ataagcgcaa actcgctgta attctacgcc   5700
ataagcacca atattctgga taggtgatga gccgacacaa ccaggaatta atgccagatt   5760
ttccagacca ggcatacctt cctgcaaagt gtattttacc agacgatgcc agttttctcc   5820
ggctcctaca tgtaaatacc acgcatcagg ttcatcatga atttcgatac ctttgatccg   5880
gttgatgatc cctgcaggcc cttaaggcca tttaaatggc gcgccgatca atgccaaatg   5940
tgttccaggg ttttaaggag tggttcatag ctgcttccct gatgcaaaaa cgaggctagt   6000
ttaccgtatc tgtgggggga tggcttgtag atatgacgac aggaagagtt tgtagaaacg   6060
caaaaaggcc atccgtcagg atggccttct gcttaatttg atgcctggca gtttatggcg   6120
ggcgtcctgc ccgccaccct ccgggccgtt gcttcgcaac gttcaaatcc gctcccggcg   6180
```

```
gatttgtcct actcaggaga gcgttcaccg acaaacaaca gataaaacga aaggcccagt    6240 cttcgactg agcctttcgt tttatttgat gcctggcagt tccctactct cgcatgggga     6300
gaccccacac taccatcggc gctacggcgt ttcacttctg agttcggcat ggggtcaggt    6360
gggaccaccg cgctactgcc gccaggcaaa ttctgtttta tcagaccgct tctgcgttct    6420
gatttaatct gtatcaggct gaaaatcttc tctcatccgc caaaacagct tcggcgttgt    6480
aaggttaagc ctcacggttc attagtaccg gttagctcaa cgcatcgctg cgcttacaca    6540
cccggcctat caacgtcgtc gtcttcaacg ttccttcagg acccttaaag ggtcagggag    6600
aactcatctc ggggcaagtt tcgtgcttag atgctttcag cacttatctc ttccgcattt    6660
agctaccggg cagtgccatt ggcatgacaa cccgaacacc agtgatgcgt ccactccggt    6720
cctctcgtac taggagcagc cccctcagt  tctccagcgc ccacggcaga tagggaccga    6780
actgtctcac gacgttctaa acccagctcg cgtaccactt taaatggcga acagccatac    6840
ccttgggacc tacttcagcc ccaggatgtg atgagccgac atcgaggtgc caaacaccgc    6900
cgtcgatatg aactcttggg cggtatcagc ctgttatccc cggagtacct tttatccgtt    6960
gagcgatggc ccttccattc agaaccaccg gatcactatg acctgctttc gcacctgctc    7020
gcgccgtcac gctcgcagtc aagctggctt atgccattgc actaacctcc tgatgtccga    7080
ccaggattag ccaaccttcg tgctcctccg ttactcttta ggaggagacc gccccagtca    7140
aactacccac cagacactgt ccgcaacccg gattacgggt caacgttaga acatcaaaca    7200
ttaaagggtg gtatttcaag gtcggctcca tgcagactgg cgtccacact tcaaagcctc    7260
ccacctatcc tacacatcaa ggctcaatgt tcagtgtcaa gctatagtaa aggttcacgg    7320 ggtcttttccg tcttgccgcg ggtacactgc atcttcacag cgagttcaat ttcactgagt    7380
ctcgggtgga gacagcctgg ccatcattac gccattcgtg caggtcggaa cttacccgac    7440
aaggaatttc gctaccttag gaccgttata gttacggccg ccgtttaccg ggcttcgat    7500 caagagcttc gcttgcgcta accccatcaa ttaaccttcc ggcaccgggc aggcgtcaca    7560
ccgtatacgt ccactttcgt gtttgcacag tgctgtgttt ttaataaaca gttgcagcca    7620
gctggtatct tcgactgatt tcagctccat ccgcgaggga cctcacctac atatcagcgt    7680
gccttctccc gaagttacgg caccattttg cctagttcct tcacccgagt tctctcaagc    7740
gccttggtat tctctacctg accacctgtg tcggtttggg gtacgatttg atgttacctg    7800
atgcttagag gcttttcctg gaagcagggc atttgttgct tcagcaccgt agtgcctcgt    7860
catcacgcct cagccttgat tttccggatt gcctggaaa  accagcctac acgcttaaac    7920
cgggacaacc gtcgcccggc caacatagcc ttctccgtcc cccttcgca  gtaacaccaa    7980 gtacaggaat attaacctgt ttcccatcga ctacgccttt cggcctcgcc ttaggggtcg    8040
actcaccctg ccccgattaa cgttggacag gaacccttgg tcttccggcg agcgggcttt    8100
tcacccgctt tatcgttact tatgtcagca ttcgcacttc tgatacctcc agcatgcctc    8160
acagcacacc ttcgcaggct tacagaacgc tcccctaccc aacaacgcat aagcgtcgct    8220
gccgcagctt cggtgcatgg tttagcccg  ttacatcttc cgcgcaggcc gactcgacca    8280
gtgagctatt acgctttctt taaatgatgg ctgcttctaa gccaacatcc tggctgtctg    8340
ggccttccca tcgtttcc   cacttaacca tgactttggg accttagctg gcggtctggg    8400
ttgtttccct cttcacgacg acgttagca  cccgccgtgt gtctccgtg  ataacattct    8460 ccggtattcg cagtttgcat cgggttggta agtcggatg  accccttgc  cgaaacagtg    8520 ctctacccc  ggagatgaat tcacgaggcg ctacctaaat agctttcggg gagaaccagc    8580
```

```
tatctcccgg tttgattggc ctttcacccc cagccacaag tcatccgcta attttttcaac   8640
attagtcggt tcggtcctcc agttagtgtt acccaacctt caacctgccc atggctagat   8700
caccgggttt cgggtctata ccctgcaact taacgcccag ttaagactcg gtttcccttc   8760
ggctccccta ttcggttaac cttgctacag aatataagtc gctgacccat tatacaaaag   8820
gtacgcagtc acacgcctaa gcgtgctccc actgcttgta cgtacacggt ttcaggttct   8880
ttttcactcc cctcgccggg gttcttttcg ccttttccctc acggtactgg ttcactatcg   8940
gtcagtcagg agtatttagc cttggaggat ggtcccccca tattcagaca ggataccacg   9000
tgtcccgccc tactcatcga gctcacagca tgtgcatttt tgtgtacggg gctgtcaccc   9060
tgtatcgcgc gccttttcag acgcttccac taacacacac actgattcag gctctgggct   9120
gctcccccgtt cgctcgccgc tactggggga atctcggttg atttcttttc ctcggggtac   9180
ttagatgttt cagttccccc ggttcgcctc attaacctat ggattcagtt aatgatagtg   9240
tgtcgaaaca cactgggttt ccccattcgg aaatcgccgg ttataacggt tcatatcacc   9300
ttaccgacgc ttatcgcaga ttagcacgtc cttcatcgcc tctgactgcc agggcatcca   9360
ccgtgtacgc ttagtcgctt aacctcacaa cccgaagatg tttctttcga ttcatcatcg   9420
tgttgcgaaa atttgagaga ctcacgaaca actctcgttg ttcagtgttt caattttcag   9480
cttgatccag attttttaaag agcaaatatc tcaaacatca cccgaagatg agttttgaga   9540
tattaaggtc ggcgactttc actcacaaac cagcaagtgg cgtcccctag gggattcgaa   9600
ccccctgttac cgccgtgaaa gggcggtgtc ctgggcctct agacgaaggg gacacgaaaa   9660
ttgcttatca cgcgttgcgt gatattttcg tgtagggtga gctttcatta atagaaagcg   9720
aacggcctta ttctcttcag cctcactccc aacgcgtaaa cgccttgctt ttcactttct   9780
atcagacaat ctgtgtgagc actacaaagt acgcttcttt aaggtaatcc catgatccaa   9840
ccgcaggttc ccctacggtt accttgttac gacttcaccc cagtcatgaa tcactccgtg   9900
gtaaccgtcc cccttgcggt tagactagct acttctggag caacccactc ccatggtgtg   9960
acgggcggtg tgtacaaggc ccgggaacgt attcaccgtg acattctgat tcacgattac  10020
tagcgattcc gacttcacgc agtcgagttg cagactgcga tccggactac gatcggtttt  10080
atgggattag ctccacctcg cggcttggca acccttttgta ccgaccattg tagcacgtgt  10140
gtagccctgg ccgtaagggc catgatgact tgacgtcatc cccaccttcc tccggtttgt  10200
caccggcagt ctccttagag tgcccacccg aggtgctggt aactaaggac aagggttgcg  10260
ctcgttacgg gacttaaccc aacatctcac gacacgagct gacgacagcc atgcagcacc  10320
tgtgtctgag ttcccgaagg caccaatcca tctctggaaa gttctcagca tgtcaaggcc  10380
aggtaaggtt cttcgcgttg cttcgaatta aaccacatgc tccaccgctt gtgcgggccc  10440
ccgtcaattc atttgagttt taaccttgcg gccgtactcc ccaggcggtc gacttatcgc  10500
gttagctgcg ccactaagat ctcaaggatc ccaacggcta gtcgacatcg tttacgcgt  10560
ggactaccag ggtatctaat cctgtttgct ccccacgctt tcgcacctca gtgtcagtat  10620
cagtccaggt ggtcgccttc gccactggtg ttccttccta tatctacgca tttcaccgct  10680
acacaggaaa ttccaccacc ctctaccgta ctctagctca gtagttttgg atgcagttcc  10740
caggttgagc ccggggattt cacatccaac ttgctgaacc acctacgcgc gctttacgcc  10800
cagtaattcc gattaacgct tgcacccttc gtattaccgc ggctgctggc acgaagttag  10860
ccggtgctta ttctgttggt aacgtcaaaa cagcaaggta ttaacttact gcccttcctc  10920
ccaacttaaa gtgctttaca atccgaagac cttcttcaca cacgcggcat ggctggatca  10980
```

```
ggctttcgcc cattgtccaa tattccccac tgctgcctcc cgtaggagtc tggaccgtgt    11040
ctcagttcca gtgtgactga tcatcctctc agaccagtta cggatcgtcg ccttggtagg    11100
cctttacccc accaactagc taatccgacc taggctcatc tgatagcgtg aggtccgaag    11160
atcccccact ttggtcttgc gacgttatgc ggtattagcg cccgtttccg gacgttatcc    11220
cccactacca ggcagattcc taggcattac tcacccgtcc gccgctgaat ccaggagcaa    11280
gctcccttca tccgctcgac ttgcatgtgt taggcctgcc gccagcgttc aatctgagcc    11340
atgatcaaac tcttcaattt aaaagtttga cgctcaaaga attaaacttc gtaatgaatt    11400
acgtgttcac tcttgagact tggtattcat ttttcgtctt gcgacgttaa gaatccgtat    11460
cttcgagtgc ccacacagat tgtctgataa attgttaaag agcagtgccg cttcgctttt    11520
tctcagcggc cgctgtgtga aattgttatc cgctcacaat tccacacatt atacgagccg    11580
gaagcataaa gtgtaaagcc tggggtgcct aatgagtgag ctaactcaca ttaattgcgt    11640
tgcgctcact gcccgctttc cagtcgggaa acctgtcgtg ccagctgcat taatgaatcg    11700
gccaacgcgc ggggagaggc ggtttgcgta ttgggcgcca gggtggtttt tcttttcacc    11760
agtgagacgg gcaacagctg attgcccttc accgcctggc cctgagagag ttgcagcaag    11820
cggtccacgc tggtttgccc cagcaggcga aaatcctgtt tgatggtggt tgacggcggg    11880
atataacatg agctgtcttc ggtatcgtcg tatcccacta ccgagatatc cgcaccaacg    11940
cgcagcccgg actcggtaat ggcgcgcatt gcgcccagcg ccatctgatc gttggcaacc    12000
agcatcgcag tgggaacgat gccctcattc agcatttgca tggtttgttg aaaaccggac    12060
atggcactcc agtcgccttc ccgttccgct atcggctgaa tttgattgcg agtgagatat    12120
ttatgccagc cagccagacg cagacgcgcc gagacagaac ttaatgggcc cgctaacagc    12180
gcgatttgct ggtgbcccaa tgcgaccaga tgctccacgc ccagtcgcgt accgtcttca    12240
tgggagaaaa taatactgtt gatgggtgtc tggtcagaga catcaagaaa taacgccgga    12300
acattagtgc aggcagcttc cacagcaatg gcatcctggt catccagcgg atagttaata    12360
atcagcccac tgacccgttg cgcgagaaga ttgtgcaccg ccgctttaca ggcttcgacg    12420
ccgcttcgtt ctaccatcga caccaccacg ctggcaccca gttgatcggc gcgagattta    12480
atcgccgcga caatttgcga cggcgcgtgc agggccagac tggaggtggc aacgccaatc    12540
agcaacgact gtttgcccgc cagttgttgt gccacgcggt tgggaatgta attcagctcc    12600
gccatcgccg cttccacttt ttcccgcgtt ttcgcagaaa cgtggctggc ctggttcacc    12660
acgcgggaaa cggtctgata agagacaccg gcatactctg cgacatcgta taacgttact    12720
ggtttcacat tcaccaccct gaattgactc tcttccgggc gctatcatgc cataccgcga    12780
aaggttttgc accattcgat ggtgtcggat cctctagccg gacccacttg cggccacgat    12840
ccgtccgccg taaggctcat accgttaatt attccccccc acgggagacc tgagcaaact    12900
gccctcaggc atttgagaag cacagggtca cactgcttcg ggtagtcaat aaaccggtaa    12960
accagcaata gacataagcg gctatttaac gaccctgccc tgaaccgacg accgggtcga    13020
atttgctttc gaatttctgc cattcatccg cttattatca cttattcagg cgtagcacca    13080
ggcgtttaag ggcaccaata actgccttaa aaaaa                               13115
```

<210> SEQ ID NO 5  
<211> LENGTH: 4459  
<212> TYPE: DNA  
<213> ORGANISM: Artificial Sequence  
<220> FEATURE:  
<223> OTHER INFORMATION: Description of Artificial Sequence: Synthetic nucleotide sequence

```
<400> SEQUENCE: 5
actcaccagt cacagaaaag catcttacgg atggcatgac agtaagagaa ttatgcagtg    60
ctgccataac catgagtgat aacactgcgg ccaacttact tctgacaacg atcggaggac   120
cgaaggagct aaccgctttt ttgcacaaca tgggggatca tgtaactcgc cttgatcgtt   180
gggaaccgga gctgaatgaa gccataccaa acgacgagcg tgacaccacg atgcctgcag   240
caatggcaac aacgttgcgc aaactattaa ctggcgaact acttactcta gcttcccggc   300
aacaattaat agactggatg gaggcggata aagttgcagg accacttctg cgctcggccc   360
ttccggctgg ctggtttatt gctgataaat ctggagccgg tgagcgtggg tctcgcggta   420
tcattgcagc actggggcca gatggtaagc cctcccgtat cgtagttatc tacacgacgg   480
ggagtcaggc aactatggat gaacgaaata gacagatcgc tgagataggt gcctcactga   540
ttaagcattg gtaactgtca gaccaagttt actcatatat actttagatt gatttaaaac   600 ttcatttta atttaaaagg atctaggtga agatcctttt tgataatctc atgaccaaaa   660
tcccttaacg tgagttttcg ttccactgag cgtcagaccc cttaataaga tgatcttctt   720
gagatcgttt tggtctgcgc gtaatctctt gctctgaaaa cgaaaaaacc gccttgcagg   780
gcggtttttc gaaggttctc tgagctacca actctttgaa ccgaggtaac tggcttggag   840
gagcgcagtc accaaaactt gtcctttcag tttagcctta accggcgcat gacttcaaga   900
ctaactcctc taaatcaatt accagtggct gctgccagtg gtgcttttgc atgtctttcc   960
gggttggact caagacgata gttaccggat aaggcgcagc ggtcggactg aacggggggt  1020
tcgtgcatac agtccagctt ggagcgaact gcctacccgg aactgagtgt caggcgtgga  1080
atgagacaaa cgcggccata acagcggaat gacaccggta aaccgaaagg caggaacagg  1140
agagcgcacg agggagccgc caggggggaaa cgcctggtat ctttatagtc ctgtcgggtt  1200
tcgccaccac tgatttgagc gtcagatttc gtgatgcttg tcaggggggc ggagcctatg  1260
gaaaaacggc tttgccgcgg ccctctcact tccctgttaa gtatcttcct ggcatcttcc  1320
aggaaatctc cgccccgttc gtaagccatt tccgctcgcc gcagtcgaac gaccgagcgt  1380
agcgagtcag tgagcgagga agcggaatat atcctgtatc acatattctg ctgacgcacc  1440
ggtgcagcct ttttctcct gccacatgaa gcacttcact gacaccctca tcagtgccaa  1500
catagtaagc cagtatacac tccgctagcg ctgaggtctg cctcgtgaag aaggtgttgc  1560
tgactcatac caggcctgaa tcgccccatc atccagccag aaagtgaggg agccacggtt  1620
gatgagagct ttgttgtagg tggaccagtt ggtgattttg aacttttgct ttgccacgga  1680
acggtctgcg ttgtcgggaa gatgcgtgat ctgatccttc aactcagcaa aagttcgatt  1740
tattcaacaa agccacgttg tgtctcaaaa tctctgatgt tacattgcac aagataaaaa  1800
tatatcatca tgaacaataa aactgtctgc ttacataaac agtaatacaa ggggtgttat  1860
gagccatatt caacgggaaa cgtcttgctc gaggccgcga ttaaattcca acatggatgc  1920
tgatttatat gggtataaat gggctcgcga taatgtcggg caatcaggtg cgacaatcta  1980
tcgattgtat gggaagcccg atgcgccaga gttgtttctg aaacatggca aaggtagcgt  2040
tgccaatgat gttacagatg agatggtcag actaaactgg ctgacggaat ttatgcctct  2100
tccgaccatc aagcatttta tccgtactcc tgatgatgca tggttactca ccactgcgat  2160
ccccgggaaa acagcattcc aggtattaga agaatatcct gattcaggtg aaaatattgc  2220
tgatgcgctg gcagtgttcc tgcgccggtt gcattcgatt cctgtttgta attgtccttt  2280
taacagcgat cgcgtatttc gtctcgctca ggcgcaatca cgaatgaata acggtttggt  2340
```

```
tgatgcgagt gattttgatg acgagcgtaa tggctggcct gttgaacaag tctggaaaga    2400
aatgcataaa cttttgccat tctcaccgga ttcagtcgtc actcatggtg atttctcact    2460
tgataacctt attttgacg aggggaaatt aataggttgt attgatgttg acgagtcgg     2520 aatcgcagac cgataccagg atcttgccat cctatggaac tgcctcggtg agttttctcc    2580
ttcattacag aaacggcttt ttcaaaaata tggtattgat aatcctgata tgaataaatt    2640
gcagtttcat ttgatgctcg atgagttttt ctaatcagaa ttggttaatt ggttgtaaca    2700
ctggcagagc attacgctga cttgacggga cggcggcttt gttgaataaa tcgaactttt    2760
gctgagttga aggatcagat cacgcatctt cccgacaacg cagaccgttc cgtggcaaag    2820
caaaagttca aaatcactag tcgaccatgg taccatcgat gcataatgtg cctgtcaaat    2880
ggacgaagca gggattctgc aaaccctatg ctactccgtc aagccgtcaa ttgtctgatt    2940
cgttaccaat tatgcaaact tgacggctac atcattcact ttttcttcac aaccggcacg    3000
gaactcgctc gggctggccc cggtgcattt tttaaatacc cgcgagaaat agagttgatc    3060
gtcaaaacca acattgcgac cgacggtggc gataggcatc cgggtggtgc tcaaaagcag    3120
cttcgcctgg ctgatacgtt ggtcctcgcg ccagcttaag acgctaatcc ctaactgctg    3180
gcggaaaaga tgtgacagac gcgacggcga caagcaaaca tgctgtgcga cgctggcgat    3240
atcaaaattg ctgtctgcca ggtgatcgct gatgtactga caagcctcgc gtacccgatt    3300
atccatcggt ggatggagcg actcgttaat cgcttccatg cgccgcagta acaattgctc    3360
aagcagattt atcgccagca gctccgaata gcgcccttcc ccttgcccgg cgttaatgat    3420
ttgcccaaac aggtcgctga atgcggctg gtgcgcttca tccgggcgaa agaaccccgt    3480
attggcaaat attgacggcc agttaagcca ttcatgccag taggcgcgcg acgaaagta    3540 aacccactgg tgataccatt cgcgagcctc cggatgacga ccgtagtgat gaatctctcc    3600
tggcgggaac agcaaaatat cacccggtcg gcaaacaaat tctcgtccct gattttcac    3660 cacccctga ccgcgaatgg tgagattgag aatataacct ttcattccca gcggtcggtc    3720 gataaaaaa tcgagataac cgttggcctc aatcggcgtt aaacccgcca ccagatgggc    3780
attaaacgag tatcccggca gcagggatc attttgcgct tcagccatac ttttcatact    3840
cccgccattc agagaagaaa ccaattgtcc atattgcatc agacattgcc gtcactgcgt    3900 ctttactgg ctcttctcgc taaccaaacc ggtaaccccg cttattaaaa gcattctgta    3960
acaaagcggg accaaagcca tgacaaaaac gcgtaacaaa agtgtctata atcacggcag    4020
aaaagtccac attgattatt tgcacggcgt cacactttgc tatgccatag catttttatc    4080
cataagatta gcggatccta cctgacgctt tttatcgcaa ctctctactg tttctccatg    4140
cggccgcatg caagcttcta gaataaaacg aaaggctcag tcgaaagact gggcctttcg    4200
ttttatctgt tgtttgtcgg tgaacgctct cctgagtagg acaaatccgc cgggagcgga    4260
tttgaacgtt gcgaagcaac ggcccggagg gtggcgggca ggacgcccgc cataaactgc    4320
caggcatcaa attaagcaga aggccatcct gacggatggc cttttgaat tcactggccg    4380 tcgttttaca acgtcgtgac tgggaaaacc ctggcgttac ccaacttaat cgccttgcag    4440
cacatccccc tttcgccag                                                4459
```

<210> SEQ ID NO 6
<211> LENGTH: 4759
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 6

| | | | | | |
|---|---|---|---|---|---|
| actcaccagt | cacagaaaag | catcttacgg | atggcatgac | agtaagagaa | ttatgcagtg | 60 |
| ctgccataac | catgagtgat | aacactgcgg | ccaacttact | tctgacaacg | atcggaggac | 120 |
| cgaaggagct | aaccgctttt | ttgcacaaca | tgggggatca | tgtaactcgc | cttgatcgtt | 180 |
| gggaaccgga | gctgaatgaa | gccataccaa | acgacgagcg | tgacaccacg | atgcctgcag | 240 |
| caatggcaac | aacgttgcgc | aaactattaa | ctggcgaact | acttactcta | gcttcccggc | 300 |
| aacaattaat | agactggatg | gaggcggata | aagttgcagg | accacttctg | cgctcggccc | 360 |
| ttccggctgg | ctggtttatt | gctgataaat | ctggagccgg | tgagcgtggg | tctcgcggta | 420 |
| tcattgcagc | actggggcca | gatggtaagc | cctcccgtat | cgtagttatc | tacacgacgg | 480 |
| ggagtcaggc | aactatggat | gaacgaaata | gacagatcgc | tgagataggt | gcctcactga | 540 |
| ttaagcattg | gtaactgtca | gaccaagttt | actcatatat | actttagatt | gatttaaaac | 600 |
| ttcatttttta | atttaaaagg | atctaggtga | agatcctttt | tgataatctc | atgaccaaaa | 660 |
| tcccttaacg | tgagttttcg | ttccactgag | cgtcagaccc | cttaataaga | tgatcttctt | 720 |
| gagatcgttt | tggtctgcgc | gtaatctctt | gctctgaaaa | cgaaaaaacc | gccttgcagg | 780 |
| gcggtttttc | gaaggttctc | tgagctacca | actctttgaa | ccgaggtaac | tggcttggag | 840 |
| gagcgcagtc | accaaaactt | gtcctttcag | tttagcctta | accggcgcat | gacttcaaga | 900 |
| ctaactcctc | taaatcaatt | accagtggct | gctgccagtg | gtgcttttgc | atgtctttcc | 960 |
| gggttggact | caagacgata | gttaccggat | aaggcgcagc | ggtcggactg | aacggggggt | 1020 |
| tcgtgcatac | agtccagctt | ggagcgaact | gcctacccgg | aactgagtgt | caggcgtgga | 1080 |
| atgagacaaa | cgcggccata | acagcggaat | gacaccggta | aaccgaaagg | caggaacagg | 1140 |
| agagcgcacg | agggagccgc | caggggggaaa | cgcctggtat | ctttatagtc | ctgtcgggtt | 1200 |
| tcgccaccac | tgatttgagc | gtcagatttc | gtgatgcttg | tcagggggc | ggagcctatg | 1260 |
| gaaaaacggc | tttgccgcgg | ccctctcact | tccctgttaa | gtatcttcct | ggcatcttcc | 1320 |
| aggaaatctc | cgccccgttc | gtaagccatt | tccgctcgcc | gcagtcgaac | gaccgagcgt | 1380 |
| agcgagtcag | tgagcgagga | agcggaatat | atcctgtatc | acatattctg | ctgacgcacc | 1440 |
| ggtgcagcct | ttttttctcct | gccacatgaa | gcacttcact | gacaccctca | tcagtgccaa | 1500 |
| catagtaagc | cagtatacac | tccgctagcg | ctgaggtctg | cctcgtgaag | aaggtgttgc | 1560 |
| tgactcatac | caggcctgaa | tcgccccatc | atccagccag | aaagtgaggg | agccacggtt | 1620 |
| gatgagagct | ttgttgtagg | tggaccagtt | ggtgattttg | aacttttgct | ttgccacgga | 1680 |
| acggtctgcg | ttgtcgggaa | gatgcgtgat | ctgatcctc | aactcagcaa | aagttcgatt | 1740 |
| tattcaacaa | agccacgttg | tgtctcaaaa | tctctgatgt | tacattgcac | aagataaaaa | 1800 |
| tatatcatca | tgaacaataa | aactgtctgc | ttacataaac | agtaatacaa | gggtgttat | 1860 |
| gagccatatt | caacgggaaa | cgtcttgctc | gaggccgcga | ttaaattcca | acatggatgc | 1920 |
| tgatttatat | gggtataaat | gggctcgcga | taatgtcggg | caatcaggtg | cgacaatcta | 1980 |
| tcgattgtat | gggaagcccg | atgcgccaga | gttgtttctg | aaacatggca | aaggtagcgt | 2040 |
| tgccaatgat | gttacagatg | agatggtcag | actaaactgg | ctgacggaat | ttatgcctct | 2100 |
| tccgaccatc | aagcatttta | tccgtactcc | tgatgatgca | tggttactca | ccactgcgat | 2160 |
| ccccgggaaa | acagcattcc | aggtattaga | agaatatcct | gattcaggtg | aaaatattgc | 2220 |
| tgatgcgctg | gcagtgttcc | tgcgccggtt | gcattcgatt | cctgtttgta | attgtccttt | 2280 |

```
taacagcgat cgcgtatttc gtctcgctca ggcgcaatca cgaatgaata acggtttggt    2340
tgatgcgagt gattttgatg acgagcgtaa tggctggcct gttgaacaag tctggaaaga    2400
aatgcataaa cttttgccat tctcaccgga ttcagtcgtc actcatggtg atttctcact    2460
tgataacctt attttgacg aggggaaatt aataggttgt attgatgttg acgagtcgg     2520 aatcgcagac cgataccagg atcttgccat cctatggaac tgcctcggtg agttttctcc    2580
ttcattacag aaacggcttt ttcaaaaata tggtattgat aatcctgata tgaataaatt    2640
gcagtttcat ttgatgctcg atgagttttt ctaatcagaa ttggttaatt ggttgtaaca    2700
ctggcagagc attacgctga cttgacggga cggcggcttt gttgaataaa tcgaactttt    2760
gctgagttga aggatcagat cacgcatctt cccgacaacg cagaccgttc cgtggcaaag    2820
caaaagttca aaatcactag tcgaccatgg taccatcgat gcataatgtg cctgtcaaat    2880
ggacgaagca gggattctgc aaaccctatg ctactccgtc aagccgtcaa ttgtctgatt    2940
cgttaccaat tatgacaact tgacggctac atcattcact ttttcttcac aaccggcacg    3000
gaactcgctc gggctggccc cggtgcattt tttaaatacc cgcgagaaat agagttgatc    3060
gtcaaaacca acattgcgac cgacggtggc gataggcatc cgggtggtgc tcaaaagcag    3120
cttcgcctgg ctgatacgtt ggtcctcgcg ccagcttaag acgctaatcc ctaactgctg    3180
gcggaaaaga tgtgacagac gcgacggcga caagcaaaca tgctgtgcga cgctggcgat    3240
atcaaaattg ctgtctgcca ggtgatcgct gatgtactga caagcctcgc gtacccgatt    3300
atccatcggt ggatggagcg actcgttaat cgcttccatg cgccgcagta acaattgctc    3360
aagcagattt atcgccagca gctccgaata gcgcccttcc ccttgccgg cgttaatgat    3420 ttgcccaaac aggtcgctga aatgcggctg gtgcgcttca tccgggcgaa agaaccccgt    3480
attggcaaat attgacggcc agttaagcca ttcatgccag taggcgcgcg gacgaaagta    3540
aacccactgg tgataccatt cgcgagcctc cggatgacga ccgtagtgat gaatctctcc    3600
tggcgggaac agcaaaatat cacccggtcg gcaaacaaat tctcgtccct gatttttcac    3660 cacccctga ccgcgaatgg tgagattgag aatataccct tcattccca gcggtcggtc     3720 gataaaaaaa tcgagataac cgttggcctc aatcggcgtt aaacccgcca ccagatgggc    3780
attaaacgag tatcccggca gcaggggatc attttgcgct tcagccatac ttttcatact    3840
cccgccattc agagaagaaa ccaattgtcc atattgcatc agacattgcc gtcactgcgt    3900
cttttactgg ctcttctcgc taaccaaacc ggtaaccccg cttattaaaa gcattctgta    3960
acaaagcggg accaaagcca tgacaaaaac gcgtaacaaa agtgtctata atcacggcag    4020
aaaagtccac attgattatt tgcacggcgt cacactttgc tatgccatag cattttttatc   4080 cataagatta gcggatccta cctgacgctt tttatcgcaa ctctctactg tttctccatg    4140
cggccgccta tttacccagt ttttttcgag gagctcgacg atggccaaca caccttccgc    4200
caaaaaacgc gccaaacagg ctgagaagcg tcgcagccac aacgccagcc tgcgctccat    4260
ggtgcgcacc tacatcaaga acgtcgtgaa agccatcgac gccaaggacc tggaaaaagc    4320
ccaggccgcc ttcaccgccg ctgtaccggt gatcgaccgc atggctgaca aaggcatcat    4380
ccacaagaac aaggctgctc gtcataagag ccgtctgagc ggccacatca aggccctcag    4440
caccgctgcc gcctaatcta gaataaaacg aaaggctcag tcgaaagact gggcctttcg    4500
ttttatctgt tgtttgtcgg tgaacgctct cctgagtagg acaaatccgc cgggagcgga    4560
tttgaacgtt gcgaagcaac ggcccggagg gtggcgggca ggacgcccgc cataaactgc    4620
caggcatcaa attaagcaga aggccatcct gacggatggc cttttttgaat tcactggccg    4680
```

```
tcgttttaca acgtcgtgac tgggaaaacc ctggcgttac ccaacttaat cgccttgcag    4740
cacatccccc tttcgccag                                                 4759
```

<210> SEQ ID NO 7
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(7)
<223> OTHER INFORMATION: a, c, g, u, unknown or other

<400> SEQUENCE: 7
cannnnncuc g                                                          11

<210> SEQ ID NO 8
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, u, unknown or other

<400> SEQUENCE: 8
ucannnnnuu a                                                          11

<210> SEQ ID NO 9
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
caggaggcuc g                                                          11

<210> SEQ ID NO 10
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucaccuccuu a                                                          11

<210> SEQ ID NO 11
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cagugugcuc g                                                          11

<210> SEQ ID NO 12
<211> LENGTH: 11

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ucacacacuu a                                                              11

<210> SEQ ID NO 13
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cauaucccuc g                                                              11

<210> SEQ ID NO 14
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ucagggauuu a                                                              11

<210> SEQ ID NO 15
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
caaacaccuc g                                                              11

<210> SEQ ID NO 16
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ucaagagguu a                                                              11

<210> SEQ ID NO 17
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cauaccucuc g                                                              11

<210> SEQ ID NO 18
<211> LENGTH: 11
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 18
ucaugagguu a                                                              11

<210> SEQ ID NO 19
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cauaauccuc g                                                              11

<210> SEQ ID NO 20
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ucagaggauu a                                                              11

<210> SEQ ID NO 21
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
caaauaccuc g                                                              11

<210> SEQ ID NO 22
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucaugagguu a                                                              11

<210> SEQ ID NO 23
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cacauaccuc g                                                              11

<210> SEQ ID NO 24
<211> LENGTH: 11
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 24
ucaagagguu a                                                                 11

<210> SEQ ID NO 25
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
caccgaccuc g                                                                 11

<210> SEQ ID NO 26
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ucaugggauu a                                                                 11

<210> SEQ ID NO 27
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
cauaucccuc g                                                                 11

<210> SEQ ID NO 28
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ucaugagguu a                                                                 11

<210> SEQ ID NO 29
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
caacuaccuc g                                                                 11

<210> SEQ ID NO 30
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 30
ucaagagguu a                                                         11

<210> SEQ ID NO 31
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
cauauaccuc g                                                         11

<210> SEQ ID NO 32
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucaagagguu a                                                         11

<210> SEQ ID NO 33
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(13)
<223> OTHER INFORMATION: a, c, g, u, unknown or other

<400> SEQUENCE: 33
cauauccuun nnnaaaug                                                  18

<210> SEQ ID NO 34
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ggaucauggg auua                                                      14

<210> SEQ ID NO 35
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35 cauauccuc gagaaaug                                                   18

<210> SEQ ID NO 36
<211> LENGTH: 14
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 36
ggaucauggg auua                                                         14

<210> SEQ ID NO 37
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cauaucccuc gagaaaug                                                     18

<210> SEQ ID NO 38
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggaucaccuc cuua                                                         14

<210> SEQ ID NO 39
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cauaucccuc cgcaaaug                                                     18

<210> SEQ ID NO 40
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggaucauggg auua                                                         14

<210> SEQ ID NO 41
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
cauaucccuc cgcaaaug                                                     18

<210> SEQ ID NO 42
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 42
ggaucaccuc cuua                                                    14

<210> SEQ ID NO 43
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cauaucccuc cugaaaug                                                18

<210> SEQ ID NO 44
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ggaucauggg auua                                                    14

<210> SEQ ID NO 45
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cauaucccuc ccaaaaug                                                18

<210> SEQ ID NO 46
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ggaucauggg auua                                                    14

<210> SEQ ID NO 47
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cauaucccuc cacaaaug                                                18

<210> SEQ ID NO 48
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
```
ggaucauggg auua 14

<210> SEQ ID NO 49
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(7)
<223> OTHER INFORMATION: a, c, g, u, unknown or other

<400> SEQUENCE: 49 cannnncuc g 11

<210> SEQ ID NO 50
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, u, unknown or other

<400> SEQUENCE: 50
ucannnnnuu a 11

<210> SEQ ID NO 51
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
caggaggcuc g 11

<210> SEQ ID NO 52
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ucaccuccuu a 11

<210> SEQ ID NO 53
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53 caaucccuc g 11

<210> SEQ ID NO 54
<211> LENGTH: 11
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 54
ucaagggauu a                                                              11

<210> SEQ ID NO 55
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
cauaccucuc g                                                              11

<210> SEQ ID NO 56
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ucaauggguu a                                                              11

<210> SEQ ID NO 57
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
cacaguccuc g                                                              11

<210> SEQ ID NO 58
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ucagacgauu a                                                              11

<210> SEQ ID NO 59
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
caaacgacuc g                                                              11

<210> SEQ ID NO 60
<211> LENGTH: 11
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 60
ucagugauuu a                                                            11

<210> SEQ ID NO 61
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61 cauaggguc g                                                             11

<210> SEQ ID NO 62
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62 ucauugggu a                                                             11

<210> SEQ ID NO 63
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
caucuugcuc g                                                            11

<210> SEQ ID NO 64
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ucaggagguu a                                                            11

<210> SEQ ID NO 65
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
caauuaucuc g                                                            11

<210> SEQ ID NO 66
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 66
ucagaauuuu a                                                            11

<210> SEQ ID NO 67
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
cacagaacug g                                                            11

<210> SEQ ID NO 68
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ucaaucaguu a                                                            11

<210> SEQ ID NO 69
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
caaaguucuc g                                                            11

<210> SEQ ID NO 70
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ucaaugaguu a                                                            11

<210> SEQ ID NO 71
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
caauucacuc g                                                            11

<210> SEQ ID NO 72
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
```
ucagugaauu a					11

<210> SEQ ID NO 73
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
caacucacuc g					11

<210> SEQ ID NO 74
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ucagaguguu a					11

<210> SEQ ID NO 75
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
caagggacuc g					11

<210> SEQ ID NO 76
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ucaugggauu a					11

<210> SEQ ID NO 77
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
caugguucug g					11

<210> SEQ ID NO 78
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ucaaagaguu a					11

```
<210> SEQ ID NO 79
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
cacaccacuc g                                                               11

<210> SEQ ID NO 80
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ucaugguuuu a                                                               11

<210> SEQ ID NO 81
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cacccaccuc g                                                               11

<210> SEQ ID NO 82
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ucaaaggguu a                                                               11

<210> SEQ ID NO 83
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
caucccaguc g                                                               11

<210> SEQ ID NO 84
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ucaagggguu a                                                              11

<210> SEQ ID NO 85
```

-continued

```
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
caaacuccuc g                                                              11

<210> SEQ ID NO 86
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ucauacuauu a                                                              11

<210> SEQ ID NO 87
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cauagaucuc g                                                              11

<210> SEQ ID NO 88
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ucaagaguuu a                                                              11

<210> SEQ ID NO 89
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
gaagugucuc g                                                              11

<210> SEQ ID NO 90
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ucaggagauu a                                                              11

<210> SEQ ID NO 91
<211> LENGTH: 11
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 91
caaauaucuc g                                                              11

<210> SEQ ID NO 92
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ucagagauuu a                                                              11

<210> SEQ ID NO 93
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cauaccucuc g                                                              11

<210> SEQ ID NO 94
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ucaugagguu a                                                              11

<210> SEQ ID NO 95
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
cauaguacuc g                                                              11

<210> SEQ ID NO 96
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ucauggauuu a                                                              11

<210> SEQ ID NO 97
<211> LENGTH: 11
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 97
caauccacug g                                                              11

<210> SEQ ID NO 98
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ucaguggauu a                                                              11

<210> SEQ ID NO 99
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
cacagaucuc g                                                              11

<210> SEQ ID NO 100
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucaggguuuu a                                                              11

<210> SEQ ID NO 101
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cauaggacuc g                                                              11

<210> SEQ ID NO 102
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
ucaugcuauu a                                                              11

<210> SEQ ID NO 103
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 103
caacuaacug g                                                              11

<210> SEQ ID NO 104
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ucauaguguu a                                                              11

<210> SEQ ID NO 105
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
caaauaucuc g                                                              11

<210> SEQ ID NO 106
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
ucaagguauu a                                                              11

<210> SEQ ID NO 107
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
caaauaucuc g                                                              11

<210> SEQ ID NO 108
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
ucaggagauu a                                                              11

<210> SEQ ID NO 109
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
```

```
caguggucuc g                                                         11

<210> SEQ ID NO 110
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
ucagaggauu a                                                         11

<210> SEQ ID NO 111
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
cauauugguc g                                                         11

<210> SEQ ID NO 112
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
ugauggaauu a                                                         11

<210> SEQ ID NO 113
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gaagcuacuc g                                                         11

<210> SEQ ID NO 114
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ucaggagauu a                                                         11

<210> SEQ ID NO 115
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
caauggacuc g                                                         11
```

```
<210> SEQ ID NO 116
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
ucaggagauu a                                                              11

<210> SEQ ID NO 117
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
caaggcgcuc g                                                              11

<210> SEQ ID NO 118
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ucagaggguu a                                                              11

<210> SEQ ID NO 119
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
caaacaucuc g                                                              11

<210> SEQ ID NO 120
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ucaagauguu a                                                              11

<210> SEQ ID NO 121
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
caucccacuc g                                                              11
```

<210> SEQ ID NO 122
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 122
ucaggguauu a                                                            11

<210> SEQ ID NO 123
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 123
cacugaucuc g                                                            11

<210> SEQ ID NO 124
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 124
ucagaggauu a                                                            11

<210> SEQ ID NO 125
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 125
cauauggcug g                                                            11

<210> SEQ ID NO 126
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 126
ucagggauuu a                                                            11

<210> SEQ ID NO 127
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 127
gaaagagcuc g                                                            11

<210> SEQ ID NO 128
<211> LENGTH: 11

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ugaagagguu a                                                              11

<210> SEQ ID NO 129
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
caacgaacug g                                                              11

<210> SEQ ID NO 130
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ucagaguguu a                                                              11

<210> SEQ ID NO 131
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
caucuaucuc g                                                              11

<210> SEQ ID NO 132
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucaggagauu a                                                              11

<210> SEQ ID NO 133
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
cauaccucuc g                                                              11

<210> SEQ ID NO 134
<211> LENGTH: 11
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 134
ucaugagguu a                                                               11

<210> SEQ ID NO 135
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
cauauaacuc g                                                               11

<210> SEQ ID NO 136
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ucaagagauu a                                                               11

<210> SEQ ID NO 137
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
caaauagcuc g                                                               11

<210> SEQ ID NO 138
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ucaugagguu a                                                               11

<210> SEQ ID NO 139
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
cacauagcuc g                                                               11

<210> SEQ ID NO 140
<211> LENGTH: 11
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 140
ucaugagguu a                                                              11

<210> SEQ ID NO 141
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
cagggaccuc g                                                              11

<210> SEQ ID NO 142
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ucaagagguu a                                                              11

<210> SEQ ID NO 143
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
cauaucgcuc g                                                              11

<210> SEQ ID NO 144
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144 ucauggguu a                                                               11

<210> SEQ ID NO 145
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
caacuaccug g                                                              11

<210> SEQ ID NO 146
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 146
ucaugagguu a                                                       11

<210> SEQ ID NO 147
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
cauauagcug g                                                       11

<210> SEQ ID NO 148
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ucaagagguu a                                                       11

<210> SEQ ID NO 149
<211> LENGTH: 1536
<212> TYPE: RNA
<213> ORGANISM: Pseudomonas aeruginosa

<400> SEQUENCE: 149
gaacugaaga guuugaucau ggcucagauu gaacgcuggc ggcaggccua acacaugcaa    60
gucgagcgga ugaagggagc uugcuccugg auucagcggc ggacgggugg guaaugccua   120
ggaaucugcc ugguagugg  ggauaacguc cggaaacggg cgcuaauacc gcauacgucc   180
ugagggagaa aguggggggau cuucggaccu cacgcuauca gaugagccua ggucggauua   240
gcuaguuggu gggguaaagg ccaccaagg cgacgauccg uaacggucu gagaggauga   300 ucagucacac uggaacugag acacggucca gacuccuacg ggaggcagca gugggggauua   360 uuggacaaug ggcgaaagcc ugauccagcc augccgcgug ugugaagaag gucuucggau   420
uguaaagcac uuuaaguugg gaggaagggc aguaaguuaa uaccuugcug uuugacguu    480 accaacagaa uaagcaccgg cuaacuucgu gccagcagcc gcgguaauac gaagggugca   540
agcguuaauc ggaauuacug ggcguaaagc gcgcuaggu gguucagcaa guuggaugug   600 aauccccgg gcucaaccug ggaacugcau ccaaaacuac ugagcuagag uacgguagag   660
ggugguggaa uuuccugugu agcgugaaa ugcuagauaa uaggaaggaa caccagugge   720 gaaggcgacc accuggacug auacugacac ugaggugcga aagcgugggg agcaaacagg   780
auuagauacc cugguagucc acgccguaaa cgaugcgac uagccguugg gauccuugag   840
aucuuagugg cgcagcuaac gcgauaaguc gaccgccugg ggaguacggc cgcaagguua   900
aaacucaaau gaauugacgg gggcccgcac aagcgguga  gcaugugguu uaauucgaag   960
caacgcgaag aaccuuaccu ggccuugaca ugcugagaac uuccagaga uggauuggug  1020 ccuucgggaa cucagacaca ggugcugcau ggcugucguc agcucuguc gugagauguu  1080 ggguuaaguc ccguaacgag cgcaacccuu guccuuaguu accagcaccu cggguggca   1140 cucuaaggag acugccggug acaaaccgga ggaagggg gaugacguca agucaucaug   1200
gcccuuacgg ccagggcuac acacgugcua caauggucgg uacaaagggu ugcgaagccg   1260
```

```
cgagguggag cuaaucccau aaaaccgauc guaguccgga ucgcagucug caacucgacu    1320
gcgugaaguc ggaaucgcua guaaucguga aucagaaugu cacggugaau acguucccgg    1380
gccuuguaca caccgcccgu cacaccaugg gaguggguug cuccagaagu agcuagucua    1440
accgcaaggg ggacgguuac cacggaguga uucauggcug ggugaaguc guaacaaggu     1500 agccguaggg gaaccugcgg cuggaucacc uccuua                              1536
```

<210> SEQ ID NO 150
<211> LENGTH: 1537
<212> TYPE: RNA
<213> ORGANISM: Escherichia coli

<400> SEQUENCE: 150

```
aaauugaaga guuugaucau ggcucagauu gaacgcuggc ggcaggccua acacaugcaa      60
gucgagcgga ugaagggagc uugcuccugg auucagcggc ggacggguga guaaugucug     120
ggaaacugcc ugaugguggg ggauaacuac uggaaacggu agcuaauacc gcauaacguc     180
gcaagaccaa agagggggac cuucgggccu cuugccaucg gaugugccca gaugggauua     240
gcuaguaggu gggguaacgg cucaccuagg cgacgauccc uagcuggucu gagaggauga     300
ccagccacac uggaacugag acacgguccca gacuccuacg ggaggcagca gugggggaaua     360 uugcacaaug gcgcaagcc ugaugcagcc augccgcgug uaugaagaag gcuucggcu      420 uguaaaguac uuucagcggg gaggaagggg aguaaaguua uaccuuugc ucauuugacg      480 uuacccgcag aagaagcacc ggcuaacucc gugccagcag ccgcgguaau acggagggug     540
caagcguuaa ucggaauuac ugggcguaaa gcgcacgcag gcgguuguu aagucagaug       600 ugaaauccc gggcucaacc ugggaacugc aucugauacu ggcaagcuug agucucguag      660
agggggguag aauuccaggu guagcgguga aaugcguaga gaucuggagg aauaccggug     720
gcgaaggcgg ccccuggac gaagacugac gcucaggugc gaaagcgugg ggagcaaaca     780
ggauuagaua cccugguagu ccacgccgua aacgaugucg acuuggaggu ugugcccuug     840
aggcguggcu uccggagcua acgcguuaag ucgaccgccu ggggaguacg gccgcaaggu     900
uaaaacucaa augaauugac ggggggcccgc acaagcgguug gagcaugugg uuuaauucga     960
ugcaacgcga agaaccuuac cuggucuuga cauccacgga aguuucaga gaugagaaug    1020 ugccuucggg aaccgugaga caggcugcau ggcugucgu cagcucgugu ugugaaaugu    1080 ugggguuaagu cccgcaacga gcgcaacccu uauccuuugu ugccagcggu ccggccggga    1140
acucaaagga gacugccagu gauaaacugg aggaaggugg ggaugacguc aagucaucau    1200
ggcccuuacg accagggcua cacacgugcu acaauggcgc auacaaagag aagcgaccuc    1260
gcgagagcaa gcggaccuca uaaagucgcu cguaguccgg auuggagucu gcaacucgac    1320
uccaugaagu cggaaucgcu aguaaucgug gaucagaaug ccacggugaa uacguucccg    1380
ggccuuguac acaccgcccg ucacaccaug ggaguggguu gcaaaagaag uaggagcuu    1440 aaccuucggg agggcgcuua ccacuuuguug auucaguggcu ggggugaagu cguaacaagg    1500
uaaccguagg ggaaccugcg guuggaucac cuccuua                            1537
```

<210> SEQ ID NO 151
<211> LENGTH: 1535
<212> TYPE: RNA
<213> ORGANISM: Artificial Sequence
<220> FEATURE:
<223> OTHER INFORMATION: Description of Artificial Sequence: Synthetic
      nucleotide sequence

<400> SEQUENCE: 151

```
gaacugaaga guuugaucau ggcucagauu gaacgcuggc ggcaggccua acacaugcaa      60
gucgagcgga ugaagggagc uugcuccugg auucagcggc ggacggguga guaaugccua     120
ggaaucugcc ugguagugg ggauaacguc cggaaacggg cgcuaauacc gcauaacguc     180
gcaagaccaa aguggggau cuucggaccu cacgcuauca gaugagccua ggucggauua     240
gcuaguuggu gggguaaagg ccaccaagg cgacgauccg uaacggucu gagaggauga     300 ucagucacac uggaacugag acacggucca gacuccuacg ggaggcagca guggggaaua     360
uuggacaaug ggcgaaagcc ugauccagcc augccgcgug ugugaagaag gucuucggau     420
uguaaagcac uuuaguuggg aggaagggca guaaguuaau accuugcugu uuugacguua     480
ccaacagaau aagcaccggc uaacuucgug ccagcagccg cgguaauacg aagggugcaa     540
gcguuaaucg gaauuacugg gcguaaagcg cgcguaggu guucagcaag uuggaugugaa    600 aaucccggg cucaaccugg gaacugcauc caaaacuacu gagcuagagu acgguagagg     660 guggu ggaau uccugugua gcggugaaau gcguagauau aggaaggaac accagugcg     720 aaggcgacca ccuggacuga uacugacacu gaggugcgaa agcgugggga gcaaacagga     780
uuagauaccc cgguagucca cgccguaaac gaugucgacu agccguuggg auccuugaga     840 ucuuagugc gcagcuaacg cgauaagucg accgccuggg gaguacggcc gcaagguuaa     900
aacucaaaug aauugacggg ggcccgcaca agcgguggag caugguuguu aauucgaagc     960
aacgcgaaga accuuaccug gccuugacau gcugagaacu uccagagau ggauugguc    1020 cuucgggaac ucagacacag gugcugcaug gcugucguca gcucgugucg ugagauguug    1080
gguuaagucc cguaacgagc gcaacccuug uccuuaguua ccagcaccuc ggugugcac     1140 ucuaaggaga cugccgguga caaaccggag gaaggugggg augacgucaa gucaucaug    1200 cccuuacggc cagggcuaca cacgugcuac aauggucggu acaaagggu ucgaagccgc    1260 gagguggagc uaaucccaua aaaccgaucg uagccggau cgcagucugc aacucgacug    1320
cgugaagucg gaaucgcuag uaaucgugaa ucagaaugu acggugaaua cguucccggg    1380
ccuuguacac accgcccguc acaccauggg aguggguugc uccagaagua gcuagucuaa    1440
ccgcaagggg gacgguuacc acggagugau ucauggcugg ggugaagucg uaacaaggua    1500
accguagggg aaccugcggu uggaucaccu ccuua                               1535

<210> SEQ ID NO 152
<211> LENGTH: 80
<212> TYPE: RNA
<213> ORGANISM: Pseudomonas aeruginosa

<400> SEQUENCE: 152
gugggggaua acguccggaa acgggcgcua auaccgcaua cguccugagg gagaaagugg      60
gggaucuucg gaccucacgc                                                  80

<210> SEQ ID NO 153
<211> LENGTH: 91
<212> TYPE: PRT
<213> ORGANISM: Pseudomonas aeruginosa

<400> SEQUENCE: 153

Met Ala Asn Thr Pro Ser Ala Lys Lys Arg Ala Lys Gln Ala Glu Lys
 1               5                  10                  15

Arg Arg Ser His Asn Ala Ser Leu Arg Ser Met Val Arg Thr Tyr Ile
            20                  25                  30

Lys Asn Val Val Lys Ala Ile Asp Ala Lys Asp Leu Glu Lys Ala Gln
```

-continued

```
                35                  40                  45
Ala Ala Phe Thr Ala Ala Val Pro Val Ile Asp Arg Met Ala Asp Lys
         50                  55                  60

Gly Ile Ile His Lys Asn Lys Ala Ala Arg His Lys Ser Arg Leu Ser
 65                  70                  75                  80

Gly His Ile Lys Ala Leu Ser Thr Ala Ala Ala
                 85                  90

<210> SEQ ID NO 154
<211> LENGTH: 87
<212> TYPE: PRT
<213> ORGANISM: Escherichia coli

<400> SEQUENCE: 154

Met Ala Asn Ile Lys Ser Ala Lys Lys Arg Ala Ile Gln Ser Glu Lys
 1               5                  10                  15

Ala Arg Lys His Asn Ala Ser Arg Arg Ser Met Met Arg Thr Phe Ile
                 20                  25                  30

Lys Lys Val Tyr Ala Arg Ile Glu Ala Gly Asp Lys Ala Ala Ala Gln
             35                  40                  45

Lys Ala Phe Asn Glu Met Gln Pro Ile Val Asp Arg Gln Ala Ala Lys
         50                  55                  60

Gly Leu Ile His Lys Asn Lys Ala Ala Arg His Lys Ala Asn Leu Thr
 65                  70                  75                  80

Ala Gln Ile Asn Lys Leu Ala
                 85

<210> SEQ ID NO 155
<211> LENGTH: 106
<212> TYPE: PRT
<213> ORGANISM: Thermus sp.

<400> SEQUENCE: 155

Met Ala Gln Lys Lys Pro Lys Arg Asn Leu Ser Ala Leu Lys Arg His
 1               5                  10                  15

Arg Gln Ser Leu Lys Arg Arg Leu Arg Asn Lys Ala Lys Lys Ser Ala
                 20                  25                  30

Ile Lys Thr Leu Ser Lys Lys Ala Ile Gln Leu Ala Gln Glu Gly Lys
             35                  40                  45

Ala Glu Glu Ala Leu Lys Ile Met Arg Lys Ala Glu Ser Leu Ile Asp
         50                  55                  60

Lys Ala Ala Lys Gly Ser Thr Leu His Lys Asn Ala Ala Ala Arg Arg
 65                  70                  75                  80

Lys Ser Arg Leu Met Arg Lys Val Arg Gln Leu Leu Glu Ala Ala Gly
                 85                  90                  95

Ala Pro Leu Ile Gly Gly Gly Leu Ser Ala
            100                 105
```